United States Patent
Kawano

(10) Patent No.: US 8,235,888 B2
(45) Date of Patent: Aug. 7, 2012

(54) SYSTEM FOR GUIDING CAPSULE MEDICAL DEVICE

(75) Inventor: Hironao Kawano, Machida (JP)

(73) Assignee: Olympus Medical Systems Corp., Tokyo (JP)

( * ) Notice: Subject to any disclaimer, the term of this patent is extended or adjusted under 35 U.S.C. 154(b) by 938 days.

(21) Appl. No.: 12/268,094

(22) Filed: Nov. 10, 2008

(65) Prior Publication Data

US 2010/0010305 A1 Jan. 14, 2010

Related U.S. Application Data

(60) Provisional application No. 61/078,828, filed on Jul. 8, 2008.

(51) Int. Cl.
 *A61B 1/00* (2006.01)
 *A61B 1/04* (2006.01)
(52) U.S. Cl. .......... 600/118; 600/101; 600/117
(58) Field of Classification Search .......... 600/101, 600/103, 117, 118, 109, 160, 424
See application file for complete search history.

(56) References Cited

U.S. PATENT DOCUMENTS

| | | | | |
|---|---|---|---|---|
| 6,339,446 | B1 * | 1/2002 | Miyoshi | 348/65 |
| 7,173,507 | B2 * | 2/2007 | Ries | 335/299 |
| 7,803,108 | B2 * | 9/2010 | Honda | 600/118 |
| 7,869,856 | B2 * | 1/2011 | Refael | 600/407 |
| 8,038,607 | B2 * | 10/2011 | Fujimori | 600/160 |
| 2005/0043583 | A1 * | 2/2005 | Killmann et al. | 600/109 |
| 2006/0004255 | A1 * | 1/2006 | Iddan et al. | 600/160 |
| 2007/0118018 | A1 * | 5/2007 | Gilad et al. | 600/160 |
| 2007/0161862 | A1 * | 7/2007 | Yokoi et al. | 600/175 |
| 2007/0185381 | A1 * | 8/2007 | Kimoto et al. | 600/117 |
| 2007/0244388 | A1 * | 10/2007 | Sato et al. | 600/424 |
| 2008/0242926 | A1 * | 10/2008 | Nishino | 600/109 |
| 2008/0306340 | A1 * | 12/2008 | Uchiyama et al. | 600/117 |

(Continued)

FOREIGN PATENT DOCUMENTS

EP 2 060 221 A1 5/2009

(Continued)

OTHER PUBLICATIONS

Extended European Search Report dated Oct. 16, 2009.

*Primary Examiner* — John P Leubecker
(74) *Attorney, Agent, or Firm* — Scully, Scott, Murphy & Presser, P.C.

(57) ABSTRACT

A system for guiding capsule medical device is provided with a capsule medical device, a magnetic guidance device, an operation input unit, a control device, and an image display device. The capsule medical device is includes therein a first and second imaging units that image images in imaging directions different from each other and a permanent magnet. The magnetic guidance device applies a magnetic field to the permanent magnet to magnetically guide the capsule medical device in a subject. The operation input unit receives operation information to operate magnetic guidance of the capsule medical device. The control device controls the magnetic guidance device to magnetically guide the capsule medical device in response to the operation information input through the operation input unit. The image display device displays a first in-vivo image of the subject imaged by the first imaging unit and a second in-vivo image of the subject imaged by the second imaging unit, and clearly shows which of the first and second in-vivo images is an operation target image at the time of the magnetic guidance of the capsule medical device.

8 Claims, 39 Drawing Sheets

U.S. PATENT DOCUMENTS

| | | | |
|---|---|---|---|
| 2011/0034795 A9 * | 2/2011 | Gilad et al. | 600/407 |
| 2011/0060189 A1 * | 3/2011 | Belson | 600/117 |

FOREIGN PATENT DOCUMENTS

| | | |
|---|---|---|
| EP | 2 062 522 A1 | 5/2009 |
| JP | 2002-248078 | 9/2002 |
| WO | WO 2006/005075 | 1/2006 |
| WO | WO 2008/029460 A1 | 3/2008 |
| WO | WO 2008/032713 A1 | 3/2008 |
| WO | WO 2008/041809 A1 | 4/2008 |

* cited by examiner

FIG.15
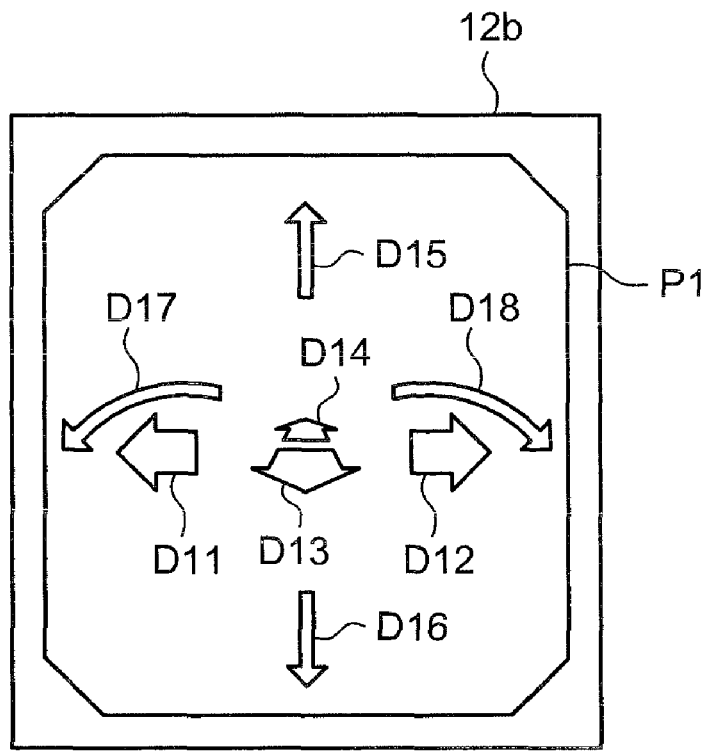
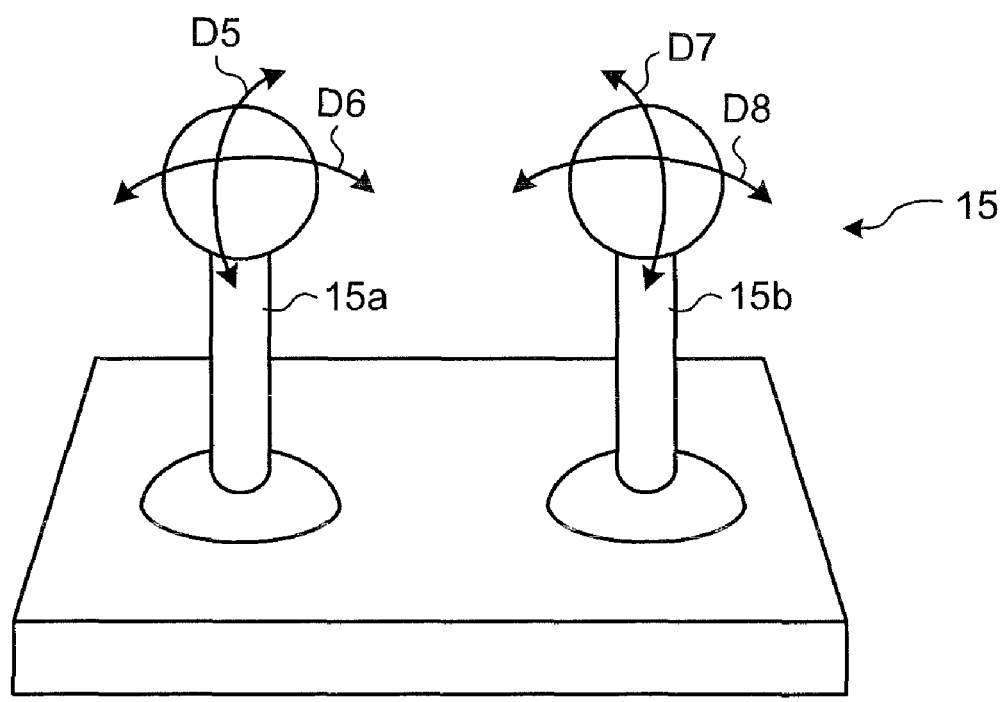

FIG.21
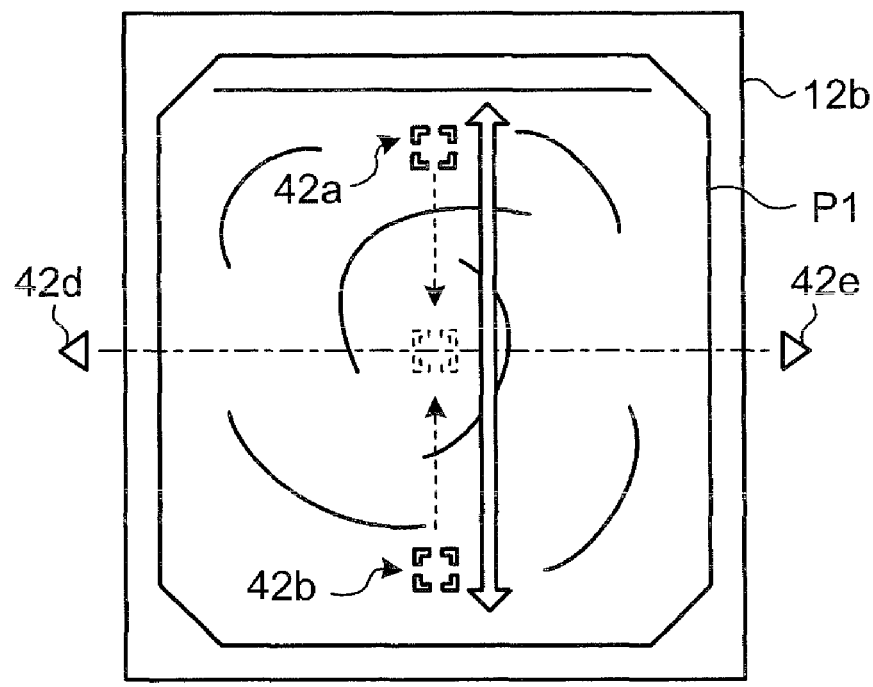
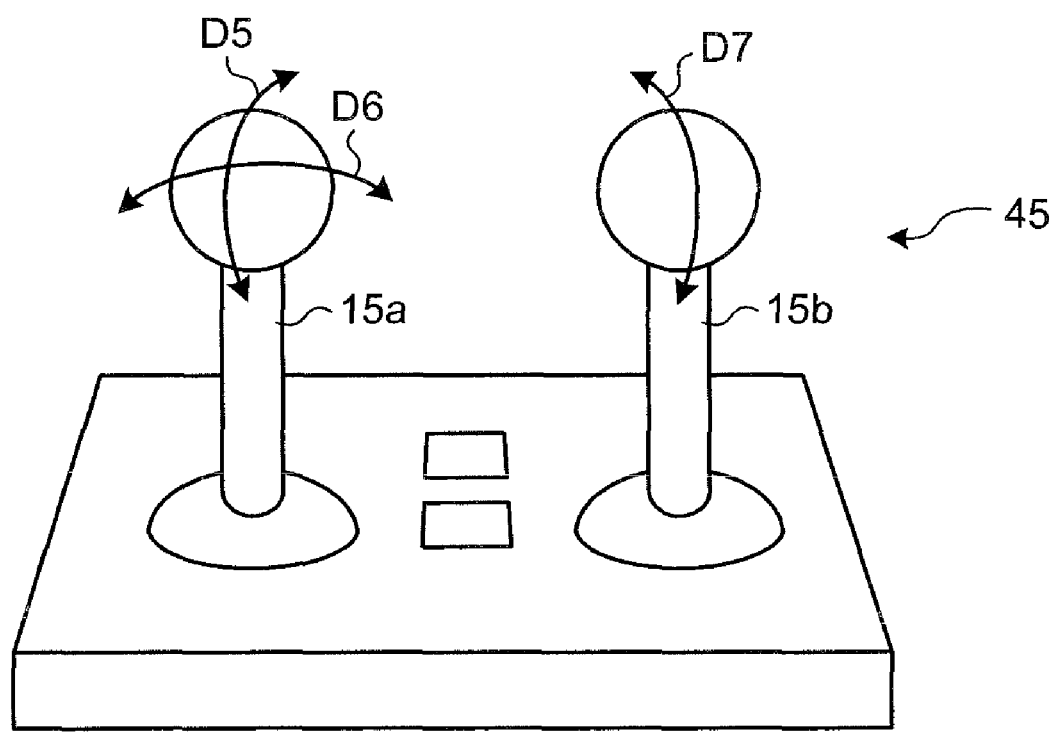

(OPERATION TARGET IMAGE)   (NON-OPERATION TARGET IMAGE)

TYPE J1

TYPE J2

TYPE J3

TYPE J4

TYPE J5

TYPE J6

TYPE J7

TYPE J8

SYSTEM FOR GUIDING CAPSULE MEDICAL DEVICE

CROSS-REFERENCE TO RELATED APPLICATIONS

This non-provisional application claims the benefit of U.S. Provisional Application Ser. No. 61/078,828, filed Jul. 8, 2008.

BACKGROUND OF THE INVENTION

1. Field of the Invention

The present invention relates to a system for guiding capsule medical device for magnetically guiding a capsule medical device introduced into an organ of a subject such as a patient.

2. Description of the Related Art

Conventionally, the capsule medical device provided with an imaging function and a radio communication function in a capsule casing, which can be introduced into the organ of the subject such as the patient, has appeared. The capsule medical device is introduced into the organ of the subject by oral intake or the like, and thereafter moves in the digestive tract by a peristaltic action or the like. Such a capsule medical device in the subject sequentially images in the organ of the subject (hereinafter, also referred to as in-vivo images) in a time period from introduction into the organ of the subject to discharge out of the same, and sequentially transmits by radio the obtained in-vivo images to a receiving device outside of the subject.

The in-vivo image imaged by such a capsule medical device is captured in an image display device through the receiving device. The image display device displays the captured in body images on a display by still image display or moving image display. A user such as a doctor or a nurse observes the in-vivo image of the subject displayed on the image display device, and examines inside of the organ of the subject through an observation of such an in-vivo image.

Recently, on the other hand, the system for guiding capsule medical device for magnetically guiding (hereinafter, referred to as magnetic guidance) the capsule medical device in the subject is suggested. (refer to the Japanese Patent Applications Laid-Open Nos. 2006-263167 and 2007-330811, for example). In general, in the system for guiding capsule medical device, the capsule medical device is further provided with a permanent magnet in the capsule casing, and the image display device displays the in-vivo images sequentially imaged by the capsule medical device in the subject in real time. The system for guiding capsule medical device applies a magnetic field to the capsule medical device in such a subject, and magnetically guides the capsule medical device in the subject to a desired location by magnetic force of the applied magnetic field. The user uses an operating unit of the system for guiding capsule medical device to operate the magnetic guidance of such a capsule medical device while referring to the in-vivo image displayed on the image display device.

SUMMARY OF THE INVENTION

A system for guiding capsule medical device according to an aspect of the present invention includes a capsule medical device includes therein first and second imaging units that image images in imaging directions different from each other and a permanent magnet; a magnetic guidance device that applies a magnetic field to the permanent magnet to magnetically guide the capsule medical device in a subject; an operation input unit that receives operation information to operate magnetic guidance of the capsule medical device; a control device that controls the magnetic guidance device to magnetically guide the capsule medical device in response to the operation information input through the operation input unit; and an image display device that displays a first in-vivo image of the subject imaged by the first imaging unit and a second in-vivo image of the subject imaged by the second imaging unit, and clearly shows which of the first and second in-vivo images is an operation target image at the time of the magnetic guidance of the capsule medical device.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 15 is a schematic diagram showing one example of a moving direction of an operation target image in association with an operation of the magnetic guidance of the capsule medical device;

FIG. 21 is a schematic diagram illustrating the display process of information indicating that elevation angle information and operation information of the capsule medical device are input, by the image display device;

DETAILED DESCRIPTION OF THE PREFERRED EMBODIMENTS

Hereinafter, a system for guiding capsule medical device, which is a best mode for carrying out the present invention, is described. Meanwhile, although a capsule medical device incorporating a function of imaging an in-vivo image and a radio communication function is illustrated hereinafter as one example of the capsule medical device, which is magnetically guided by the system for guiding capsule medical device according to the present invention, the present invention is not limited to this embodiment.

Figure 1:
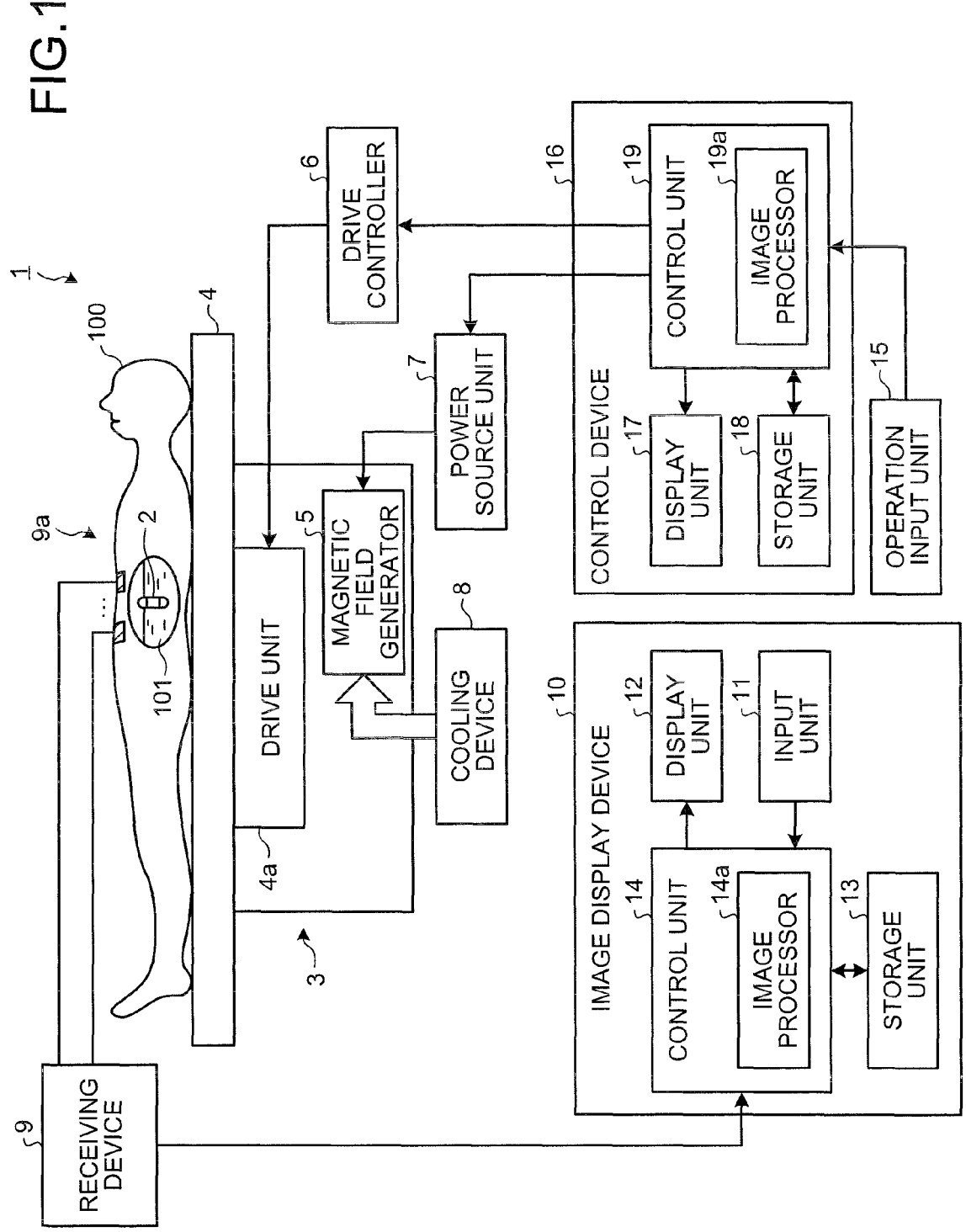
FIG. 1 is a block diagram schematically showing one configuration example of a system for guiding capsule medical device according to a first embodiment of the present invention.

First, the system for guiding capsule medical device according to a first embodiment of the present invention is described. FIG. 1 is a block diagram schematically showing one configuration example of the system for guiding capsule medical device according to the first embodiment of the present invention. As shown in FIG. 1, the system for guiding capsule medical device 1 according to the first embodiment is provided with a capsule medical device 2 for imaging the in-vivo image of a subject 100 such as a patient, a magnetic guidance device 3 for magnetically guiding the capsule medical device 2 in the subject 100, a drive controller 6 for controlling drive of the magnetic guidance device 3, a power unit 7 for supplying power to the magnetic guidance device 3, and a cooling device 8 for cooling the magnetic guidance device 3. Also, the system for guiding capsule medical device 1 is provided with a receiving device 9 for receiving an image signal from the capsule medical device 2 in the subject 100, an image display device 10 for displaying the in-vivo image imaged by the capsule medical device 2 in the subject 100, an operation input unit 15 for operating magnetic guidance of the capsule medical device 2, and a control device 16 for controlling the magnetic guidance of the capsule medical device 2.

The capsule medical device 2 is a capsule-type medical device for obtaining the in-vivo image of the subject 100, and incorporates the imaging function and the radio communication function. The capsule medical device 2 is introduced into an organ of the subject 100 by oral intake or the like. Thereafter, the capsule medical device 2 in the subject 100 moves in a digestive tract to be finally discharged out of the subject 100. The capsule medical device 2 sequentially images the in-vivo images of the subject 100 in a time period from introduction into the subject 100 to discharge out of the same, and sequentially transmits by radio the obtained in-vivo images to an external receiving device 9. In addition, the capsule medical device 2 incorporates a magnetic body such as a permanent magnet. The capsule medical device 2 floats in liquid 101 introduced into the organ (such as stomach) of the subject 100, and is magnetically guided by an external magnetic guidance device 3.

The magnetic guidance device 3 is for magnetically guiding the capsule medical device 2 in the subject 100, and is provided with a bed 4 for supporting the subject 100, and a magnetic field generator 5 for generating a guidance magnetic field for magnetically guiding the capsule medical device 2 in the subject 100.

The bed 4 is a movable bed of which table portion for supporting the subject 100 is movable, and is provided with a drive unit 4a. The drive unit 4a is realized by using an actuator, rail, and the like for realizing movement of such a table portion. The drive unit 4a drives based on control of the drive controller 6, and parallelly moves the table portion of the bed 4 in a state of supporting the subject 100 from front to back and from side to side. The bed 4 changes a relative location of the subject 100 with respect to the magnetic field generator 5 by an action of the drive unit 4a.

The magnetic field generator 5 is realized by using a plurality of coils or the like to generate the guidance magnetic field by using the power supplied by the power unit 7. The magnetic field generator 5 applies the generated guidance magnetic field to the magnetic body in the capsule medical device 2 to magnetically capture the capsule medical device 2 by an action of the guidance magnetic field.

The magnetic guidance device 3 provided with the bed 4 and the magnetic field generator 5 magnetically guides the capsule medical device 2 in the subject 100 on the bed 4 by combining the drive of the bed 4 and the guidance magnetic field by the magnetic field generator 5. Specifically, the magnetic guidance device 3 changes the relative location between the subject 100 and the magnetic field generator 5 by the drive of the bed 4 while magnetically capturing the capsule medical device 2 in the subject 100 by the action of the guidance magnetic field by the magnetic field generator 5, thereby controlling a three-dimensional location of the capsule medical device 2 in the subject 100. Also, the magnetic guidance device 3 controls three-dimensional position of the capsule medical device 2 in the subject 100 by changing a magnetic field direction of the guidance magnetic field acting on the capsule medical device 2 in the subject 100.

The drive controller 6 controls the drive unit 4a of the above-described bed 4 based on the control of the control device 16. Specifically, the drive controller 6 controls the drive unit 4a to parallelly move the table portion of the bed 4 in a direction corresponding to a magnetic guidance direction of the capsule medical device 2 in the subject 100. The power unit 7 supplies power (such as alternating current) required for generating the above-described guidance magnetic field to the magnetic field generator 5 based on the control of the control device 16. In this case, the power unit 7 appropriately supplies the required power to each of a plurality of coils included in the magnetic field generator 5. Meanwhile, the magnetic field direction and magnetic field strength of the guidance magnetic field by the above-described magnetic field generator 5 are controlled by a current amount from the power unit 7 to each coil in the magnetic field generator 5. The cooling device 8 cools the above-described magnetic field generator 5, thereby preventing a temperature of the magnetic field generator 5 from rising due to the generation of the guidance magnetic field.

The receiving device 9 is provided with a plurality of antennas 9a, and receives the in-vivo image of the subject 100 from the capsule medical device 2 through the antennas 9a. Specifically, the antennas 9a are dispersedly arranged on a body surface of the subject 100 to capture a radio signal transmitted by the capsule medical device 2 in the subject 100. The receiving device 9 sequentially receives the radio signal from the capsule medical device 2 through the antennas 9a. The receiving device 9 selects the antenna of which received electric-field strength is the highest from the antennas 9a, and performs a demodulation process or the like on the radio signal from the capsule medical device 2 received through the selected antenna. Thereby, the receiving device 9 extracts image data by the capsule medical device 2, that is to say, in-vivo image data of the subject 100, from the radio signal. The receiving device 9 transmits the image signal including the extracted in-vivo image data to the image display device 10.

The image display device 10 is provided with an input unit 11, a display unit 12, a storage unit 13, and a controller 14 as shown in FIG. 1, and displays the in-vivo image of the subject 100 by the capsule medical device 2 in a display mode in which an upward and downward direction of an object in the in-vivo image associated with the magnetic guidance of the capsule medical device 2 and an upward and downward direction of a display screen conform to each other. The upward and downward direction of the object used herein may include an upward and downward moving direction of the object in the in-vivo image associated with the magnetic guidance of the capsule medical device 2. This applies also to the upward and downward direction of the object in the present invention.

The input unit 11 is realized by using an input device such as a keyboard and a mouse to input various pieces of information to the controller 14 in response to an input operation by a user such as a doctor and a nurse. The various pieces of information input by the input unit 11 to the controller 14 include instruction information to instruct the controller 14, patient information and examination information of the subject 100, for example. Meanwhile, the patient information of the subject 100 is specifying information to specify the subject 100, and includes, for example, a patient name, a patient ID, a birth date, sex, age of the subject 100. Also, the examination information of the subject 100 is the specifying information to specify an examination to observe an inside of the digestive tract by introducing the capsule medical device 2 into the digestive tract of the subject 100, and includes, for example, an examination ID, and an examination date.

The display unit 12 is realized by using various displays such as a CRT display or a liquid crystal display to display the various pieces of information instructed to be displayed by the controller 14. Specifically, the display unit 12 displays an in-vivo image group of the subject 100 imaged by the capsule medical device 2, for example, based on the control of the controller 14. In this case, the display unit 12 displays each in-vivo image in such an in-vivo image group as a still image or as a moving image by conforming the upward and downward direction of the object in the in-vivo image associated with the magnetic guidance of the capsule medical device 2 to the upward and downward direction of the display screen. Also, the display unit 12 displays a reduced image of the in-vivo image, which is selected or marked by the input operation of the input unit 11 from such an in-vivo image group, the patient information, the examination information, and the like of the subject 100.

The storage unit 13 is realized by using a storage medium such as a flash memory or a hard disk for rewritably saving the information. The storage unit 13 stores the various pieces of information instructed to be stored by the controller 14 and transmits the information instructed to be read from the stored various pieces of information by the controller 14 to the controller 14. Meanwhile, the various pieces of information stored in the storage unit 13 includes each image data in the in-vivo image group of the subject 100 imaged by the capsule medical device 2, data of the in-vivo image selected or marked from each in-vivo image displayed on the display unit 12 by the input operation of the input unit 11, and input information by the input unit 11 such as the patient information of the subject 100, for example.

The controller 14 controls each operation of the input unit 11, the display unit 12, and the storage unit 13, which are components of the image display device 10, and controls input and output of the signal among each component. Specifically, the controller 14 controls the display unit 12 to sequentially obtain the in-vivo images of the subject 100 imaged by the capsule medical device 2 from the receiving device 9, and to display each of the obtained in-vivo images of the subject 100 in real time. Next, the controller 14 controls the storage unit 13 to store the in-vivo image group of the subject 100 obtained from the receiving device 9. Also, when the instruction information to instruct to selectively save the in-vivo image is input by the input unit 11, the controller 14 extracts the in-vivo image instructed to be saved by the instruction information (that is to say, the selected image by the user) from the in-vivo image group of the subject 100. The controller 14 controls the display unit 12 to add a mark to the extracted in-vivo image, and controls the storage unit 13 to store the in-vivo image data with the mark in association with each other. Further, the controller 14 controls the display unit 12 to additionally display the reduced image (such as a thumbnail image) of the in-vivo image. On the other hand, when the instruction information to instruct to switch the display mode of the in-vivo image is input by the input unit 11, the controller 14 controls the display unit 12 to switch a display format of each in-vivo image of the subject 100 from the moving image display to the still image display, or controls the display unit 12 to switch from the still image display to the moving image display, based on the instruction information.

Also, the controller 14 has an image processor 14a. The image processor 14a generates various pieces of image information to be displayed on the display unit 12. Specifically, the image processor 14a obtains an image signal from the receiving device 9, and performs predetermined image processing to the obtained image signal to generate the in-vivo image of the subject 100, that is to say, the in-vivo image imaged by the capsule medical device 2. The image processor 14a sequentially generates the in-vivo image of the subject 100 based on the obtained image signal, each time the image processor 14a obtains the image signal from the receiving device 9. Also, the image processor 14a conforms the upward and downward direction of the object in the in-vivo image associated with the magnetic guidance of the capsule medical device 2 to the upward and downward direction of the display screen of the display unit 12, for each in-vivo image of the subject 100. In this case, the image processor 14a conforms a direction of intersection line of an imaging surface of the capsule medical device 2 and a vertical plane in such an in-vivo image to the upward and downward direction of the display screen of the display unit 12. The controller 14 allows the display unit 12 to display each in-vivo image of the subject 100 in the display mode in which such a direction of intersection line and the upward and downward direction of the display screen conform to each other.

The operation input unit 15 is for operating the magnetic guidance of the capsule medical device 2 by the above-described magnetic guidance device 3. Specifically, the operation input unit 15 is realized by using various input devices such as a joystick, a keyboard, and a mouse. The operation input unit 15 inputs various pieces of information to the control device 16 in response to the input operation by the user such as the doctor or the nurse. Meanwhile, the various pieces of information to be input to the control device 16 by the operation input unit 15 includes, for example, operation information to specify the magnetic guidance direction and a magnetic guidance speed of the capsule medical device 2, which is a magnetic guidance operational target, physical information such as mass, a shape, a location of center of gravity, and magnetic moment of the capsule medical device 2, and density information of the liquid 101 in which the capsule medical device 2 floats in the subject 100.

The control device 16 is provided with a display unit 17, a storage unit 18, and a controller 19, as shown in FIG. 1, and controls the magnetic guidance of the capsule medical device 2 by the magnetic guidance device 3 based on the operation information input by the operation input unit 15.

The display unit 17 is realized by using various displays such as the CRT display or the liquid crystal display to display various pieces of information instructed to be displayed by the controller 19. Specifically, the display unit 17 displays information indicating the location, the position, the direction or the like of the capsule medical device 2 in the subject 100, relative location information of the operation input unit 15 with respect to the bed 4, body posture information of the subject 100 on the bed 4, and the like, based on the control of the controller 19.

The storage unit 18 is realized by using the storage medium such as the flash memory or the hard disk for rewritably saving the information. The storage unit 18 stores various pieces of information instructed to be stored by the controller 19, and transmits the information instructed to be read from the stored various pieces of information by the controller 19 to the controller 19. Meanwhile, the various pieces of information stored in the storage unit 18 include, for example, the physical information of the capsule medical device 2, the density information of the liquid 101, the operation information of the capsule medical device 2, information of a magnetic guidance state (location, position, and direction) of the capsule medical device 2 in the subject 100.

The controller 19 controls each operation of the display unit 17 and the storage unit 18, which are components of the control device 16, and controls input and output of the signal among each component and input of the signal from the operation input unit 15. Specifically, when the operation information is input by the operation input unit 15, the controller 19 controls the magnetic guidance device 3 to perform the magnetic guidance of the capsule medical device 2 according to the magnetic guidance direction and the magnetic guidance speed specified by the input operation information. In this case, the controller 19 controls the current amount of the power unit 7 relative to the magnetic field generator 5 based on the input operation information, and controls the magnetic field generator 5 to generate the guidance magnetic field required for the magnetic guidance of the capsule medical device 2 according to the magnetic guidance direction and the magnetic guidance speed based on the operation information, through the control of the power unit 7. Also, the controller 19 controls the drive controller 6 based on the operation information, and controls the drive unit 4a to parallelly move the table portion of the bed 4 according to the magnetic guidance direction and the magnetic guidance speed based on the operation information, through the control of the drive controller 6.

Also, the controller 19 has an image processor 19a. The image processor 19a generates the various pieces of image information to be displayed on the display unit 17. Specifically, the image processor 19a generates the image information indicating the magnetic guidance state of the capsule medical device 2 in the subject 100. More specifically, the image processor 19a generates the image information indicating the location, the image information indicating the position, and the image information indicating the direction of the capsule medical device 2 in the subject 100, as the image information indicating the magnetic guidance state of the capsule medical device 2. Also, the image processor 19a generates the image information indicating the relative location of the operation input unit 15 with respect to the bed 4 and the image information indicating the body posture of the subject 100 on the bed 4. The controller 19 allows the display unit 17 to display the various pieces of image information generated by the image processor 19a, and controls the display unit 17 to update the image information indicating the location, the image information indicating the position, and the image information indicating the direction of the capsule medical device 2 according to a result of the magnetic guidance of the capsule medical device 2.

Figure 2:
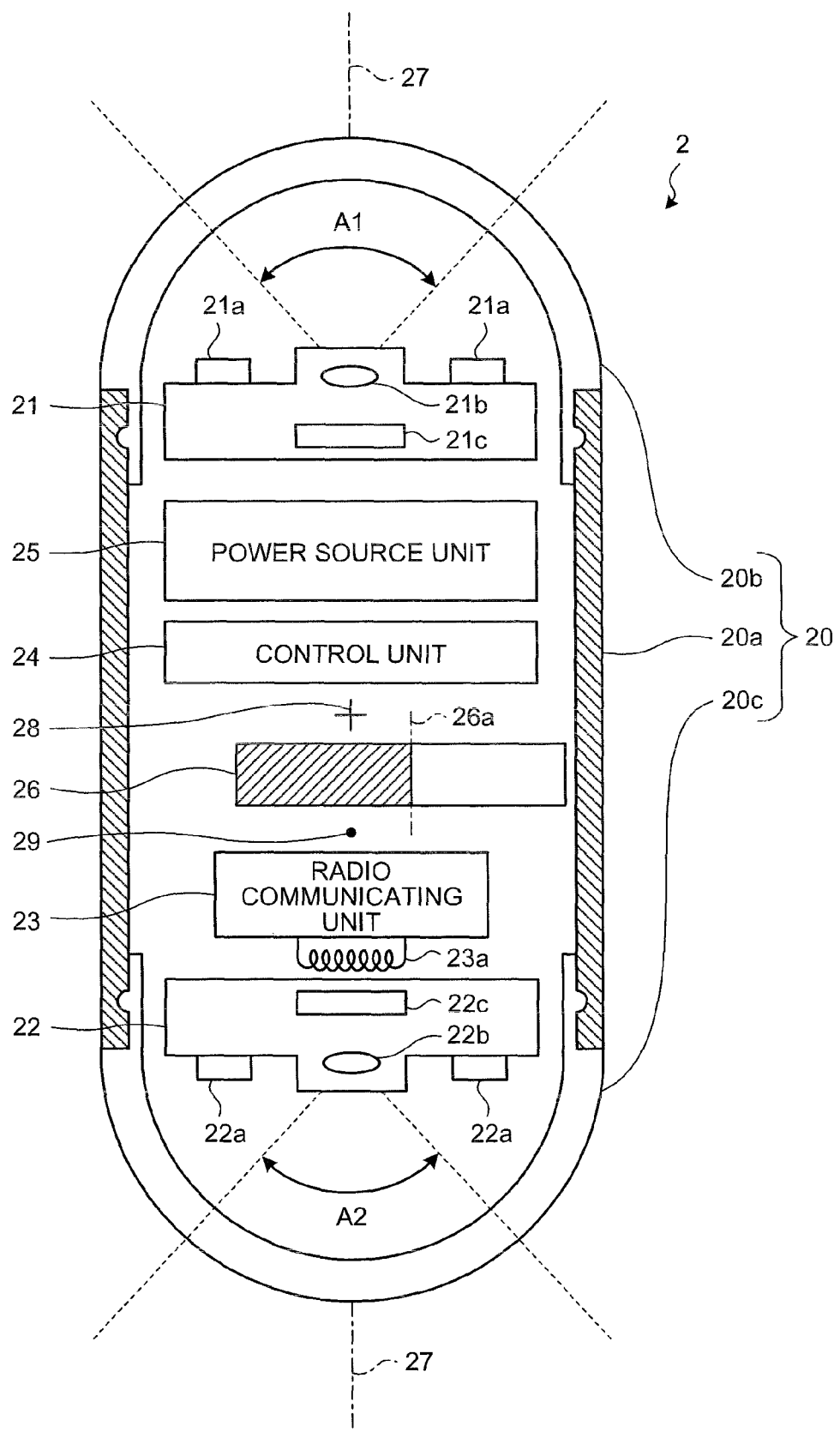
FIG. 2 is a schematic cross-sectional view showing one configuration example of a capsule medical device, which is a magnetic guidance target of the system for guiding capsule medical device according to the present invention.

Next, the capsule medical device 2, which is the magnetic guidance target of the system for guiding capsule medical device 1 according to the first embodiment of the present invention, is described. FIG. 2 is a schematic cross-sectional view showing one configuration example of the capsule medical device, which is the magnetic guidance target of the system for guiding capsule medical device according to the present invention. As shown in FIG. 2, the capsule medical device 2 is provided with a capsule casing 20, which is an outer cover formed into a size so as to be easily introduced into the organ of the subject 100, and imaging units 21 and 22 for imaging the images of the object in imaging directions different from each other. Also, the capsule medical device 2 is provided with a radio communication unit 23 for transmitting by radio each image imaged by the imaging units 21 and 22 to the outside, a controller 24 for controlling each component of the capsule medical device 2, and a power unit 25 for supplying power to each component of the capsule medical device 2. Further, the capsule medical device 2 is provided with a permanent magnet 26 for enabling the magnetic guidance by the above-described magnetic guidance device 3.

The capsule casing 20 is an outer cover case formed into a size introducible into the organ of the subject 100, and is realized by blocking both side opening ends of a cylindrical casing 20a with dome-shaped casings 20b and 20c. The dome-shaped casings 20b and 20c are dome-shaped optical members transparent to light having a predetermined wavelength band such as visible light. The cylindrical casing 20a is a colored casing substantially opaque to the visible light. The capsule casing 20 formed of the cylindrical casing 20a and the dome-shaped casings 20b and 20c liquid-tightly includes the imaging units 21 and 22, the radio communication unit 23, the controller 24, the power unit 25, and the permanent magnet 26, as shown in FIG. 2.

The imaging units 21 and 22 image the images in the imaging directions different from each other. Specifically, the imaging unit 21 has an illuminating unit 21a such as an LED, an optical system 21b such as a light focus lens, and a solid-state imaging device 21c such as a CMOS image sensor or a CCD. The illuminating unit 21a emits illumination light such as white light to an imaging field A1 of the solid-state imaging device 21c to illuminate the object in the imaging field A1 (such as an inner wall of the organ on an imaging field A1 side in the subject 100) through the dome-shaped casing 20b. The optical system 21b focuses reflected light from the imaging field A1 on an imaging surface of the solid-state imaging device 21c to form an object target image of the imaging field A1 on the imaging surface of the solid-state imaging device 21c. The solid-state imaging device 21c receives the reflected light from the imaging field A1 through the imaging surface, and performs a photoelectric conversion process on the received optical signal to image the object target image of the imaging field A1, that is to say, the in-vivo image of the subject 100.

The imaging unit 22 has an illuminating unit 22a such as the LED, an optical system 22b such as the light focus lens, and a solid-state imaging device 22c such as the CMOS image sensor or the CCD. The illuminating unit 22a emits illumination light such as the white light to an imaging field A2 of the solid-state imaging device 22c to illuminate the object in the field A2 (such as the inner wall of the organ on an imaging field A2 side in the subject 100) through the dome-shaped casing 20c. The optical system 22b focuses the reflected light from the imaging field A2 on an imaging surface of the solid-state imaging device 22c to form the object target image of the imaging field A2 on the imaging surface of the solid-state imaging device 22c. The solid-state imaging device 22c receives the reflected light from the imaging field A2 through the imaging surface, and performs the photoelectric conversion process on the received optical signal to image the object image of the imaging field A2, that is to say, the in-vivo image of the subject 100.

Meanwhile, when the capsule medical device 2 is a twin-lens capsule medical device for imaging forward and backward in a long axis direction as shown in FIG. 2, each optical axis of the imaging units 21 and 22 are substantially parallel to or substantially conform to a long axis 27, which is a central axis in a longitudinal direction of the capsule casing 20. In addition, directions of the imaging fields A1 and A2 of the imaging units 21 and 22, respectively, that is to say, the imaging directions of the imaging units 21 and 22, respectively, are opposite to each other.

The radio communication unit 23 is provided with an antenna 23a, and sequentially transmits by radio each image imaged by the above-described imaging units 21 and 22 to the outside through the antenna 23a. Specifically, the radio communication unit 23 obtains the image signal of the in-vivo image of the subject 100 imaged by the imaging unit 21 or 22 from the controller 24, and performs a modulation process or the like on the obtained imaging signal to generate a radio signal obtained by modulating the image signal. The radio communication unit 23 transmits such a radio signal to the external receiving device 9 (refer to FIG. 1) through the antenna 23a.

The controller 24 controls each operation of the imaging units 21 and 22 and the radio communication unit 23, which are components of the capsule medical device 2, and controls input and output of the signal among each of such components. Specifically, the controller 24 allows the solid-state imaging device 21c to image the image of the object in the imaging field A1 illuminated by the illuminating unit 21a, and allows the solid-state imaging device 22c to image the image of the object in the imaging field A2 illuminated by the illuminating unit 22a.

Also the controller 24 has a signal processing function to generate the image signal. The controller 24 performs predetermined signal processing on the in-vivo image data each time the controller 24 obtains the in-vivo image data of the imaging field A1 from the solid-state imaging device 21c to generate the image signal including the in-vivo image data of the imaging field A1. Similarly, the controller 24 performs the predetermined signal processing on the in-vivo image each time the controller 24 obtains the in-vivo image data of the imaging field A2 from the solid-state imaging device 22c to generate the image signal including the in-vivo image data of the imaging field A2. The controller 24 controls the radio communication unit 23 to sequentially transmit by radio each of the image signals to the outside in chronological order.

The power unit 25 is realized by using a capacitor unit such as a button battery or a capacitor, and a switch unit such as a magnetic switch. The power unit 25 switches on/off states of the power supply by the magnetic field externally applied, and at the time of on-state, the power unit 25 appropriately supplies power in the capacitor unit to each component (the imaging units 21 and 22, the radio communication unit 23, and the controller 24) of the capsule medical device 2. Also, the power unit 25 stops supplying power to each component of the capsule medical device 2 at the time of off-state.

The permanent magnet 26 is for enabling the magnetic guidance of the capsule medical device 2 by the above-described magnetic guidance device 3. The permanent magnet 26 is arranged in the capsule casing 20 in a state relatively fixed with respect to the above-described imaging units 21 and 22. In this case, the permanent magnet 26 is magnetized in a known direction relatively fixed with respect to the upward and downward direction of each imaging surface of the solid-state imaging devices 21c and 22c. A magnetization direction of the permanent magnet 26 is parallel to a direction perpendicular to the long axis 27 of the capsule casing 20 (that is to say, a radial direction of the capsule casing 20). Also, a central axis 26a of the permanent magnet 26 is parallel to the long axis 27 of the capsule casing 20 and deviates from a center of gravity 29 of the capsule medical device 2. That is to say, the center of gravity 29 of the capsule medical device 2 is not located on the central axis 26a of the permanent magnet 26. The central axis 26a of the permanent magnet 26 is one of rotational axes about which the permanent magnet 26 rotates following the above-described guidance magnetic field. Meanwhile, the central axis 26a of the permanent magnet 26 may conform to the long axis 27 of the capsule casing 20.

The guidance magnetic field is applied to the permanent magnet 26 thus arranged from the outside of the capsule medical device 2 by the magnetic field generator 5 shown in FIG. 1. The permanent magnet 26 moves following such a guidance magnetic field, and consequently realizes the magnetic guidance of the capsule medical device 2 by the magnetic guidance device 3. In this case, the capsule medical device 2 performs an operation to change at least one of the location, the position, and the direction in the subject 100 by an action of the permanent magnet 26. Alternatively, the capsule medical device 2 maintains a state of being stopped at a desired location in the subject 100 by the action of the permanent magnet 26.

Figure 3:
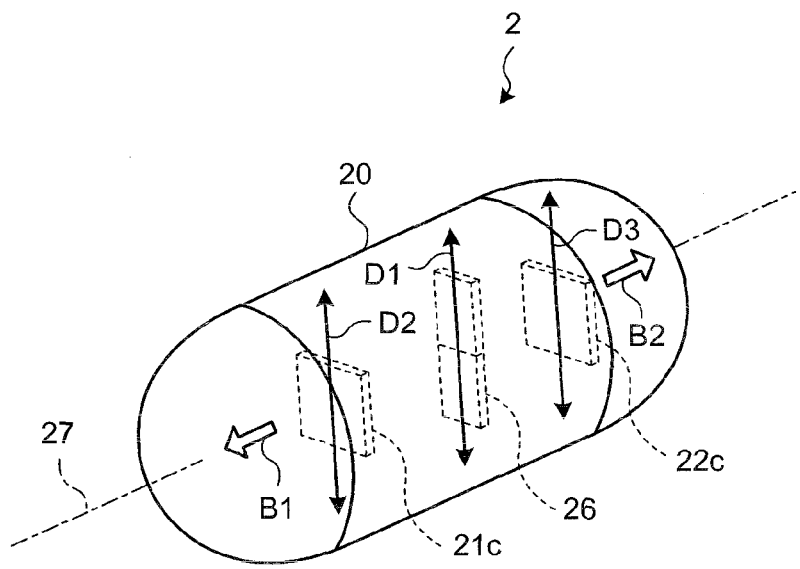
FIG. 3 is a schematic diagram showing one example of a relative arrangement state between a solid-state imaging device and a permanent magnet in the capsule medical device.

Next, relative relation between the solid-state imaging devices 21c and 22c and the permanent magnet 26 incorporated in the capsule medical device 2 is described. FIG. 3 is a schematic diagram showing one example of a relative arrangement state of the solid-state imaging devices and the permanent magnet in the capsule medical device. As shown in FIG. 3, the solid-state imaging device 21c is fixedly arranged in the capsule casing 20 in a mode in which an imaging direction B1 is oriented in the direction of the long axis 27 of the capsule medical device 2, and the solid-state imaging device 22c is fixedly arranged in the capsule casing 20 in a mode in which an imaging direction B2 is oriented in a direction opposite to the imaging direction B1.

The permanent magnet 26 is arranged in the capsule casing 20 while the permanent magnet 26 is relatively fixed with respect to the imaging units 21 and 22 as described above. In this case, the permanent magnet 26 is magnetized in the radial direction of the capsule casing 20 and in a known direction relatively fixed with respect to upward and downward directions and D3 of each imaging surface of the solid-state imaging devices 21 and 22c respectively shown in FIG. 3. That is to say, a magnetization direction D1 of the permanent magnet 26 is a known direction relatively fixed with respect to the upward and downward direction D2 of the imaging surface of the solid-state imaging device 21c and a known direction relatively fixed with respect to the upward and downward direction D3 of the imaging surface of the solid-state imaging device 22c. Specifically, in the capsule medical device 2 according to the first embodiment, the magnetization direction D1 of the permanent magnet 26 is parallel to the upward and downward directions D2 and D3 of each imaging surface of the solid-state imaging devices 21c and 22c respectively as shown in FIG. 3.

Figure 4:
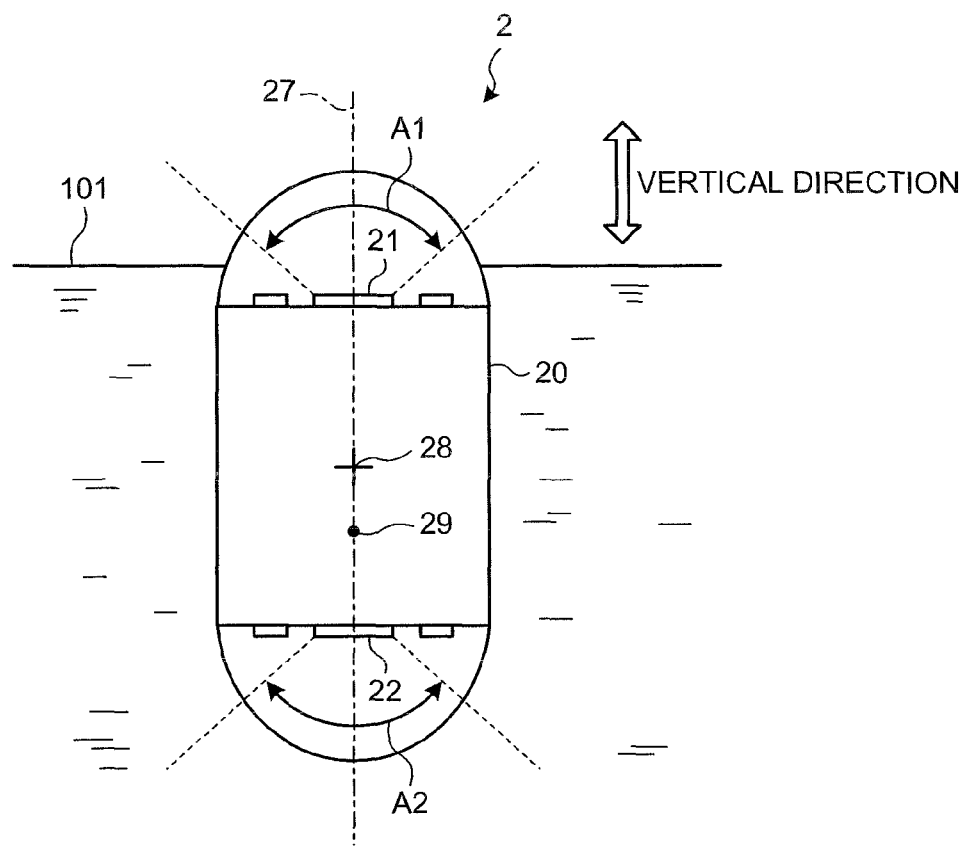
FIG. 4 is a schematic diagram showing one example of a state in which the capsule medical device floats in liquid in a subject.
Figure 5:
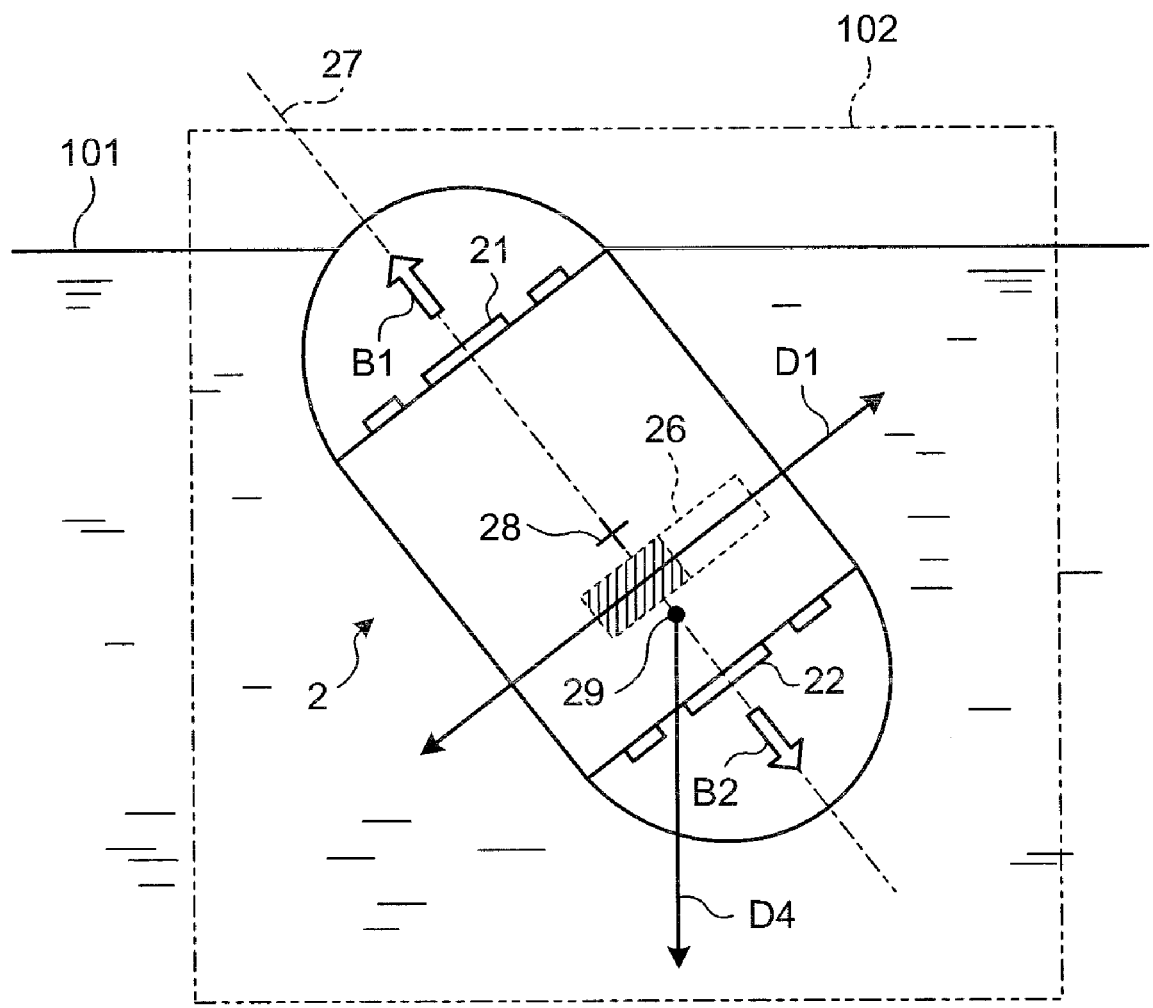
FIG. 5 is a schematic diagram showing one example of a specific state, which the capsule medical device maintains in the liquid in the subject.

Next, the center of gravity 29 of the capsule medical device 2 is described. FIG. 4 is a schematic diagram showing one example of a state in which the capsule medical device floats in the liquid in the subject. FIG. 5 is a schematic diagram showing one example of a specific state, which the capsule medical device maintains in the liquid in the subject.

The capsule medical device 2 has the center of gravity 29 at a location deviated from a geometric center 28 of the capsule casing 20 (a location deviated in a direction parallel to a plane parallel to the magnetization direction D1 of the permanent magnet 26 and the imaging directions B1 and B2 and different from the magnetization direction D1 of the permanent magnet 26, in detail) as shown in the above-described FIG. 2. Specifically, the center of gravity 29 of the capsule medical device 2 is set to a location on the long axis 27 and deviated from the geometric center 28 of the capsule casing 20 to an imaging unit 22 side, by adjusting arrangement of each component of the capsule medical device 2 such as the power unit 25 and the permanent magnet 26.

The capsule medical device 2 of which center of gravity 29 is thus set maintains upright position in the liquid 101 as shown in FIG. 4, when the above-described guidance magnetic field is not applied. Meanwhile, the upright position herein used is intended to mean the position in which the long axis 27 (a straight line connecting the geometric center 28 and the center of gravity 29) of the capsule casing 20 and the vertical direction are substantially parallel to each other. With such a upright position, the capsule medical device 2 turns the imaging field A1 of the imaging unit 21 in a vertically upward direction and turns the imaging field A2 of the imaging unit 22 in a vertically downward direction.

On the other hand, the capsule medical device 2 maintains the specific state as shown in FIG. 5 in the liquid 101 when the above-described guidance magnetic field is applied. Specifically, the capsule medical device 2 maintains the specific state in which a vertical plane 102 including a direction of center of gravity D4 is parallel to each imaging direction B1 and B2 of the imaging units 21 and 22 respectively, and the magnetization direction D1 of the permanent magnet 26. Such a specific state of the capsule medical device 2 is maintained in the liquid 101 even when the magnetic field direction or the magnetic field strength of the guidance magnetic field to be applied to the permanent magnet 26 is changed. That is to say, the above-described magnetic guidance device 3 (refer to FIG. 1) applies the guidance magnetic field to the permanent magnet 26 in the capsule medical device 2 to magnetically guide the capsule medical device 2 in the liquid 101 while maintaining such a specific state.

Meanwhile, the liquid 101 is liquid harmless to human, such as water or normal saline solution and a specific gravity of the liquid 101 is larger than that of the capsule medical device 2. That is to say, the capsule medical device 2 may float in the liquid 101. An appropriate amount of the liquid 101 is introduced into the organ of the subject 100 to float the capsule medical device 2 in the organ of the subject 100.

Figure 6:
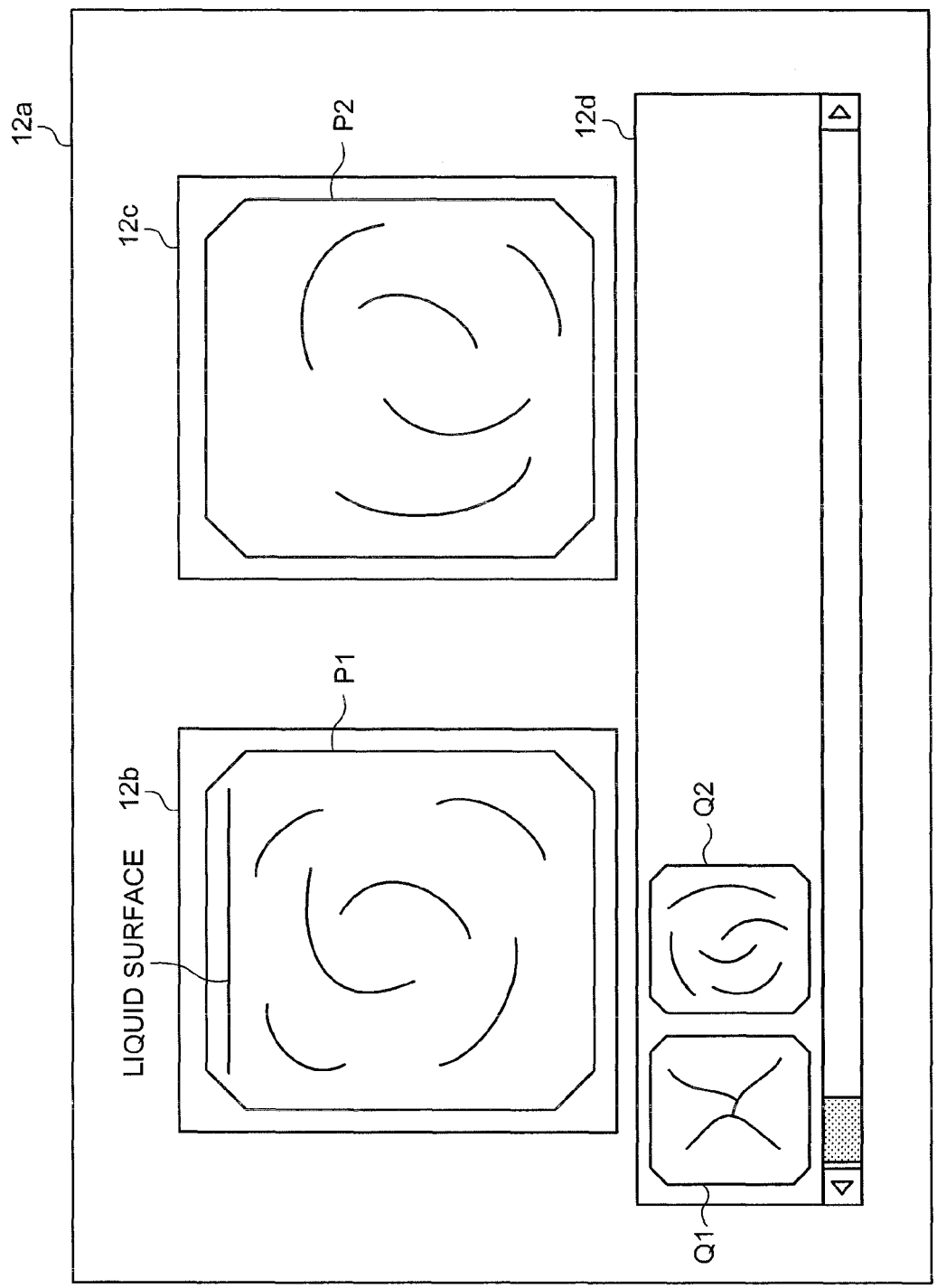
FIG. 6 is a schematic diagram showing one example of a display mode of an image display device according to the first embodiment of the present invention.

Next, a display of the in-vivo image of the subject 100 by the image display device 10 is described. FIG. 6 is a schematic diagram showing one example of a display mode of the image display device according to the first embodiment of the present invention. The image display device 10 displays the in-vivo image of the subject 100 by the capsule medical device 2 in the display mode in which the upward and downward direction of the object in the in-vivo image associated with the magnetic guidance of the capsule medical device 2 conforms with the upward and downward direction of the display screen, as described above. In this case, the display unit 12 of the image display device 10 displays a window 12a shown in FIG. 6 based on the control of the controller 14 to display each in-vivo image of the subject 100 in the window 12a.

Specifically, as shown in FIG. 6, the window 12a includes two main-image display areas 12b and 12c and a scrollable subimage display area 12d. The display unit 12 displays an i-n-vivo image P1 of the subject 100 imaged by the imaging unit 21 of the capsule medical device 2 on the main-image display area 12b. In this case, the display unit 12 displays the in-vivo image P1 by conforming the direction of intersection line of the imaging surface of the solid-state imaging device 21c and the vertical plane in the in-vivo image P1 to the upward and downward direction of the main-image display area 12b. On the other hand, the display unit 12 displays an in-vivo image P2 of the subject 100 imaged by the imaging unit 22 of the capsule medical device 2 on the main-image display area 12c. In this case, the display unit 12 displays the in-vivo image P2 by conforming the direction of intersection line of the imaging surface of the solid-state imaging device 22c and the vertical plane in the in-vivo image P2 to the upward and downward direction of the main-image display area 12c. The display unit 12 sequentially displays the in-vivo images P1 and P2 in such a display mode as the moving image on the main-image display areas 12b and 12c respectively in real time, and switches the moving image display of the in-vivo images P1 and P2 to the still image display based on the instruction information input by the input unit 11. Thereafter, the display unit 12 switches the still image display of the in-vivo images P1 and P2 to the moving image display based on the instruction information input by the input unit 11.

On the other hand, when a desired in-vivo image is selected or marked from the in-vivo image group of the subject 100 imaged by the capsule medical device 2, by the input operation of the input unit 11 by the user, the display unit 12 sequentially additionally displays the reduced image of such a desired in-vivo image on the subimage display area 12d each time. Here, such a desired in-vivo image is selected or marked from the in-vivo images P1 sequentially displayed on the main-image display area 12b or the in-vivo images P2 sequentially displayed on the main-image display area 12c, by a click operation of the input unit 11. Meanwhile, in FIG. 6, the display unit 12 displays thumbnail images Q1 and Q2 on the subimage display area 12d as one example of the reduced image of such a desired in-vivo image.

Figure 7:
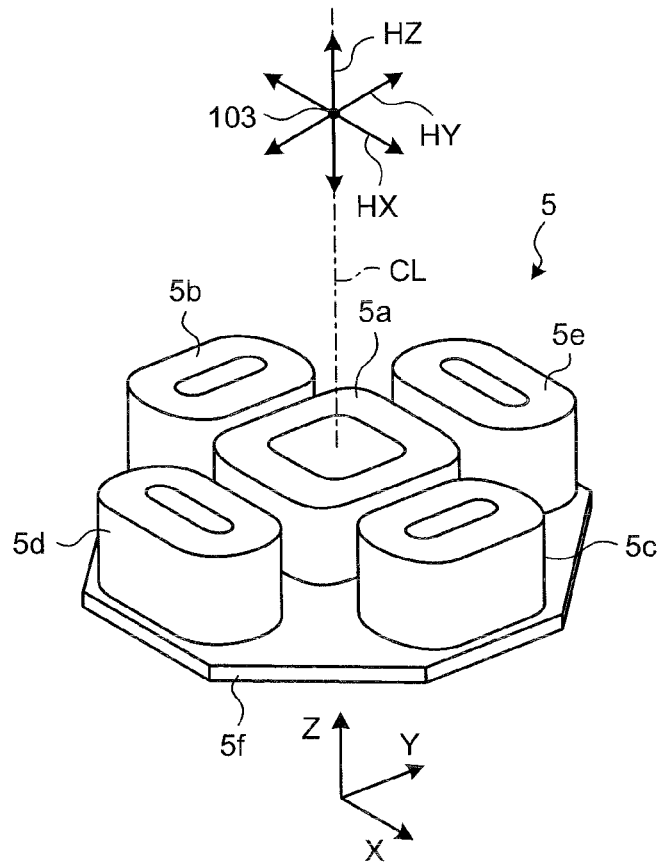
FIG. 7 is a schematic diagram showing one configuration example of a magnetic field generator, which is a part of the magnetic guidance device.
Figure 8:
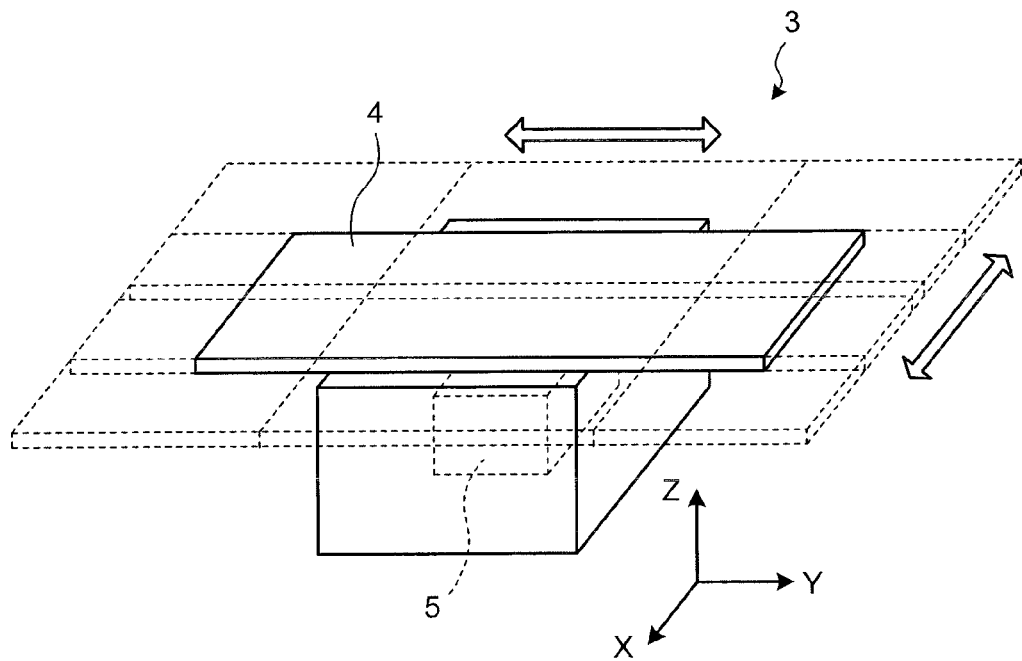
FIG. 8 is a schematic diagram showing a drive state of a movable bed, which is a part of the magnetic guidance device.

Next, the magnetic guidance device 3 for magnetically guiding the capsule medical device 2 in the subject 100 is described. FIG. 7 is a schematic diagram showing one configuration example of the magnetic field generator, which is a portion of the magnetic guidance device. FIG. 8 is a schematic diagram showing a drive state of the movable bed, which is a portion of the magnetic guidance device.

The magnetic guidance device 3 is provided with the magnetic field generator 5 for generating the guidance magnetic field, as described above. The magnetic generator 5 is as shown in FIG. 7 provided with a z-axis coil 5a for generating the magnetic field in a z-axis direction of an absolute coordinate system, a pair of x-axis coils 5b and 5c for generating the magnetic field in an x-axis direction of the absolute coordinate system, and a pair of y-axis coils 5d and 5e for generating the magnetic field in an y-axis direction of the absolute coordinate system.

The z-axis coil 5a is fixedly arranged on a substantially central portion of a table 5f to generate a magnetic field HZ in the z-axis direction of the absolute coordinate system based on the alternating current from the above-described power unit 7. A pair of x-axis coils 5b and 5c are fixedly arranged on the table 5f along the x-axis of the absolute coordinate system so as to interpose the z-axis coil 5a to generate a magnetic field HX in the x-axis direction of the absolute coordinate system based on the alternating current from the above-described power unit 7. A pair of y-axis coils 5d and 5e are fixedly arranged on the table 5f along the y-axis of the absolute coordinate system so as to interpose the z-axis coil 5a to generate a magnetic field HY in the y-axis direction of the absolute coordinate system based on the alternating current from the above-described power unit 7.

Here, the absolute coordinate system is a three-axis orthogonal coordinate system in which the z-axis in the vertical direction and the x-axis and the y-axis in the horizontal direction are at right angles to one another. The z-axis of the absolute coordinate system conforms to a central axis CL of the z-axis coil 5a. The z-axis coil 5a generates the magnetic field HZ in the vertical direction on the central axis CL, a pair of x-axis coils 5b and 5c generate the magnetic field HX in the x-axis direction on the central axis CL, and a pair of y-axis coils 5d and 5e generate the magnetic field HY in the y-axis direction on the central axis CL. Each of the magnetic fields HZ, HX and HY are combined at an intersection 103 of the central axis CL and an optional plane to generate the guidance magnetic field for magnetically guiding the capsule medical device 2. The guidance magnetic field thus generated has a peak to restrain the location of the capsule medical device 2 in the horizontal direction in the liquid 101 in the vicinity of the central axis CL.

The magnetic field generator 5 may magnetically capture the capsule medical device 2 in the liquid 101 in the vicinity of the z-axis (that is to say, the central axis CL) of the absolute coordinate system by applying the guidance magnetic field obtained by combining each of the magnetic fields HZ, HX, and HY to the permanent magnet 26 in the capsule medical device 2. On the other hand, the magnetic field generator 5 may magnetically guide the capsule medical device 2 in the liquid 101 in the vertical direction by changing the magnetic field strength of the magnetic field HZ out of such guidance magnetic fields. Also, the magnetic field generator 5 may change at least one of the position and the direction of the capsule medical device 2 in the liquid 101 by appropriately changing the magnetic field strength of the magnetic fields HZ, HX, and HY composing such a guidance magnetic field.

On the other hand, the magnetic guidance device 3 is provided with the movable bed 4 capable of parallelly moving the table portion thereof by the above-described drive unit 4a. The above-described absolute coordinate system of the bed 4 is defined as shown in FIG. 8, and the table portion can be horizontally moved by parallelly moving the table portion in at least one of the x-axis direction and the y-axis direction of the absolute coordinate system.

Here, the bed 4 supports the subject 100 including the capsule medical device 2 in the liquid 101 in the organ (refer to FIG. 1) on the table, and moves the table portion in a state of supporting the subject 100 in a horizontal direction based on the control of the above-described drive controller 6. Thereby, the bed 4 changes the relative location of the subject 100 with respect to the magnetic field generator 5, which magnetically captures the capsule medical device 2. The magnetic guidance device 3 magnetically guides the capsule medical device 2 in the liquid 101 in the subject 100 in the horizontal direction by combining a magnetic acquisition action of the capsule medical device 2 by the magnetic field generator 5 and a change action of the relative location between the magnetic field generator 5 and the subject 100 by the bed 4.

Figure 9:
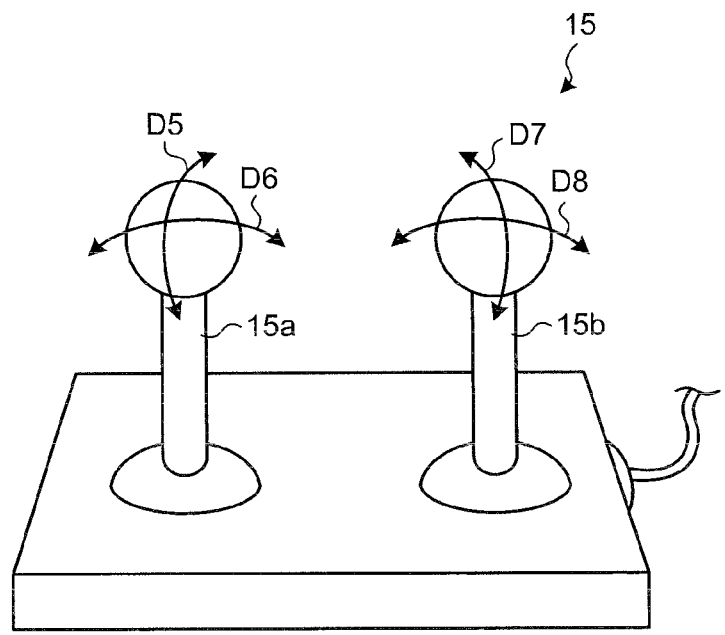
FIG. 9 is a schematic diagram showing one example of an operation input unit according to the first embodiment of the present invention.
Figure 10:
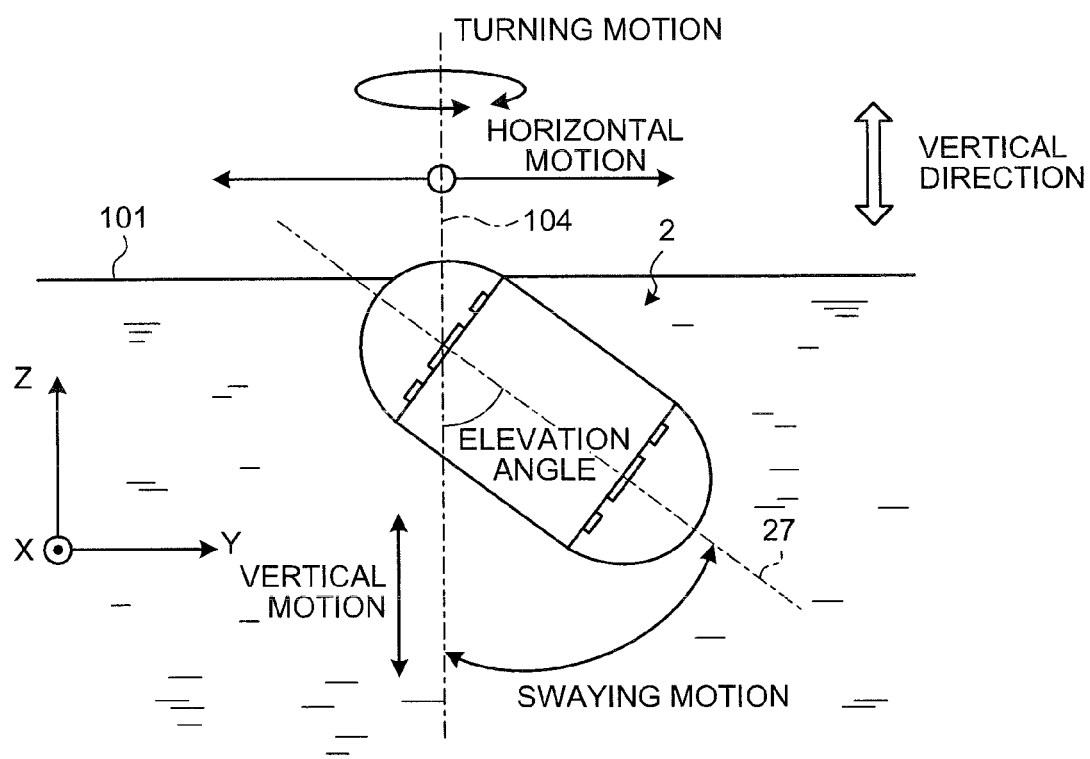
FIG. 10 is a schematic diagram for illustrating magnetic guidance of the capsule medical device operable by an operation input unit.

Next, the operation input unit 15 for operating the magnetic guidance of the capsule medical device 2 is described. FIG. 9 is a schematic view showing one example of the operation input unit according to the first embodiment of the present invention. FIG. 10 is a schematic diagram for illustrating the magnetic guidance of the capsule medical device operable by the operation input unit. As shown in FIG. 9, the operation input unit 15 is provided with two joysticks 15a and 15b for three-dimensionally operating the magnetic guidance of the capsule medical device 2 by the magnetic guidance device 3.

The joystick 15a is for operating the magnetic guidance of the capsule medical device 2 in the horizontal direction, and a tilt operation is possible in an upward and downward direction D5 and a right and left direction D6 of a two-axis orthogonal coordinate system set in advance. A tilt direction of the joystick 15a corresponds to a horizontal motion direction of the capsule medical device 2 in the subject 100, and a tilt amount of the joystick 15a corresponds to a horizontal motion speed of the capsule medical device 2 in the subject 100. The operation input unit 15 determines the horizontal motion direction of the capsule medical device 2 in the x-axis direction of the absolute coordinate system in response to the tilt operation of the joystick 15a in the upward and downward direction D5, and determines the horizontal motion speed of the capsule medical device 2 in the x-axis direction in response to a tilt operation amount in the upward and downward direction D5. In this case, the operation input unit 15 inputs the operation information to specify the x-axis direction as the horizontal motion direction of the capsule medical device 2 and to specify the horizontal motion speed of the capsule medical device 2 in the x-axis direction to the controller 19 of the control device 16. On the other hand, the operation input unit 15 determines the horizontal motion direction of the capsule medical device 2 in the y-axis direction of the absolute coordinate system in response to the tilt operation of the joystick 15a in the right and left direction D6, and determines the horizontal motion speed of the capsule medical device 2 in the y-axis direction in response to the tilt operation amount in the right and left direction D6. In this case, the operation input unit 15 inputs the operation information to specify the y-axis direction as the horizontal motion direction of the capsule medical device 2 and to specify the horizontal motion speed of the capsule medical device 2 in the y-axis direction to the controller 19 of the control device 16.

The joystick 15b is for operating the magnetic guidance of the capsule medical device 2 about the horizontal axis and the magnetic guidance of the capsule medical device about the vertical axis, and the tilt operation is possible in an upward and downward direction D7 and a right and left direction D8 of the two-axis orthogonal coordinate system set in advance. The upward and downward direction D7, which is one of the tilt directions of the joystick 15b, corresponds to a direction of a rotational motion of the capsule medical device 2 around the horizontal axis (hereinafter, referred to as a swaying motion) in the subject 100, and the tilt amount of the joystick 15b in the upward and downward direction D7 corresponds to a swaying motion speed of the capsule medical device 2. The operation input unit 15 determines a swaying motion direction (clockwise or counterclockwise) of the capsule medical device 2 in response to the tilt operation of the joystick 15b in the upward and downward direction D7, and determines the swaying motion speed of the capsule medical device 2 in response to the tilt operation amount in the upward and downward direction D7. In this case, the operation input unit 15 inputs the operation information to specify the swaying motion direction and the swaying motion speed of the capsule medical device 2 to the controller 19 of the control device 16. On the other hand, the right and left direction D8, which is one of the tilt directions of the joystick 15b, corresponds to a direction of the rotational motion of the capsule medical device 2 about the vertical axis (hereinafter, referred to as a turning motion) in the subject 100, and the tilt amount of the joystick 15b in the right and left direction D8 corresponds to a turning motion speed of the capsule medical device 2. The operation input unit 15 determines a turning motion direction (clockwise or counterclockwise) of the capsule medical device 2 in response to the tilt operation of the joystick 15b in the right and left direction D8, and determines the turning motion speed of the capsule medical device 2 in response to the tilt operation amount in the right and left direction D8. In this case, the operation input unit 15 inputs the operation information to specify the turning motion direction and the turning motion speed of the capsule medical device 2 to the controller 19 of the control device 16.

In addition, when the tilt operation of the joystick 15a in the upward and downward direction D5 and the tilt operation of the joystick 15b in the upward and downward direction D7 are simultaneously performed, the operation input unit 15 inputs the operation information to specify a vertical motion direction and a vertical motion speed of the capsule medical device 2 to the controller 19 of the control device 16. Specifically, when the joysticks 15a and 15b are simultaneously operated to tilt to a back side of the operation input unit 15 seen from the front, the operation input unit 15 inputs the operation information to specify vertical upward as the vertical motion direction of the capsule medical device 2 and to specify the vertical motion speed of the capsule medical device 2 in a vertical upward direction to the controller 19 of the control device 16. On the other hand, when the joysticks 15a and 15b are simultaneously operated to tilt to a front side of the operation input unit 15 seen from the front, the operation input unit 15 inputs the operation information to specify vertically downward as the vertical motion direction of the capsule medical device 2 and to specify the vertical motion speed of the capsule medical device 2 in a vertically downward direction to the controller 19 of the control device 16.

The controller 19 of the above-described control device 16 controls the magnetic guidance device 3 to perform the magnetic guidance of the capsule medical device 2 according to the magnetic guidance direction and the magnetic guidance speed specified by the operation information from the operation input unit 15. The capsule medical device 2 performs various motions according to the magnetic guidance by the magnetic guidance device 3 in the liquid 101 in the subject 100. Specifically, as shown in FIG. 10, the capsule medical device 2 in the liquid 101 performs the horizontal motion to horizontally move in the x-axis direction of the absolute coordinate system in response to the tilt operation of the above-described joystick 15a in the upward and downward direction D5. Also, the capsule medical device 2 in the liquid 101 performs the horizontal motion to horizontally move in the y-axis direction of the absolute coordinate system in response to the tilt operation of the above-described joystick 15a in the right and left direction D6.

On the other hand, the capsule medical device 2 in the liquid 101 performs the swaying motion in response to the tilt operation of the above-described joystick 15b in the upward and downward direction D7, thereby changing an elevation angle, which is an angle between the long axis 27 of the capsule medical device 2 and the vertical axis 104. Also, the capsule medical device 2 in the liquid 101 performs the turning motion in response to the tilt operation of the above-described joystick 15b in the right and left direction D8, thereby changing a direction angle, which is the angle between a horizontal component of the long axis 27 of the capsule medical device 2 and a reference axis (x-axis or y-axis, for example) in the horizontal direction. On the other hand, the capsule medical device 2 in the liquid 101 performs a vertical motion moving upward or downward in the z-axis direction (that is to say, the vertical direction) of the absolute coordinate system in response to the simultaneous tilt operation of the above-described joysticks 15a and 15b.

Meanwhile, the elevation angle of the capsule medical device 2 is a physical amount indicating the position of the capsule medical device 2 in the liquid 101, and changes according to the change in position of the capsule medical device 2. Also, the direction angle of the capsule medical device 2 is the physical amount indicating the direction of the capsule medical device 2 in the liquid 101, and changes according to the change in direction of the capsule medical device 2.

Figure 11:
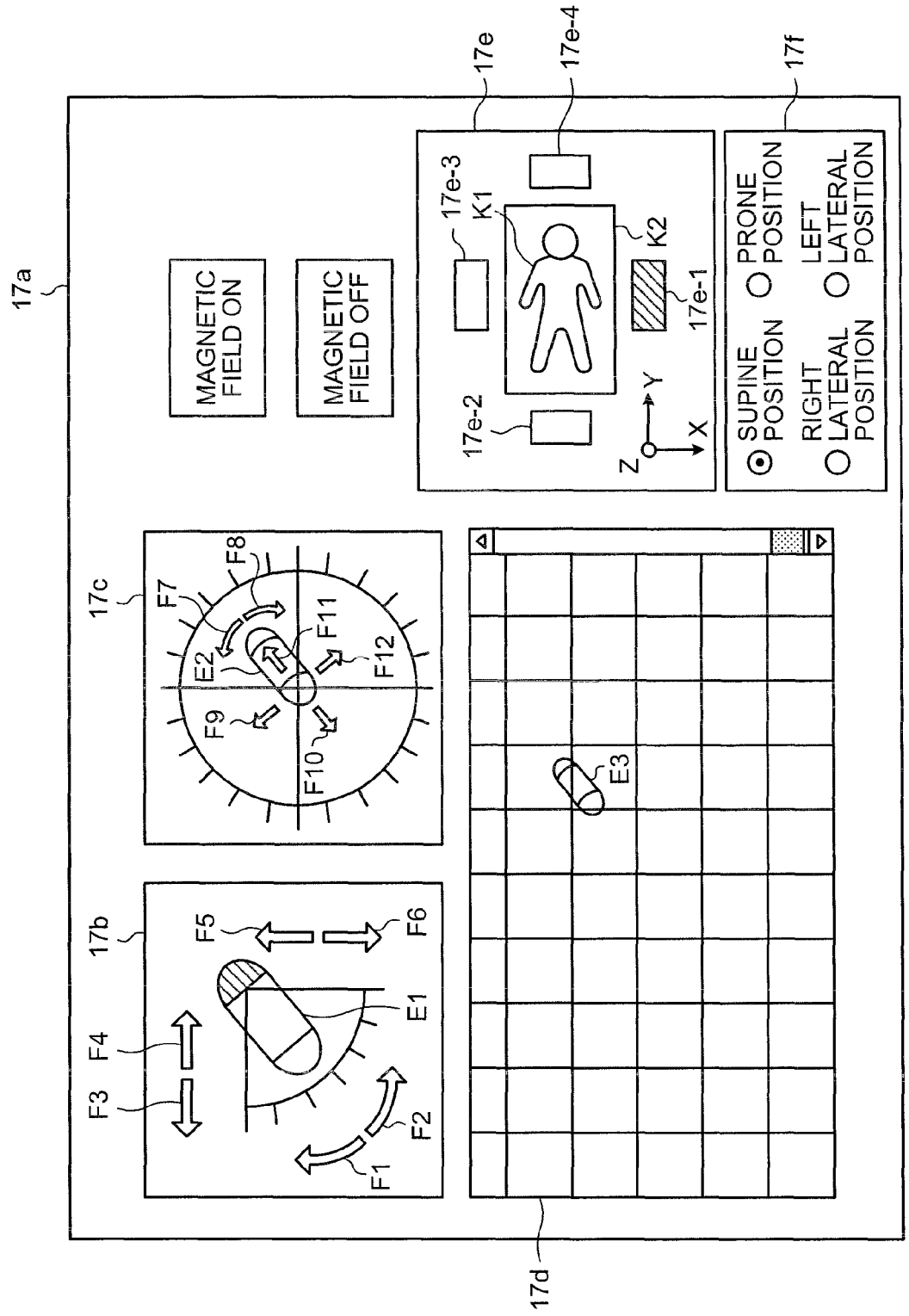
FIG. 11 is a schematic diagram showing one display mode example of a display unit of a control device.

Next, information display by the display unit 17 of the control device 16 is described. FIG. 11 is a schematic diagram showing one display mode example of the display unit of the control device. The display unit 17 of the control device 16 displays various pieces of information useful in operation of the magnetic guidance of the capsule medical device 2, such as the information indicating the location, the position, and the direction of the capsule medical device 2 in the subject 100, which is the magnetic guidance target, the relative location information of the operation input unit 15 with respect to the bed 4, the body posture information of the subject 100 on the bed 4, and the like. In this case, the display unit 17 displays a window 17a as shown in FIG. 11 to display the various pieces of information in the window 17a.

Specifically, as shown in FIG. 11, the window 17a includes an elevation angle information display area 17b for displaying elevation angle information of the capsule medical device 2, a direction angle information display area 17c for displaying direction angle information of the capsule medical device 2, and a location Information display area 17d for displaying location information of the capsule medical device 2. Also, the window 17a includes an operation table location setting unit 17e, which is a graphical user interface (GUI) for setting the relative location of the operation input unit 15 with respect to the bed 4, and a body posture setting unit 17f, which is the GUI for setting the body posture of the subject 100 on the bed 4.

The display unit 17 displays the elevation angle information of the capsule medical device 2 on the elevation angle information display area 17b as the information to indicate the position of the capsule medical device 2 in the subject 100. Specifically, the image processor 19a of the control device 16 generates a capsule pattern image E1 schematically showing the capsule medical device 2 seen from the radial direction of the capsule casing 20 and the horizontal direction. Also, the image processor 19a calculates the elevation angle of the capsule medical device 2 based on the information of the guidance magnetic field (such as the magnetic field strength and the magnetic field direction) applied by the magnetic field generator 5 to the capsule medical device 2, the physical information (such as the mass, the shape, the location of center of gravity, and the magnetic moment) of the capsule medical device 2, and the density information of the liquid 101. The image processor 19a rotates the capsule pattern image E1 according to the calculated elevation angle. The controller 19 controls the display unit 17 to display an elevation angle scale from the vertical axis to the horizontal axis in the elevation angle information display area 17b, and further controls the display unit 17 to display the rotated capsule pattern image E1 along the elevation angle scale. The display unit 17 displays the elevation angle scale in the elevation angle information display area 17b based on the control of the controller 19, and displays the capsule pattern image E1 so as to indicate a portion of the scale conforming with the elevation angle of the capsule medical device 2 of the elevation angle scale. Thereby, the display unit 17 displays the elevation angle information of the capsule medical device 2.

Also, the display unit 17 displays the capsule pattern image E1 in the display mode to indicate the operation target direction based on the control of the controller 19. Here, the operation target direction is the imaging direction of the operation target image, which becomes the target of the operation when operating the magnetic guidance of the capsule medical device 2. Also, the operation target image is either one of the in-vivo images P1 and P2 displayed on the above-described image display device 10, which is referred to when operating the magnetic guidance of the capsule medical device 2. That is to say, the operation target image is the in-vivo image imaged by either of the imaging units 21 and 22 incorporated in the capsule medical device 2. The image processor 19a marks a portion of the capsule pattern image E1 corresponding to an arranged portion of the imaging unit (one of the imaging units 21 and 22) of such an operation target image. The controller 19 controls the display unit 17 to display the marked capsule pattern image E1. The display unit 17 displays the capsule pattern image E1, a portion of which (shadowed portion) is marked as shown in FIG. 11, on the elevation angle information display area 17b based on the control of the controller 19, thereby clearly showing the operation target direction at the time of the magnetic guidance of the capsule medical device 2.

Meanwhile, in the capsule medical device 2 according to the first embodiment, the imaging directions B1 and B2 of the imaging units 21 and 22 respectively, are in the same direction as the long axis 27 of the capsule medical device 2. Therefore, the elevation angle of the capsule medical device 2 in the liquid 101 is the angle between the imaging direction (one of the imaging directions B1 and B2 of the imaging units 21 and 22, respectively) of the imaging unit of such an operation target image and the vertical axis.

On the other hand, the display unit 17 displays the direction angle information of the capsule medical device 2 in the direction angle information display area 17c as the information indicating the direction of the capsule medical device 2 in the subject 100. Specifically, the image processor 19a generates a capsule pattern image E2 schematically showing the capsule medical device 2 in the subject 100 seen from vertically above. Also, the image processor 19a calculates the direction angle of the capsule medical device 2 based on the information of the guidance magnetic field to be applied by the magnetic field generator 5 to the capsule medical device 2 (the magnetic field direction of the horizontal component of the guidance magnetic field, in detail). The image processor 19a rotates the capsule pattern image E2 according to the calculated direction angle. The controller 19 controls the display unit 17 to display a circular direction angle scale as shown in FIG. 11 in the direction angle information display area 17c, and further, controls the display unit 17 to display the rotated capsule pattern image E2 along the direction angle scale. The display unit 17 displays the direction angle scale in the direction angle information display area 17c based on the control of the controller 19, and displays the capsule pattern image E2 so as to indicate a portion of the scale conforming with the direction angle of the capsule medical device 2 of the direction angle scale. Thereby, the display unit 17 displays the direction angle information of the capsule medical device 2.

Also, the display unit 17 appropriately displays arrow information F1 to F12 indicating the magnetic guidance direction of the capsule medical device 2 according to the magnetic guidance direction in at least one of the elevation angle information display area 17b and direction angle information display area 17c when the magnetic guidance of the capsule medical device 2 is carried out.

Specifically, the controller 19 controls the magnetic guidance of the capsule medical device 2 by the magnetic guidance device 3 based on the operation information input by the operation input unit 15, and controls the display unit 17 to display the arrow information (any of the arrow information F1 to F12) indicating the magnetic guidance direction specified by the operation information. The display unit 17 displays the arrow information conforming to the swaying motion direction of the capsule medical device 2 out of the arrow information F1 and F2 in the elevation angle information display area 17b when the magnetic guidance direction specified by the operation information is about the horizontal axis. The display unit 17 displays the arrow information conforming with the horizontal motion direction of the capsule medical device 2 among the arrow information F3, F4 and F9 to F12 in the elevation angle information display area 17b or the direction angle information display area 17c when the magnetic guidance direction specified by the operation information is in the horizontal direction. The display unit 17 displays the arrow information conforming to the vertical motion direction of the capsule medical device 2 out of the arrow information F5 and F6 in the elevation angle information display area 17b when the magnetic guidance direction specified by the operation information is in the vertical direction. The display unit 17 displays the arrow information conforming to the turning motion direction of the capsule medical device 2 out of the arrow information F7 and F8 in the direction angle information display area 17c when the magnetic guidance direction specified by the operation information is around the vertical axis.

On the other hand, the display unit 17 displays the location information of the capsule medical device 2 in the subject 100 in the location information display area 17d. Specifically, the image processor 19a generates a capsule pattern image E3 schematically showing the capsule medical device 2 in the subject 100 seen from vertically above. Also, the image processor 19a calculates the location information of the capsule medical device 2 in an xy-plane of the absolute coordinate system based on the relative location of the magnetic field generator 5 with respect to the table portion of the bed 4. Meanwhile, the calculated location information is relative location information of the capsule medical device 2 with respect to the subject 100 on the bed 4. The controller 19 controls the display unit 17 to display a grid coordinate scale as shown in FIG. 11 in the location information display area 17d, and further controls the display unit 17 to display the capsule pattern image E3 on a portion of the coordinate scale conforming with the calculated location information. The display unit 17 displays the grid coordinate scale in the location information display area 17d based on the control of the controller 19, and displays the capsule pattern image E3 on the portion of the scale conforming with the location information of the capsule medical device 2 of the coordinate scale. Thereby, the display unit 17 displays the location information of the capsule medical device 2 in the subject 100.

Meanwhile, the capsule pattern images E1 to E3 operate in conjunction with each other in association with the magnetic guidance of the capsule medical device 2. That is to say, the capsule pattern image E1 sways following the swaying motion of the capsule medical device 2. The capsule pattern images E2 and E3 change the position thereof following the swaying motion of the capsule pattern image E1. Also, the capsule pattern images E2 and E3 turn following the turning motion of the capsule medical device 2. In this case, the capsule pattern images E2 and E3 are in display modes similar to each other.

The operation table location setting unit 17e is the GUI for setting the relative location of the operation input unit 15 with respect to the bed 4, as described above. The display unit 17 displays a subject pattern image K1 for schematically showing the subject 100 and a bed pattern image K2 schematically showing the bed 4 in the operation table location setting unit 17e based on the control of the controller 19. In this case, the display unit 17 displays the subject pattern image K1 so as to overlap with the bed pattern image K2 to display a state in which the subject 100 is placed on the bed 4.

Also, the operation table location setting unit 17e includes input boxes 17e-1 to 17e-4 on four points around the bed pattern image K2 as shown in FIG. 11. The input box 17e-1 is the GUI for setting the location of the operation input unit 15 on an x-axis positive direction side of the circumference of the bed 4, and is formed under the bed pattern image K2 seen from the front. The input box 17e-2 is the GUI for setting the location of the operation input unit 15 on a y-axis negative direction side of the circumference of the bed 4, and is formed on a left side of the bed pattern image K2 seen from the front. The input box 17e-3 is the GUI for setting the location of the operation input unit 15 on an x-axis negative direction side of the circumference of the bed 4, and is formed above the bed pattern image K2 seen from the front. The input box 17e-4 is the GUI for setting the location of the operation input unit 15 on a y-axis positive direction side of the circumference of the bed 4, and is formed on a right side of the bed pattern image K2 seen from the front.

The operation input unit 15 inputs location specifying information to specify the x-axis positive direction side of the bed 4 as the location of the operation input unit 15 to the controller 19 by clicking the input box 17e-1. The operation input unit 15 inputs the location specifying information to specify the y-axis negative direction side of the bed 4 as the location of the operation input unit 15 to the controller 19 by clicking the input box 17e-2. The operation input unit 15 inputs the location specifying information to specify the x-axis negative direction side of the bed 4 as the location of the operation input unit 15 to the controller 19 by clicking the input box 17e-3. The operation input unit 15 inputs the location specifying information to specify the y-axis positive direction side of the bed 4 as the location of the operation input unit 15 to the controller 19 by clicking the input box 17e-4.

The display unit 17 makes the display mode such as a color of the input box finally clicked by the operation input unit 15 among the input boxes 17e-1 to 17e-4 different from remaining input boxes. Meanwhile, in FIG. 11, the input box 17e-1 is the one finally clicked by the operation input unit 15.

The controller 19 converts the horizontal motion direction of the capsule medical device 2 specified by the above-described operation information to the horizontal motion direction according to a direction from the operation input unit 5 toward the subject 100 (that is to say, a point of view direction of the user) to control the magnetic guidance of the capsule medical device 2 based on the location specifying information from the operation input unit 15. Also, the controller 19 controls the display unit 17 to change the directions of the capsule pattern images E2 and E3 according to the relative location of the operation input unit 15 specified by the location specifying information from the operation input unit 15. The display unit 17 changes the display directions of the capsule pattern images E2 and E3 by 90 degrees, for example, based on the control of the controller 19.

The body posture setting unit 17f is the GUI for setting the body posture of the subject 100 on the bed 4 as described above. Specifically, the body posture setting unit 17f includes a body posture setting menu (such as the setting menu of a supine location, a prone location, a right lateral location, and a left lateral location) of the subject 100 as shown in FIG. 11. The operation input unit 15 clicks any body posture of the body posture setting menu of the body posture setting unit 17f to input body posture specifying information to specify the clicked body posture to the controller 19. The image processor 19a generates the subject pattern image K1 showing the body posture specified by the body posture specifying information. The controller 19 controls the display unit 17 to display the subject pattern image K1. The display unit 17 displays the subject pattern image K1 showing the body posture specified by the body posture specifying information on the operation table location setting unit 17e based on the control of the controller 19. Also, the display unit 17 displays the mark in a setting column of the body posture corresponding to the body posture specifying information (that is to say the body posture clicked by the operation inputting unit 15) of the body posture setting menu of the body posture setting unit 17f. Meanwhile, in FIG. 11, the supine location is selected by the click operation of the operation input unit 15 from the body postures in the body posture setting menu of the body posture setting unit 17f.

Meanwhile, the display unit 17 appropriately displays information indicating that the magnetic field generator 5 is in a state of generating the guidance magnetic field (magnetic field on-state) and information indicating that the magnetic field generator 5 is in a state of stopping generating the guidance magnetic field (magnetic field off-state), in addition to the elevation angle information, the direction angle information, and the location information of the above-described capsule medical device 2, in the window 17a according to a generation state of the guidance magnetic field.

Figure 12:
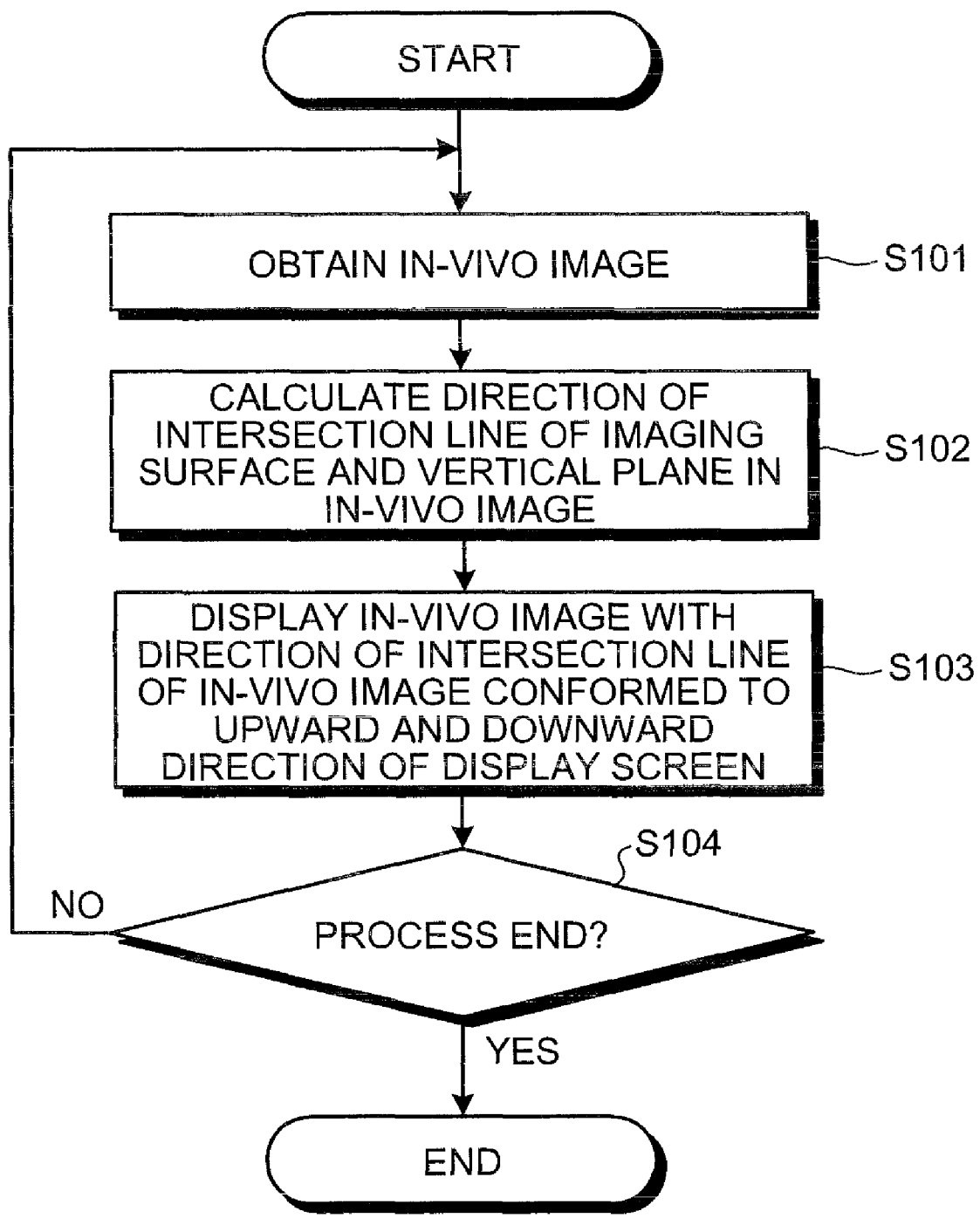
FIG. 12 is a flowchart showing one example of a procedure of the image display device according to the first embodiment of the present invention.
Figure 13:
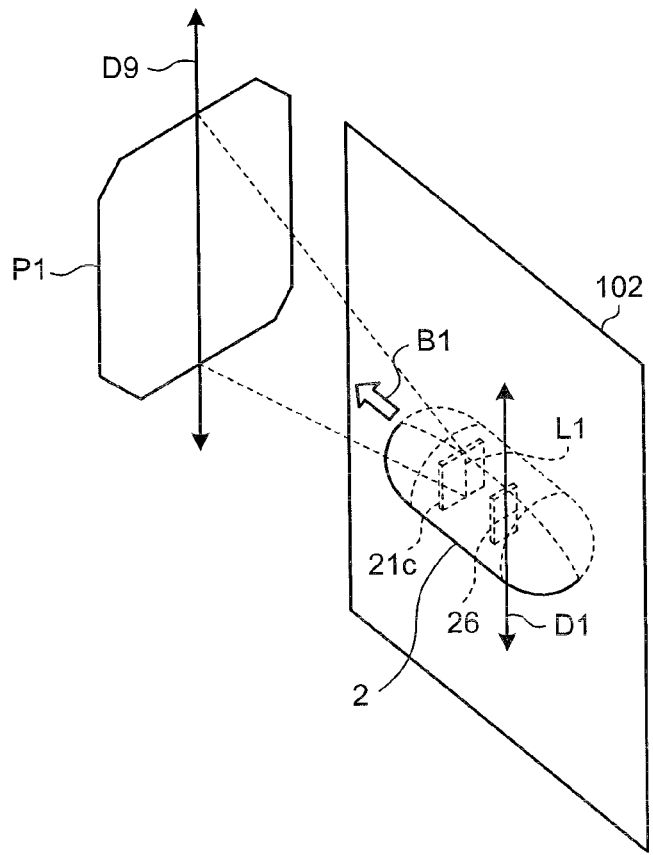
FIG. 13 is a schematic diagram illustrating a calculation process of a direction of intersection line of an imaging surface and a vertical plane in an in-vivo image.
Figure 14:
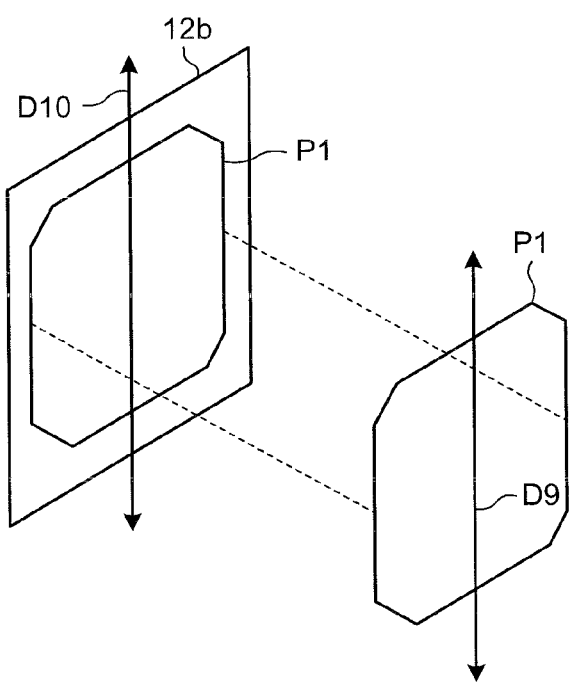
FIG. 14 is a schematic diagram illustrating an image display process displaying the in-vivo image by conforming the direction of intersection line of the in-vivo image and an upward and downward direction of a display screen.

Next, a display process of the in-vivo image by the image display device 10 according to the first embodiment of the present invention is described. FIG. 12 is a flowchart showing one example of a procedure of the image display device according to the first embodiment of the present invention. FIG. 13 is a schematic diagram illustrating a calculation process of a direction of intersection line of the imaging surface and the vertical plane in the in-vivo image. FIG. 14 is a schematic diagram illustrating the image display process for displaying the in-vivo image by conforming the direction of intersection line of the in-vivo image to the upward and downward direction of the display screen.

The image display device 10 sequentially displays the in-vivo images P1 and P2 by the imaging units 21 and 22, respectively, of the capsule medical device 2 in real time by conforming the upward and downward direction of the object in the in-vivo image associated with the magnetic guidance of the capsule medical device 2 to the upward and downward direction of the display screen as described above.

Specifically, as shown in FIG. 12, the controller 14 of the image display device 10 first obtains the in-vivo image by the capsule medical device 2 in the subject 100 (step S101). At the step S101, the controller 14 sequentially obtains the in-vivo images imaged in chronological order by the imaging units 21 and 22 of the capsule medical device 2 from the receiving device 9.

Next, the controller 14 calculates the direction of intersection line of the imaging surface and the vertical plane in the in-vivo image obtained at the step S101 (step S102). At the step S102, the image processor 14a calculates the direction of intersection line of the imaging surface and the vertical plane for each of the in-vivo images P1 and P2 imaged by the imaging units 21 and 22, respectively. Specifically, the image processor 14a calculates a direction of intersection line D9 corresponding to an intersection line L1 of the imaging surface of the solid-state imaging device 21c in the capsule medical device 2 maintaining the above-described specific state (refer to FIG. 5) and the vertical plane 102 parallel to the imaging direction B1 of the solid-state imaging device 21c and the magnetization direction D1 of the permanent magnet 26 for the in-vivo image P1 by the imaging unit 21 as shown in FIG. 13. Similarly, the image processor 14a calculates the direction of intersection line corresponding to the intersection line of the imaging surface of the solid-state imaging device 22c in the capsule medical device 2, which is in the specific state, and the vertical plane 102 parallel to the imaging direction B2 of the solid-state imaging device 22c and the magnetization direction D1 of the permanent magnet 26 for the in-vivo image P2 by the imaging unit 22.

Subsequently, the controller 14 controls the display unit 12 to display the in-vivo image by conforming the direction of intersection line of the in-vivo image calculated at the step S102 to the upward and downward direction of the display screen (step S103). At the step S103, the image processor 14a rotates the in-vivo images P1 and P2 as necessary based on the relative relation between the magnetization direction D1 of the permanent magnet 26 known as shown in FIG. 3 and the upward and downward directions D2 and D3 of the imaging surfaces of the solid-state imaging devices 21c and 22c, respectively, thereby conforming the direction of intersection line in the vivo images P1 and P2 to the upward and downward direction of the display screen of the display unit 12. Specifically, as shown in FIG. 14, the image processor 14a conforms the direction of intersection line D9 of the in-vivo image P1 to the upward and downward direction D10 of the main-image display area 12b. Similarly, the image processor 14a conforms the direction of intersection line of the in-vivo image P2 to the upward and downward direction of the main-image display area 12c (refer to FIG. 6). The controller 14 controls the display unit 12 to display the in-vivo image P1 in the display mode in which the direction of intersection line D9 of the in-vivo image P1 and the upward and downward direction D10 of the main-image display area 12b are conformed to each other in this manner, and controls the display unit 12 to display the in-vivo image P2 in the display mode in which the direction of intersection line of the in-vivo image P2 and the upward and downward direction of the main-image display area 12c are conformed to each other in this manner.

Meanwhile, the upward and downward directions D2 and D3 of the imaging surfaces of the solid-state imaging devices 21c and 22c, respectively, are parallel to the magnetization direction D1 of the permanent magnet 26 in the capsule medical device 2 according to the first embodiment, as shown in above-described FIG. 3. Therefore, the direction of intersection line D9 of the imaging surface of the solid-state imaging device 21c and the vertical plane in the in-vivo image P1 always conforms with the upward and downward direction D2 of the imaging surface of the solid-state imaging device 21c. Similarly, the direction of intersection line of the imaging surface of the solid-state imaging device 22c and the vertical plane in the in-vivo image P2 always conforms with the upward and downward direction D3 of the imaging surface of the solid-state imaging device 22c. In this case, the image processor 14a is not required to rotate the in-vivo images P1 and P2 at the step S103, and may conform the direction of intersection line in the in-vivo images P1 and P2 to the upward and downward direction of the display screen of the display unit 12 by conforming the upward and downward directions of the in-vivo images P1 and P2 to the upward and downward direction of the display screen of the display unit 12. That is to say, the image processor 14a rotates the in-vivo images P1 and P2 based on the relative relation between the known magnetization direction D1 and the upward and downward directions D2 and D3 of the imaging surface of the solid-state imaging devices 21c and 22c, respectively, only when the upward and downward directions D2 and D3 of the imaging surfaces of the solid-state imaging devices 21c and 22c and the magnetization direction D1 of the permanent magnet 26 are not parallel to each other, thereby conforming the direction of intersection line in the in-vivo images P1 and P2 to the upward and downward direction of the display screen of the display unit 12.

After the procedure at the step S103, the controller 14 judges whether to finish the display process of the in-vivo image based on the input information or the like from the input unit 11 (step S104), and when the controller 14 judges that the process is finished (step S104, Yes), the controller 14 finishes the process. On the other hand, when the controller 14 judges that the process is not finished at the step S104 (step S104, No), the controller 14 returns to the above-described step S101 to repeat the procedure after the step S101.

Next, a case in which the operation target image to which the user refers as the operation target when operating the magnetic guidance of the capsule medical device 2 is the in-vivo image P1 by the imaging unit 21 is illustrated to describe the moving direction of the operation target image associated with the operation of the magnetic guidance of the capsule medical device 2. FIG. 15 is a schematic diagram showing one example of the moving direction of the operation target image associated with the operation of the magnetic guidance of the capsule medical device 2 when the capsule medical device 2 is in a tilted position as shown in FIG. 5.

As shown in FIG. 15, the in-vivo image P1 displayed in the main-image display area 12b as the operation target image moves along any of moving directions D11 to D18 in response to each tilt operation of the joysticks 15a and 15b of the operation input unit 15. In this case, the in-vivo image P1, which is the operation target image, moves in a direction easy to be intuitively imagined by the tilt directions of the joysticks 15a and 15b.

Specifically, the in-vivo image P1 moves along the moving directions D11 and D12, which are the left direction and the right direction in the main-image display area 12b seen from the front, respectively, in response to the tilt operation of the joystick 15a in the right and left direction D6. That is to say, the in-vivo image P1 moves in the moving direction D11 in association with the horizontal motion of the capsule medical device 2 horizontally leftward seen from the imaging unit 21 side, and moves in the moving direction D12 in association with the horizontal motion of the capsule medical device 2 horizontally rightward seen from the imaging unit 21. Also, the in-vivo image P1 moves along the moving directions D13 and D14, which are the front direction and the back direction in the main-image display area 12b seen from the front, respectively, in response to the tilt operation of the joystick 15a in the upward and downward direction D5. That is to say, the in-vivo image P1 moves in the moving direction D13 in association with the horizontal motion of the capsule medical device 2 in a horizontal front direction seen from the imaging unit 21 side, and moves in the moving direction D14 in association with the horizontal motion of the capsule medical device 2 in a horizontal back direction seen from the imaging unit 21 side.

On the other hand, the in-vivo image P1 moves along the moving directions D15 and D16, which are the upward direction and the downward direction in the main-image display area 12b seen from the front, respectively, in response to the tilt operation of the joystick 15b in the upward and downward direction D7. That is to say, the in-vivo image P1 moves in the moving direction D15 in association with the swaying motion of the capsule medical device 2 upward seen from the imaging unit 21 side, and moves in the moving direction 16 in association with the swaying motion of the capsule medical device 2 downward seen from the imaging unit 21 side. Also, the in-vivo image P1 moves along the moving directions D17 and D18, which are the counterclockwise direction and the clockwise direction in the main-image display area 12b seen from the front, respectively, in response to the tilt operation of the joystick 15b in the right and left direction D8. That is to say, the in-vivo image P1 moves in the moving direction D17 in association with the turning motion of the capsule medical device 2 leftward seen from the imaging unit 21 side, and moves in the moving direction D18 in association with the turning motion of the capsule medical device 2 rightward seen from the imaging unit 21 side.

Meanwhile, the above-described movement of in-vivo image P1 is a phenomenon that the object in the in-vivo image P1 moves in association with the magnetic guidance of the capsule medical device 2. Also, the moving directions D11 to D18 of the in-vivo image P1 are the same direction as the moving direction of the imaging field A1, which moves in association with the magnetic guidance of the capsule medical device 2, and the direction opposite to the moving direction of the object in the in-vivo image P1. Meanwhile, the movement of the operation target image in response to the above-described tilt operation of the joysticks 15a and 15b is similar also in the case in which the in-vivo image P2 by the imaging unit 22 is the operation target image.

As described above, in the system for guiding capsule medical device according to the first embodiment of the present invention, it is configured that the capsule medical device provided with the imaging unit and the permanent magnet magnetized in the known direction relatively fixed with respect to the upward and downward direction of the imaging surface of the imaging unit in the capsule casing is introduced into the liquid in the subject, the capsule medical device in the liquid is allowed to maintain the specific state in which the magnetization direction of the permanent magnet and the imaging direction of the imaging unit are included in the vertical plane, and the in-vivo image of the subject imaged by the imaging unit of the capsule medical device maintaining the specific state is displayed in the display mode in which the direction of intersection line of the imaging surface and the vertical plane in the in-vivo image and the upward and downward direction of the display screen are conformed to each other. Therefore the in-vivo image by the capsule medical device can be displayed by conforming the upward and downward direction of the subject in the in-vivo image in association with the motion of the imaging field generated when magnetically guiding the capsule medical device in the subject to the up and direction of the display screen. Thereby, the moving direction of the in-vivo image in association with the magnetic guidance of the capsule medical device can be easily intuitionally judged from the operation direction (such as the above-described tilt direction of the joysticks 15a and 15b) of the operation input unit operating the magnetic guidance of the capsule medical device. As a result, it is possible to easily magnetically guide the capsule medical device in the subject while referring to the in-vivo image by the capsule medical device in the subject.

Also, in the system for guiding capsule medical device according to the first embodiment, the in-vivo image imaged by the imaging unit is rotated based on the relative relation between the magnetization direction of the permanent magnet in the capsule medical device and the upward and downward direction of the imaging surface of the imaging unit, thereby conforming the direction of intersection line of the imaging surface and the vertical plane in the in-vivo image to the upward and downward direction of the display screen. Therefore, even when the magnetization direction of the permanent magnet in the capsule medical device and the upward and downward direction of the imaging surface of the imaging unit are not parallel to each other, it is possible to display the in-vivo image by the capsule medical device by surely conforming the upward and downward direction of the object in the in-vivo image in association with the magnetic guidance of the capsule medical device to the upward and downward direction of the display screen. As a result, even when the in-vivo image is imaged by the capsule medical device in which the magnetization direction of such a permanent magnet and the upward and downward direction of the imaging surface are not parallel to each other, it is possible to easily magnetically guide the capsule medical device in the subject while referring to such an in-vivo image.

Further, in the system for guiding capsule medical device according to the first embodiment, the elevation angle information, the direction angle information, and the location information of the capsule medical device in the subject are displayed, so that it is possible to easily estimate the position, the imaging direction, and the current location of the capsule medical device in the subject, which is difficult to be directly visually recognized. Thereby, an imaging site in the subject by the capsule medical device can be estimated, and consequently, an observation in the organ of the subject can be smoothly carried out.

Also, the moving direction of the in-vivo image associated with the turning motion of the capsule medical device depends on the elevation angle of the capsule medical device. Therefore, by displaying the elevation angle information of the capsule medical device, it is possible to easily estimate the moving direction of the in-vivo image associated with the turning motion of the capsule medical device, and consequently, the capsule medical device can be further easily magnetically guided.

On the other hand, in the system for guiding capsule medical device according to the first embodiment, the operation target direction of the capsule medical device, which is the magnetic guidance target, is clearly shown, so that it is possible to allow the user to known the imaging direction of the capsule medical device, which is currently the magnetic guidance operation target. Thereby, the imaging site in the subject by the capsule medical device can be easily estimated, and consequently, the observation in the organ of the subject can be further smoothly carried out.

Also, in the system for guiding capsule medical device according to the first embodiment, since the magnetic guidance direction of the capsule medical device operated by the operation input unit is displayed, it is possible to easily visually recognize whether the magnetic guidance operation by the operation input unit is the operation in an intended magnetic guidance direction. Thereby, the magnetic guidance of the capsule medical device can be smoothly operated.

Further, in the system for guiding capsule medical device according to the first embodiment, the relative location of the operation input unit with respect to the bed supporting the subject is set, and the display direction of each capsule pattern image indicating each of the direction angle information and the location information of the capsule medical device is changed according to the set relative location of the operation input unit. Therefore, the display direction of the capsule pattern image can be changed according to the relative direction of the operation input unit with respect to the subject, that is to say, the point of view direction of the user. As a result, the magnetic guidance of the capsule medical device can be operated by arranging the operation input unit in the desired relative direction with respect to the subject.

Also, in the system for guiding capsule medical device according to the first embodiment, the body posture of the subject on the bed is set based on the input information by the operation input unit, and the image information indicating the set body posture of the subject is displayed. Therefore, by appropriately visually recognizing the image information indicating such a body posture and the elevation angle information and the direction angle information of the capsule medical device, it is possible to easily estimate which side (such as a right side, a left side, a head side, a foot side, a stomach side, and a back side) of the subject is observed through the in-vivo image. As a result, the magnetic guidance of the capsule medical device in the subject can be smoothly operated, and the inside of the organ of the subject can be smoothly observed through the observation of the in-vivo image by the capsule medical device. Further, an estimation result on an observed side in such a subject may be automatically displayed, thereby the magnetic guidance operation of such a capsule medical device and the observation in the organ of the subject can be further smoothly carried out.

Next, a second embodiment of the present invention is described. Although the in-vivo images P1 and P2 imaged by the imaging units 21 and 22 respectively of the capsule medical device 2 are displayed on the display unit 12 in the above-described first embodiment, it is clearly shown which of the in-vivo images P1 and P2 displayed on the display unit 12 is the operation target image in the second embodiment.

Figure 16:
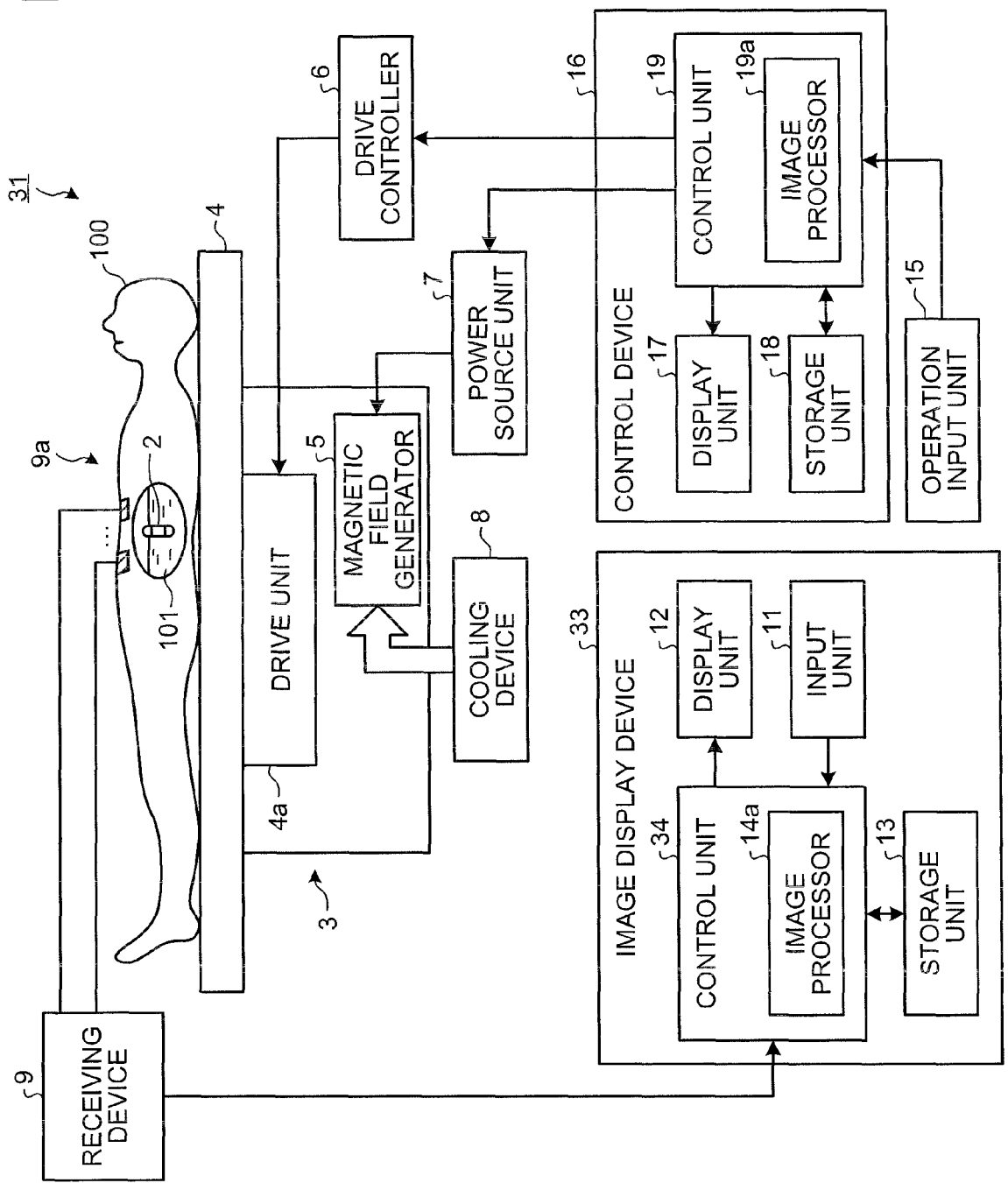
FIG. 16 is a block diagram schematically showing one configuration example of the system for guiding capsule medical device according to a second embodiment of the present invention.

FIG. 16 is a block diagram schematically showing one configuration example of the system for guiding capsule medical device according to the second embodiment of the present invention. As shown in FIG. 16, a system for guiding capsule medical device 31 according to the second embodiment is provided with an image display device 33 in place of the image display device 10 in the system for guiding capsule medical device 1 according to the above-described first embodiment. The image display device 33 is provided with a controller 34 in place of the controller 14 of the image display device 10 according to the above-described first embodiment. Other configurations are identical to those in the first embodiment, and the same reference numerals are given to the same components.

The image display device 33 displays the in-vivo images P1 and P2 imaged by the imaging units 21 and 22, respectively, of the capsule medical device 2 as in the case of the first embodiment, and clearly shows which of the in-vivo images P1 and P2 is the operation target image at the time of the magnetic guidance of the capsule medical device 2.

Figure 17:
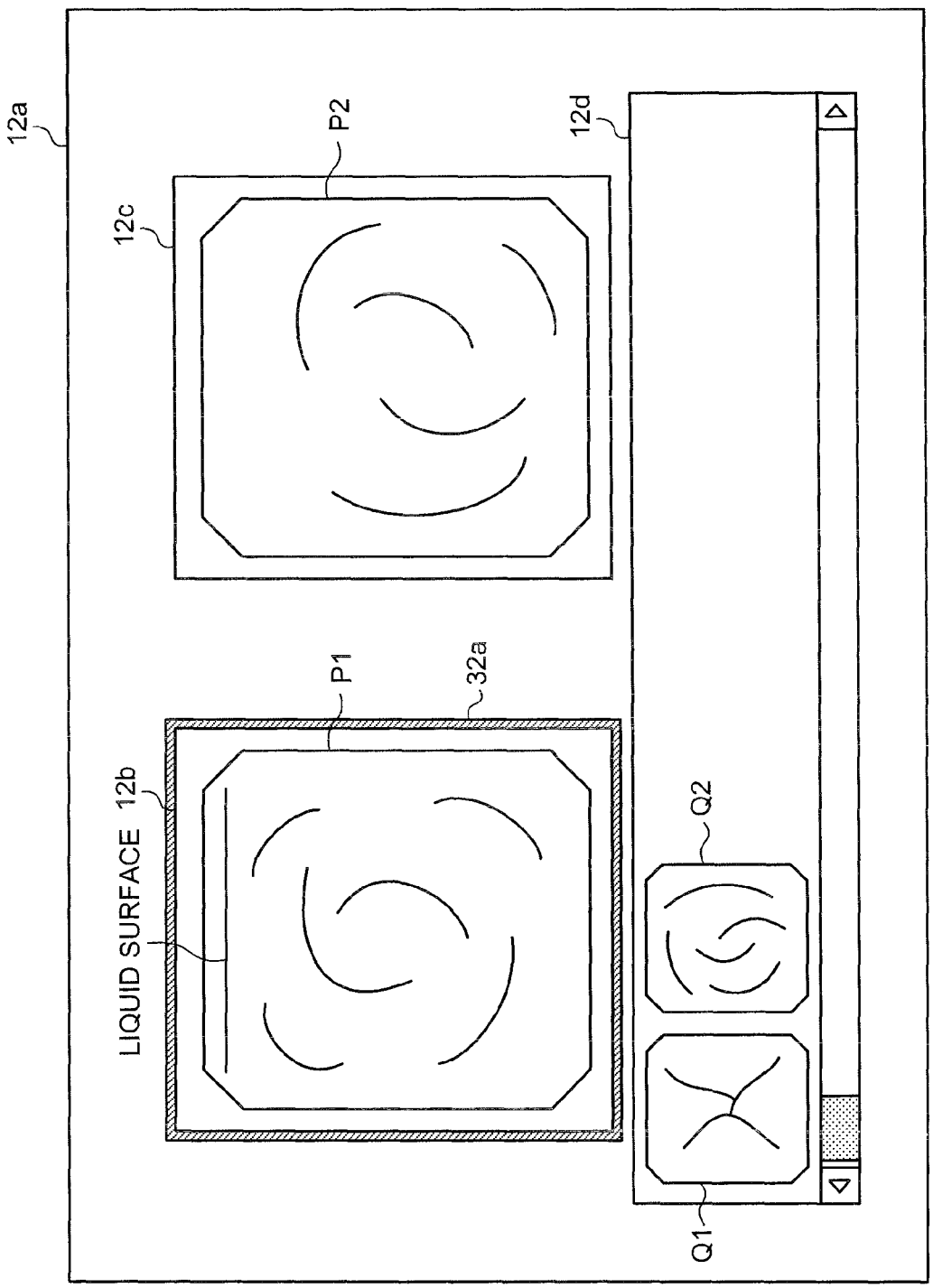
FIG. 17 is a schematic diagram showing one example of the display mode of the image display device according to the second embodiment of the present invention.

The controller 34 of the image display device 33 controls the display unit 12 to display the in-vivo images P1 and P2 in the display mode to clearly show which of the in-vivo images P1 and P2 by the imaging units 21 and 22, respectively, is the operation target image. FIG. 17 is a schematic diagram showing one example of the display mode of the image display device according to the second embodiment of the present invention. The controller 34 sets in advance one of the in-vivo images P1 and P2 as the operation target image based on the input information or the like from the input unit 11. The controller 34 controls the display unit 12 to display the in-vivo images P1 and P2 by the imaging units 21 and 22, respectively, as in the case of the first embodiment, and controls the display unit 12 to emphasize the display area of the in-vivo image set in advance as the operation target image with a frame image or the like. Meanwhile, the controller 34 has the function similar to that of the controller 14 of the image display device 10 according to the above-described first embodiment except for the display control function to clearly show such an operation target image.

The display unit 12 displays the in-vivo images P1 and P2 on the main-image display areas 12b and 12c in the window 12a as shown in FIG. 17 based on the control of the controller 34, and displays a frame image 32a around the main-image display area 12b displaying the in-vivo image P1, which is the operation target image. The display unit 12 clearly shows that the in-vivo image P1 in the main-image display area 12b is the operation target image at the time of the magnetic guidance of the capsule medical device 2 by the display of the frame image 32a.

Meanwhile, although the in-vivo image P1 by the imaging unit 21 is set as the operation target image as one example and the frame image 32a is added to the display area of the in-vivo image P1, which is the operation target image, that is to say, the main-image display area 12b in FIG. 17, the present invention is not limited to this. That is to say, when the in-vivo image P2 by the imaging unit 22 is the operation target image, the display unit 12 displays the frame image 32a around the main-image display area 12c displaying the in-vivo image P2, which is the operation target image, and clearly shows that the in-vivo image P2 in the main-image display area 12c is the operation target image.

As described above, in the system for guiding capsule medical device according to the second embodiment of the present invention, the capsule medical device incorporating the first and second imaging units for imaging the images in imaging directions different from each other and the permanent magnet is introduced into the subject, the first in-vivo image imaged by the first imaging unit and the second in-vivo image imaged by the second imaging unit are displayed in the subject, it is clearly shown which of the first and second in-vivo images is the operation target image at the time of the magnetic guidance of the capsule medical device, and other configurations are made similar to those in the first embodiment. Therefore, the system for guiding capsule medical device capable of enjoying the effect similar to that of the above-described first embodiment, and of surely referring to the operation target image useful in operating the magnetic guidance of the capsule medical device without wondering which of the in-vivo images in the display screen should be referred to as the operation target image when operating the magnetic guidance of the capsule medical device, thereby easily operating the magnetic guidance of the capsule medical device may be realized.

Next, a third embodiment of the present invention is described. Although the elevation angle information and the direction angle information of the capsule medical device 2 are displayed on the display unit 17 of the control device 16 for controlling the magnetic guidance of the capsule medical device 2 in the above-described first embodiment, the elevation angle information and the direction angle information of the capsule medical device 2 are displayed by being associated with the operation target image out of the in-vivo images P1 and P2 imaged by the imaging units 21 and 22, respectively, of the capsule medical device 2 in the third embodiment.

Figure 18:
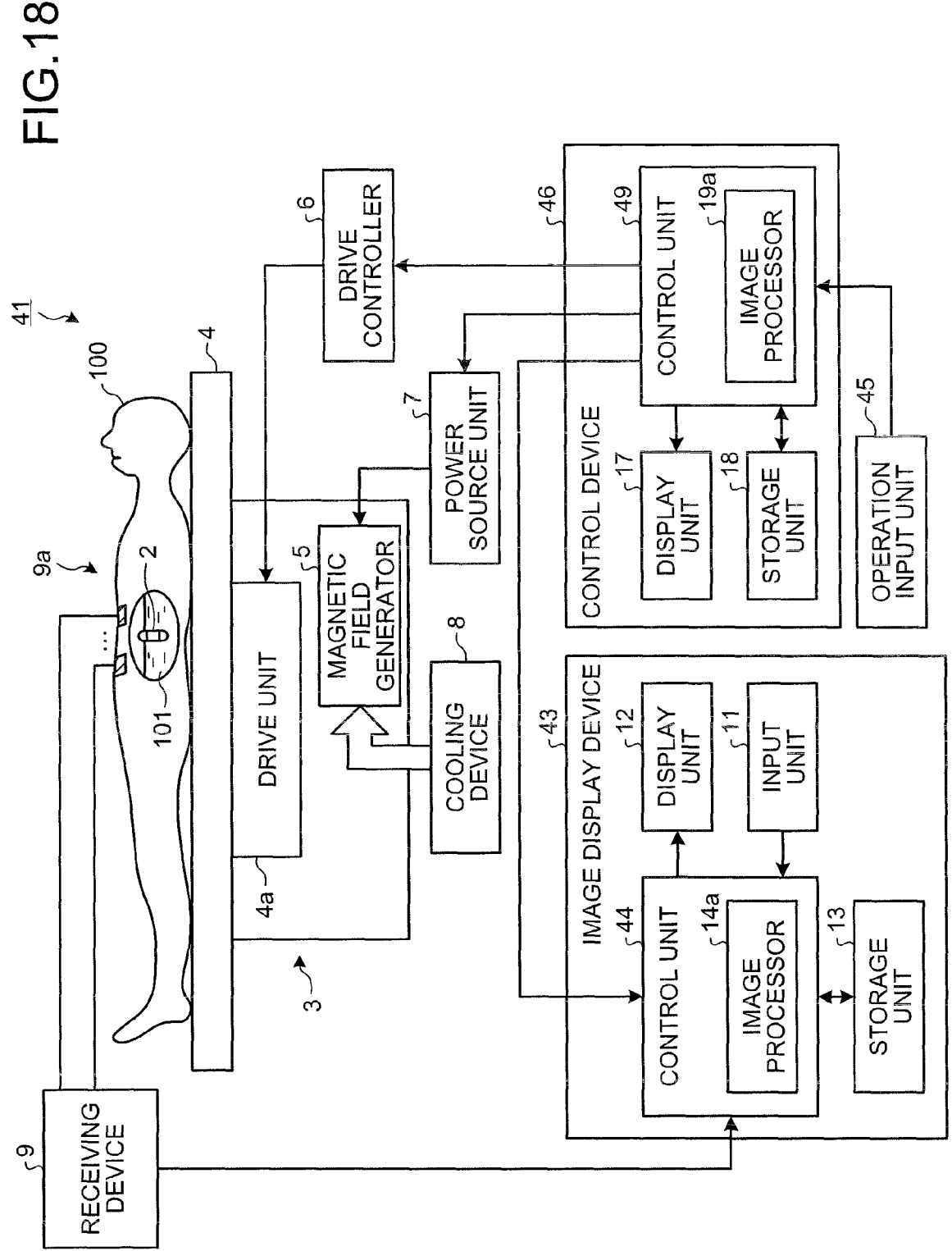
FIG. 18 is a block diagram schematically showing one configuration example of the system for guiding capsule medical device according to a third embodiment of the present invention.

FIG. 18 is a block diagram schematically showing one configuration example of the system for guiding capsule medical device according to the third embodiment of the present invention. As shown in FIG. 18, a system for guiding capsule medical device 41 according to the third embodiment is provided with an image display device 43 in place of the image display device 10 of the system for guiding capsule medical device 1 according to the above-described first embodiment, an operation input unit 45 in place of the operation input unit 15, and a control device 46 in place of the control device 16. In the third embodiment, the image display device 43 is provided with a controller 44 in place of the controller 14 of the image display device 10 according to the above-described first embodiment. Also, the control device 46 is provided with a controller 49 in place of the controller 19 of the control device 16 according to the above-described first embodiment. Other configurations are identical to those of the first embodiment, and the same reference numerals are given to the same components.

The image display device 43 displays the in-vivo images P1 and P2 imaged by the imaging units 21 and 22, respectively, of the capsule medical device 2 as in the case of the first embodiment, and displays the elevation angle information and the direction angle information of the capsule medical device 2 by relating them to the operation target image at the time of the magnetic guidance of the capsule medical device 2, which is any of the in-vivo images P1 and P2.

The controller 44 of the image display device 43 controls the display unit 12 to display the elevation angle information and the direction angle information of the capsule medical device 2, which is the magnetic guidance object, by relating them to the operation target image out of the in-vivo images P1 and P2 by the imaging units 21 and 22, respectively. Specifically, the controller 44 sets in advance one of the in-vivo images P1 and P2 as the operation target image based on the input information or the like from the input unit 11. Also, the controller 44 obtains the angle information and the direction information of the capsule medical device 2 from the controller 49 of the control device 46. The controller 44 controls the display unit 12 to display the in-vivo images P1 and P2 by the imaging units 21 and 22, respectively, as in the case of the first embodiment, and controls the display unit 12 to display the elevation angle information and the direction angle information of the capsule medical device 2 by relating them to the in-vivo image set in advance as the operation target image. In this case, the controller 44 controls the display of the elevation angle information of the capsule medical device by the display unit 12 based on the angle information of the capsule medical device 2 obtained from the controller 49 of the control device 46. Also, the controller controls the display of the direction angle information of the capsule medical device 2 by the display unit 12 based on the direction information of the capsule medical device 2 obtained from the controller 49 of the control device 46.

Also, the controller 44 controls the display unit 12 to display the information indicating that the operation information of the capsule medical device 2 is input by the operation input unit 45. In this case, the controller 44 receives notification that the operation information is input by the operation input unit 45 from the controller 49 of the control device 46, and allows the display unit 12 to display the information indicating that the operation information of the capsule medical device 2 is input based on the notification of the input. Meanwhile, the controller 44 has the function similar to that of the controller 14 of the image display device 10 according to the above-described first embodiment, except for the display control function of the elevation angle information, the direction angle information, and the information indicating that the operation information is input, of the capsule medical device 2, for the above-described display unit 12.

Figure 19:
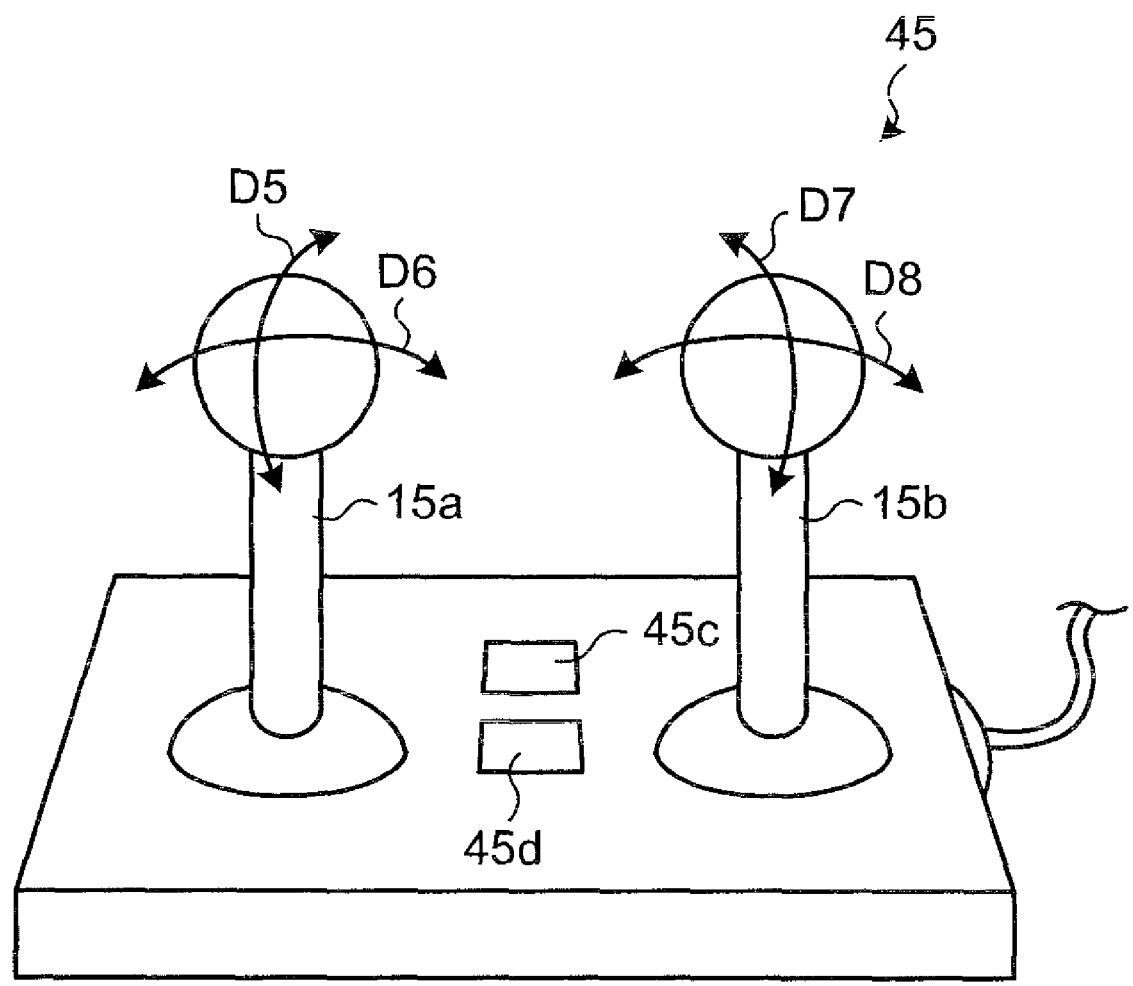
FIG. 19 is a schematic diagram showing one configuration example of the operation input unit of the third embodiment of the present invention.

The operation input unit 45 has a function of inputting the instruction information to the image display device 43 in addition to the operation information to operate the magnetic guidance of the above-described capsule medical device 2. FIG. 19 is a schematic diagram showing one configuration example of the operation input unit in the third embodiment of the present invention. As shown in FIG. 19, the operation input unit 45 is provided with input switches 45c and 45d in addition to the above-described joysticks 15a and 15b. Meanwhile, the operation input unit 45 has the function similar to that of the operation input unit 15 of the system for guiding capsule medical device 1 according to the above-described first embodiment, except for the information input function by the input switches 45c and 45d.

The input switch 45c is the switch to input the instruction information to instruct to selectively save the in-vivo image. The operation input unit 45 inputs the instruction information to selectively save the in-vivo image to the controller 49 of the control device 46 in response to a push operation of the input switch 45c. In this case, the controller 49 transfers the instruction information from the operation input unit 45 to the controller 44 of the image display device 43. The controller 44 of the image display device 43 extracts the in-vivo image, which is instructed to be saved by such instruction information (that is to say, the image selected by the user), from the in-vivo image group of the subject 100. Then, the controller 44 controls the display unit 12 to add the mark to the extracted in-vivo image, and controls the storage unit 13 to store the in-vivo image data by relating the same to the mark. Further, the controller 44 controls the display unit 12 to additionally display the reduced image (such as the thumbnail image) of the in-vivo image.

Meanwhile, the controller 44 may allow the display unit 12 to additionally display the reduced image of the in-vivo image, which is the operation target image, out of the in-vivo images P1 and P2 displayed on the display unit 12 at the time of the push operation of the input switch 45c, or allow the display unit 12 to additionally display both of the reduced images. On the other hand, the controller 44 may store the data of the in-vivo image, which is the operation target image, out of the in-vivo images P1 and P2 displayed on the display unit 12 at the time of the push operation of the input switch 45c in the storage unit 13, or may store the both of data in the storage unit 13. Alternatively, the controller 44 may select and save one of the data of the in-vivo image in the display screen when the push operation of the input switch 45 is performed. In this case, the controller 44 may store the data of the in-vivo image selected by the click operation, the operation of the arrow key or the like from the in-vivo images P1 and P2 in the display screen after the push operation of the input switch 45c.

The input switch 45d is the switch to input the instruction information to instruct to switch the display mode of the in-vivo image. The operation input unit 45 inputs the instruction information to switch the display mode of the in-vivo image to the controller 49 of the control device 46 in response to the push operation of the input switch 45d. In this case, the controller 49 transfers the instruction information from the operation input unit 45 to the controller 44 of the image display device 43. The controller 44 of the image display device 43 controls the display unit 12 to switch the display format of each in-vivo image of the subject 100 from the moving image display to the still image display based on such instruction information, or controls the display unit 12 to switch from the still image display to the moving image display.

The control device 46 is provided with the controller 49 as described above to control each display operation by the image display device 43 of the elevation angle information, the direction angle information, and the information indicating that operation information is input, of the capsule medical device 2. Meanwhile, the control device 46 has the function similar to that of the control device 16 of the system for guiding capsule medical device 1 according to the above-described first embodiment, except for the control function of the image display device 43.

The controller 49 transmits the angle information of the capsule medical device 2 to the controller 44 of the image display device 43 to control the display of the elevation angle information of the capsule medical device 2 by the image display device 43. Specifically, the controller 49 calculates the angle between the imaging direction of the imaging unit to image the operation target image out of the imaging units 21 and 22 of the capsule medical device 2 and the vertical axis, that is to say, the elevation angle of the capsule medical device 2. Meanwhile, the controller 49 calculates the elevation angle of the capsule medical device 2 based on the information of the guidance magnetic field (such as the magnetic field strength and the magnetic field direction) applied by the magnetic field generator 5 to the capsule medical device 2, the physical information (such as the mass, the shape, the location of center of gravity, and the magnetic moment) of the capsule medical device 2, and the density information of the liquid 101. The controller 49 transmits the angle information indicating the calculated elevation angle of the capsule medical device 2 to the controller 44 of the image display device 43, thereby allowing the image display device 43 to display the elevation angle information of the capsule medical device 2 corresponding to the angle information.

Also, the controller 49 transmits the direction information of the capsule medical device 2 to the controller 44 of the image display device 43 to control the display of the direction angle information of the capsule medical device 2 by the image display device 43. Specifically, the controller 49 calculates a horizontal component direction of the imaging direction of the imaging unit for imaging the operation target image out of the imaging units 21 and 22 of the capsule medical device 2. Meanwhile, the controller 49 calculates the horizontal component direction of the imaging direction of the capsule medical device 2 based on the information (in detail, the magnetic field direction of the horizontal component of the guidance magnetic field) of the guidance magnetic field to be applied by the magnetic field generator 5 to the capsule medical device 2. The controller 49 transmits the direction information indicating the calculated horizontal component direction to the controller 44 of the image display device 43, thereby allowing the image display device 43 to display the direction angle information of the capsule medical device 2 corresponding to the direction information.

Further, the controller 49 informs the controller 44 of the image display device 43 that the operation information is input, when the operation information of the capsule medical device 2 is input by the operation input unit 45. Thereby, the controller 49 allows the image display device 43 to display the information indicating that the operation information of the capsule medical device 2 is input by the operation input unit 45.

Meanwhile, the controller 49 has the function similar to that of the controller 19 of the control device 16 in the above-described first embodiment, except for the control function to allow the image display device 43 to display the elevation angle information, the direction angle information, and the information indicating that the operation information is input, of the capsule medical device 2 in this manner.

Figure 20:
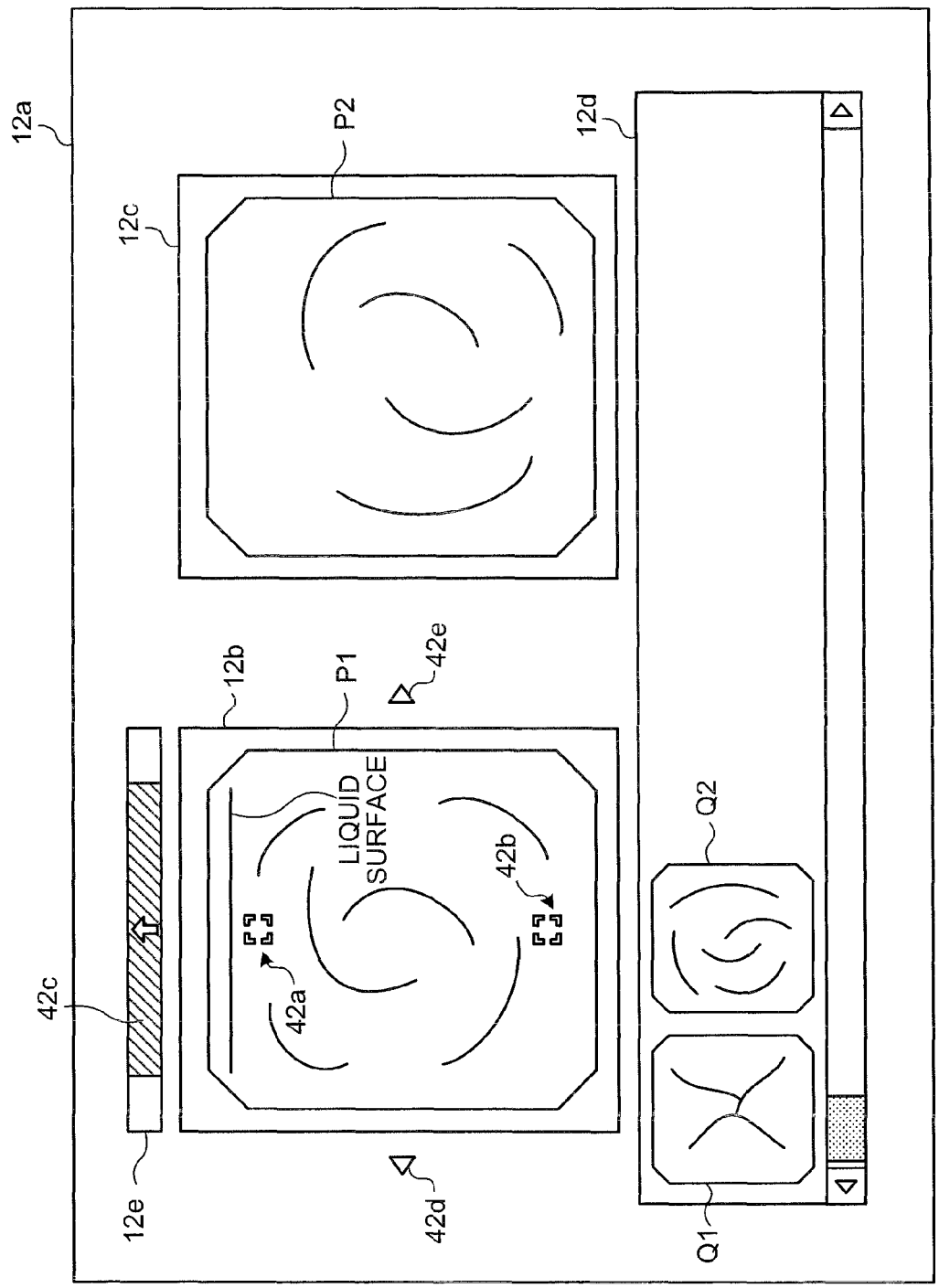
FIG. 20 is a schematic diagram showing one example of the display mode of the image display device according to the third embodiment of the present invention.
Figure 22:
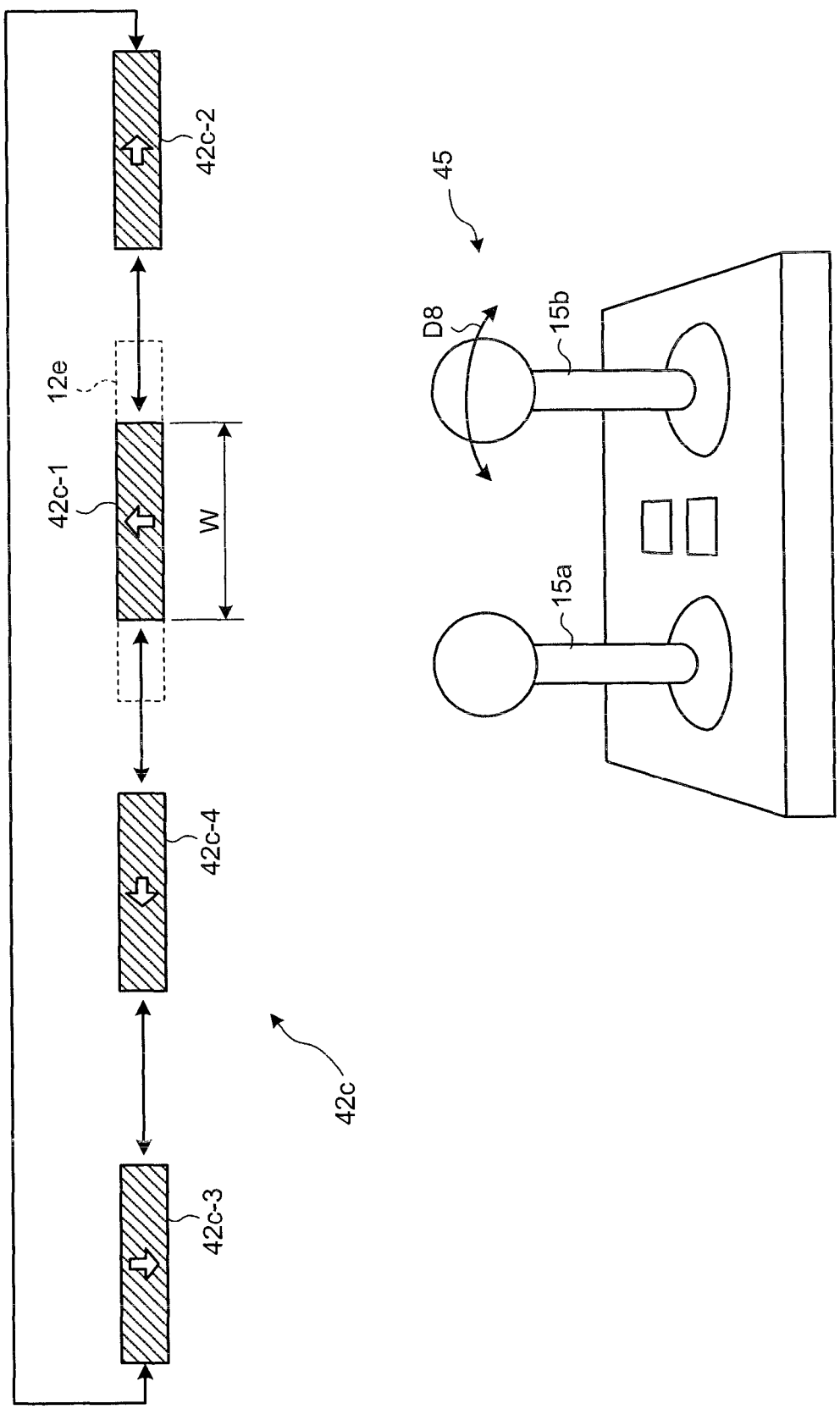
FIG. 22 is a schematic diagram illustrating the display process of direction angle information of the capsule medical device, by the image display process.

Next, the display process by the image display device 43 of the elevation angle information, the direction angle information, and the information indicating that the operation information is input, of the capsule medical device 2, is described. FIG. 20 is a schematic diagram showing one example of the display mode of the image display device according to the third embodiment of the present invention. FIG. 21 is a schematic diagram illustrating the display process by the image display device of the information showing that the elevation angle information and the operation information of the capsule medical device are input. FIG. 22 is a schematic diagram illustrating the display process by the image display device of the direction angle information of the capsule medical device.

The display unit 12 of the image display device 43 displays the elevation angle information of the capsule medical device 2 by relating the same to the in-vivo image P1, which is the operation target image, out of the in-vivo images P1 and P2 displayed in the main-image display areas 12b and 12c in the window 12a, as shown in FIG. 20, for example. Specifically, the display unit 12 displays two marks 42a and 42b by arranging them in one line lengthwise in the in-vivo image P1, which is the operation target image. Here, the controller 44 of the image display device 43 determines the display locations of the marks 42a and 42b in the in-vivo image P1 based on the angle information of the capsule medical device 2 obtained from the controller 49 of the control device 46, and controls the display unit 12 to display the marks 42a and 42b on the determined display locations. The display unit 12 displays the marks 42a and 42b on the display locations corresponding to such angle information, that is to say, the elevation angle of the capsule medical device 2, and displays the elevation angle information of the capsule medical device 2 by the display locations of the marks 42a and 42b in the in-vivo image P1. Here, the mark 42a is displayed on the location indicating the horizontal direction in the in-vivo image P1, and the mark 42b is displayed on the location indicating the vertical direction in the in-vivo image P1.

Also, the display unit 12 longitudinally moves the marks 42a and 42b in the in-vivo image P1 in response to the swaying motion of the capsule medical device 2 at the time of the tilt operation of the joystick 15b of the operation input unit 45 in the upward and downward direction D7, that is to say, at the time of the magnetic guidance, as shown in FIG. 21. The marks 42a and 42b move downward in the in-vivo image P1 with an increase in the elevation angle of the capsule medical device 2. When the elevation angle of the capsule medical device 2 is 90 degrees, that is to say, the imaging direction (the as the imaging direction B1 of the imaging unit 21) of the operation target image and the horizontal direction are parallel to each other, the mark 42a moves to an image central portion of the in-vivo image P1, which is the operation target image. On the other hand, the marks 42a and 42b move upward in the in-vivo image P1 with a decrease in the elevation angle of the capsule medical device 2. When the elevation angle of the capsule medical device 2 is 0 degree, that is to say, when the imaging direction (the as the imaging direction B1 of the imaging unit 21) of the operation target image and the vertical direction are parallel to each other, the mark 42b moves to the image central portion of the in-vivo image P1, which is the operation target image.

On the other hand, the display unit 12 displays the direction angle information of the capsule medical device 2 by relating the same to the in-vivo image P1, which is the operation target image, out of the in-vivo images P1 and P2, as shown in FIG. 20, for example. Specifically, the window 12a includes a bar-type information display area 12e in the vicinity of the upper portion of the main-image display area 12b displaying the in-vivo image P1, which is the operation target image. The display unit 12 displays the direction information 42c in the information display area 12e based on the control of the controller 44, and displays the direction angle information of the capsule medical device 2 by the display location of the direction information 42c in the information display area 12e.

Figure 27:
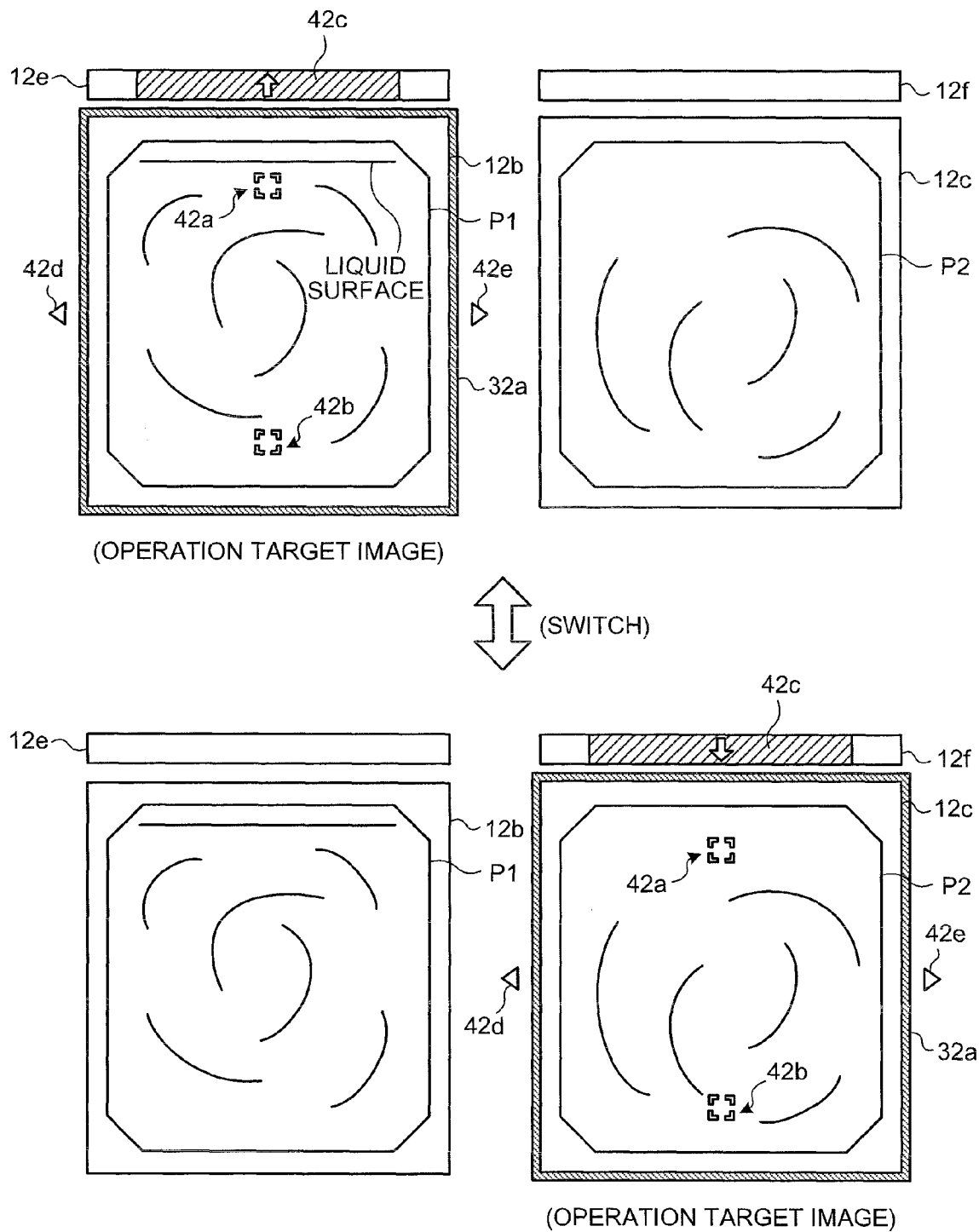
FIG. 27 is a schematic diagram showing a state in which the image display device according to the third embodiment switches the operation target image.

Here, the direction information 42c is formed of four different pieces of direction information 42c-2 to 42c-4 for each direction of the capsule medical device 2 as shown in FIG. 27. Each of the pieces of direction information 42c-1 to 42c-4 is bar-type image information having a width W corresponding to a direction angle area (±45 degrees, for example) for each direction of the capsule medical device 2, and includes an arrow indicating the direction of the capsule medical device 2 in a central portion of the bar. In detail, the direction information 42c-1 includes an up-pointing arrow indicating that the horizontal component direction of the operation target direction of the capsule medical device 2 is the direction to the back of the operation input unit 45 seen from the front, in the central portion of the bar. The direction information 42c-2 includes a right-pointing arrow indicating that the horizontal component direction of the operation target direction of the capsule medical device 2 is the direction to the right of the operation input unit 45 seen from the front, in the central portion of the bar. The direction information 42c-3 includes a down-pointing arrow indicating that the horizontal component direction of the operation target direction of the capsule medical device 2 is the direction to the front of the operation input unit 45 seen from the front, in the central portion of the bar. The direction information 42c-4 includes a left-pointing arrow indicating that the horizontal component direction of the operation target direction of the capsule medical device 2 is the direction to the left of the operation input unit 45 seen from the front, in the central portion of the bar. Meanwhile, the location of each arrow in the pieces of direction information 42c-1 to 42c-4 is not limited to the central portion of the bar and may be set in consideration of distortion of the optical systems 21b and 22b of the capsule medical device 2.

The controller 44 of the image display device 43 determines the display location of the direction information 42c in the information display area 12e based on the direction information of the capsule medical device 2 obtained from the controller 49 of the control device 46, that is to say, the calculated result of the horizontal component direction of the operation object direction of the capsule medical device 2. The controller 44 controls the display unit 12 to display one of the direction information 42c (any of the pieces of direction information 42c-1 to 42c-4) conforming with the direction information of the capsule medical device 2 on the display location in the information display area 12e thus determined. The display unit 12 displays the direction information 42c on the location in the information display area 12e based on the control of the controller 44, and displays the direction angle information of the capsule medical device 2 by the display location of the direction information 42c.

Specifically, when the operation target direction (the imaging direction B1 of the imaging unit 21, for example) of the capsule medical device 2 is the direction to the back of the operation input unit 45 seen from the front, the display unit 12 displays the direction information 42c-1 such that the up-pointing arrow is located on the central portion of the information display area 12e. Then, the display unit 12 laterally moves the direction information 42c-1 in the information display area 12e in the same direction as the direction around the vertical axis of the turning motion in response to the turning motion of the capsule medical device 2 in an area of ±45 degrees. Also, when the operation target direction of the capsule medical device 2 is the direction to the right of the operation input unit 45 seen from the front, the display unit 12 displays the direction information 42c-2 such that the right-pointing arrow is located on the central portion of the information display area 12e. Then, the display unit 12 laterally moves the direction information 42c-2 in the information display area 12e in the same direction as the direction around the vertical axis of the turning motion in response to the turning motion of the capsule medical device 2 in an area of ±45 degrees. Also, the display unit 12 displays the direction information 42c-3 such that the down-pointing arrow is located on the central portion of the information display area 12e when the operation target direction of the capsule medical device 2 is the direction to the front of the operation input unit 45. Then, the display unit 12 laterally moves the direction information 42c-3 in the information display area 12e in the same direction as the direction around the vertical axis of the turning motion in response to the turning motion of the capsule medical device 2 in an area of ±45 degrees. Also, the display unit 12 displays the direction information 42c-4 such that the left-pointing arrow is located on the central portion of the information display area 12e when the operation target direction of the capsule medical device 2 is to the left of the operation input unit 45 seen from the front. Then, the display unit 12 laterally moves the direction information 42c-3 in the information display area 12e in the same direction as the direction around the vertical axis of the turning motion in response to the turning motion of the capsule medical device 2 in an area of ±45 degrees.

Also, the display unit 12 sequentially laterally moves the direction information 42c in the information display area 12e in response to the tilt operation of the joystick 15b of the operation input unit 45 in the right and left direction D8, that is to say, the turning motion of the capsule medical device 2 at the time of the magnetic guidance as shown in FIG. 22. In this case, when the capsule medical device 2 turns clockwise from the back side of the operation input unit 45 seen from the front, the display unit 12 sequentially displays the direction information 42c-1, 42c-2, 42c-3, and 42c-4 in the information display area 12e in this order. On the other hand, when the capsule medical device 2 turns counterclockwise from the back side of the operation input unit 45, the display unit 12 sequentially displays the direction information 42c-1, 42c-4, 42c-3, and 42c-2 in the information display area 12e in this order.

On the other hand, the display unit 12 displays the information indicating that the operation information of the capsule medical device 2 is input by the operation input unit 45 by relating the same to the in-vivo image P1, which is the operation target image, out of the in-vivo images P1 and P2 as shown in FIG. 20, for example. Specifically, when the controller 44 of the image device 43 receives the notification indicating that the operation information of the capsule medical device 2 is input by the operation input unit 45 from the controller 49 of the control device 46, the controller 44 controls the display unit 12 to display the information indicating that the operation information is input, based on the notification.

The display unit 12 displays the marks 42d and 42e indicating that the operation information of the capsule medical device 2 is input, by relating them to the in-vivo image P1, which is the operation target image, as shown in FIG. 20, based on the control of the controller 44. Here, the mark 42d is the information indicating that the operation information of the magnetic guidance, which allows the capsule medical device 2 to perform the horizontal motion to the left of the operation target direction (the imaging direction B1, for example) of the capsule medical device 2, is input. Also, the mark 42e is the information indicating that the operation information of the magnetic guidance, which allows the capsule medical device 2 to perform the horizontal motion to the right of the operation target direction of the capsule medical device 2, is input. When the joystick 15a of the operation input unit 45 is tilted to the left of the right and left direction D6, the display unit 12 displays the mark 42d in the vicinity of the left side of the main-image display area 12b and on the central line of the in-vivo image P1, as shown in FIG. 21. Also, when the joystick 15a is tilted to the right of the right and left direction D6, the display unit 12 displays the mark 42e in the vicinity of the right side of the main-image display area 12b and on the central line of the in-vivo image P1.

Meanwhile, the display unit 12 may always display the marks 42d and 42e in the vicinity of the main-image display area 12b with a predetermined color (white, for example) regardless of the presence of the input of the operation information by the operation input unit 45, and when such operation information is input, this may display the mark corresponding to the operation information out of the marks 42d and 42e with another color (yellow, for example).

On the other hand, as shown in FIG. 21, when the joystick 15a of the operation input unit 45 is tilted in the upward and downward direction D5, the display unit 12 changes the display color of the mark 42a in the in-vivo image P1 from a default color (yellow, for example) to another color (blue, for example). Thereby, the display unit 12 displays the information indicating that the operational information corresponding to the tilt operation of the joystick 15a, that is to say, the operation information of the magnetic guidance, which allows the capsule medical device 2 to perform the horizontal motion to the back or the front of the operation target direction (the imaging direction B1, for example) of the capsule medical device 2 seen from the front, is input. Also, when the operation information of the magnetic guidance, which allows the capsule medical device 2 to perform vertical motion, is input by the operation input unit 45, the display unit 12 changes the display color of the mark 42b in the in-vivo image P1 from the default color (yellow, for example) to another color (blue, or example). Thereby, the display unit 12 displays the information indicating that the operation information corresponding to such a vertical motion is input.

Meanwhile, although the in-vivo image P1 by the imaging unit 21 is set as the operation target image as one example, and the marks 42a and 42b of the elevation angle information, the direction information 42c, and the marks 42d and 42e are displayed by being related to the in-vivo image P1, which is the operation target image, in above-described FIGS. 20 and 21, the present invention is not limited to this. That is to say, the in-vivo image P2 by the imaging unit 22 may be the operation target image, and in this case, the display unit 12 may display the above-described marks 42a and 42b of the elevation angle information, the direction information 42c, and the marks 42d and 42e by relating them to the in-vivo image P2, which is the operation target image.

As described above, in the system for guiding capsule medical device according to the third embodiment of the present invention, the elevation angle information and the direction angle information of the capsule medical device and the information indicating that the operation information is input are displayed by being related to the operation of the capsule medical device image out of the in-vivo images imaged by a plurality of imaging units in the capsule medical device, and other configurations are made the same as those of the first embodiment. Therefore, the system for guiding capsule medical device capable of enjoying the effect similar to that of the above-described first embodiment, and of easily visually recognizing the elevation angle, the direction angle and the motion direction (magnetic guidance direction) of the capsule medical device while referring to each in-vivo image of the subject imaged by the capsule medical device, which is the magnetic guidance target, and consequently, capable of further easily operating the magnetic guidance of the capsule medical device in the subject can be realized.

Also, by displaying the direction angle information of the capsule medical device by relating the same to such an operation target image, it is possible to operate the magnetic guidance of the capsule medical device while comprehending the direction of the imaging direction of the capsule medical device, which is the magnetic guiding target, in the subject. Thereby, the in-vivo image necessary for an examination in the organ of the subject can be easily imaged, and as a result, the examination in the organ of the subject through such an in-vivo image can be performed in a short time.

Next, a fourth embodiment of the present invention is described. Although the elevation angle information and the direction angle information of the capsule medical device 2 are displayed by being related to the operation target image out of the in-vivo images P1 and P2 imaged by the imaging units 21 and 22, respectively, of the capsule medical device 2 in the above-described third embodiment, the elevation angle information and the direction angle information of the capsule medical device 2 are displayed by selectively switching the operation target image at the time of the magnetic guidance of the capsule medical device 2 from the in-vivo images P1 and P2 and relating them to the in-vivo image selected as the operation target image, in the fourth embodiment.

Figure 23:
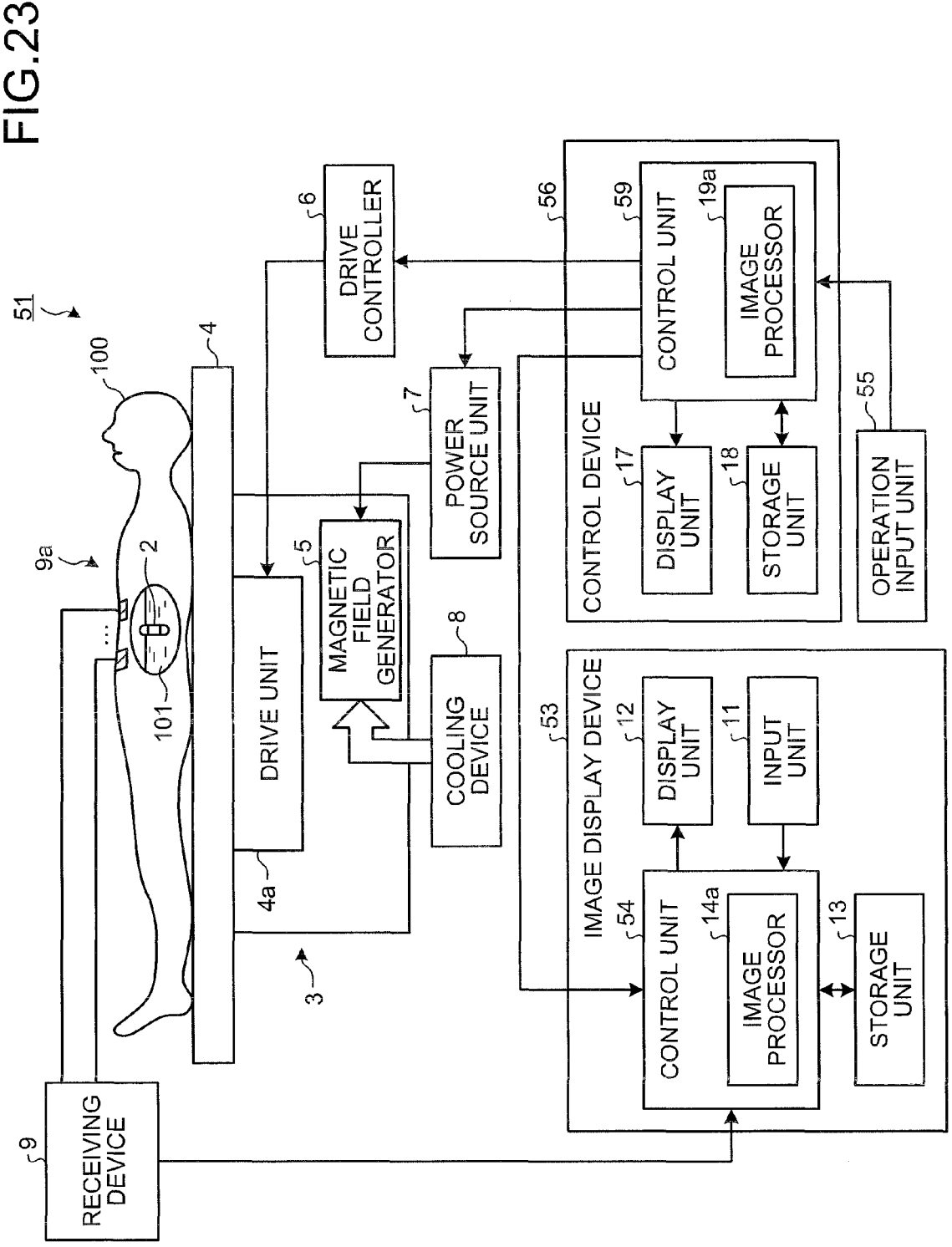
FIG. 23 is a block diagram schematically showing one configuration example of the system for guiding capsule medical device according to a fourth embodiment of the present invention.

FIG. 23 is a block diagram schematically showing one configuration example of the system for guiding capsule medical device according to the fourth embodiment of the present invention. As shown in FIG. 23, a system for guiding capsule medical device 51 according to the fourth embodiment is provided with an image display device 53 in place of the image display device 43 of the system for guiding capsule medical device 41 according to the above-described third embodiment, an operation input unit 55 in place of the operation input unit 45, and a control device 56 in place of the control device 46. In the fourth embodiment, the image display device 53 is provided with a controller 54 in place of the controller 44 of the image display device 43 according to the above-described third embodiment. Also, the control device 56 is provided with a controller 59 in place of the controller 49 of the control device 46 according to the above-described third embodiment. Other configurations are the same as those of the third embodiment, and the same reference numerals are given to the same components.

The image display device 53 clearly shows either one of the in-vivo images P1 and P2 imaged by the imaging units 21 and 22 of the capsule medical device 2, which is selected by selection information input by the operation input unit 55, as the operation target image at the time of the magnetic guidance of the capsule medical device 2. The image display device 53 switches the operation target image from the in-vivo images P1 and P2 in response to the selection information from the operation input unit 55, and switches the display of the elevation angle information and the direction angle information of the capsule medical device 2 in response to such switching of the operation target image. Meanwhile, the image display device 53 has the function similar to that of the image display device 43 in the above-described third embodiment, except for a function of clearly showing such an operation target image and a function of switch displaying the elevation angle information and the direction angle information of the capsule medical device 2.

The controller 54 of the image display device 53 obtains the selection information input by the operation input unit 55 from the controller 59 of the control device 56, and controls the display unit 12 to clearly show the in-vivo image selected by the obtained selection information out of the in-vivo images P1 and P2 by the imaging units 21 and 22, respectively, as the operation target image. The controller 54 sequentially switches the operation target image between the in-vivo images P1 and P2 each time the controller 54 obtains such selection information, and controls the display unit 12 to switch the in-vivo image to be clearly shown as the operation target image in response to such switching of the operation target image. Also, the controller 54 switches the operation information and the direction angle information of the capsule medical device 2 and the information indicating that the operation information is input, between the in-vivo images P1 and P2, in response to the switching of the operation target image. Then, the controller 54 controls the display unit 12 to display the elevation angle information and the direction angle information of the capsule medical device 2 and the information indicating that the operation information is input, by always being related to the in-vivo image, which is the operation target image, out of the in-vivo images P1 and P2.

Meanwhile, the controller 54 has the function similar to that of the controller 44 of the image display device 43 in the above-described third embodiment, except for the control function of the display unit 12 in association with the switching of such an operation target image.

Figure 24:
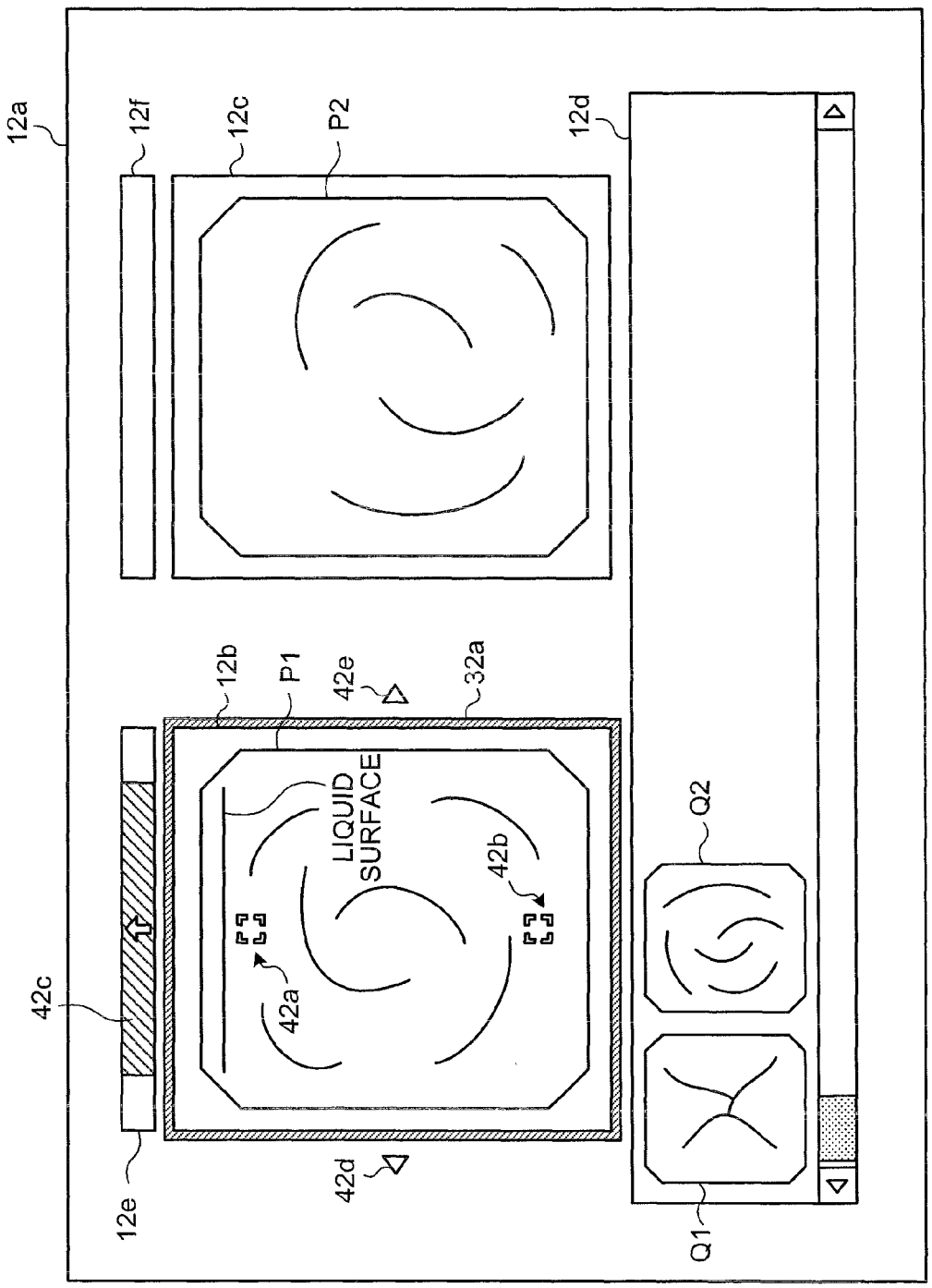
FIG. 24 is a schematic diagram showing one example of the display mode of the image display device according to the fourth embodiment of the present invention.

The display unit 12 displays the elevation angle information and the direction angle information of the capsule medical device 2 and the information indicating that the operation information is input, by always relating them to the in-vivo image, which is the target object image, out of the in-vivo images P1 and P2 by the imaging units 21 and 22, respectively, based on the control of the controller 54. FIG. 24 is a schematic diagram showing one example of the display mode of the image display device according to the fourth embodiment of the present invention. The display unit 12 displays a frame image 32*a* around the main-image display area 12*b* out of the main-image display areas 12*b* and 12*c*, as shown in FIG. 24, for example, and clearly shows the in-vivo image P1 in the main-image display area 12*b* as the operation target image by the display of the frame image 32*a*. In this case, the display unit 12 displays the marks 42*a* and 42*b* of the elevation information in the in-vivo image P1, which is the operation target image, as in the case of the above-described third embodiment, and displays the direction information 42*c* in the information display area 12*e* in the vicinity of the upper side of the main-image display area 12*b*. Also, the display unit 12 displays the mark 42*d* or 42*e* in the vicinity of the main-image display area 12*b* in response to the input of the operation information by the operation input unit 55, or changes the display color of the mark 42*a* or 42*b* in the in-vivo image P1, which is the operation target image.

Here, the window 12*a* of the display unit 12 includes a bar-type information display area 12*f*, which is similar to the above-described information display area 12*e* in the vicinity of the upper side display area 12*c* as shown in FIG. 24. When the in-vivo image P2 is the operation target image, the display unit 12 changes the display location of the frame image 32*a* from the circumstance of the above-described main-image display area 12*b* to the circumstance of the main-image display area 12*c* to display the frame image 32*a*, thereby clearly showing the in-vivo image P2 in the main-image display area 12*c* as the operation target image. At the same time, the display unit 12 displays the marks 42*a* and 42*b* of the elevation information displayed in the in-vivo image P1 in the in-vivo image P2, which is the operation target image, and displays the direction information 42*c* displayed in the information display area 12*e* on a main-image display area 12*b* side in the information display area 12*f* on a main-image display area 12*c* side. Further, the display unit 12 displays the mark 42*d* or 42*e* in the vicinity of the main-image display area 12*c* in response to the input of the operation information by the operation input unit 55, or changes the display color of the mark 42*a* or 42*b* in the in-vivo image P2, which is the operation target image.

Figure 25:
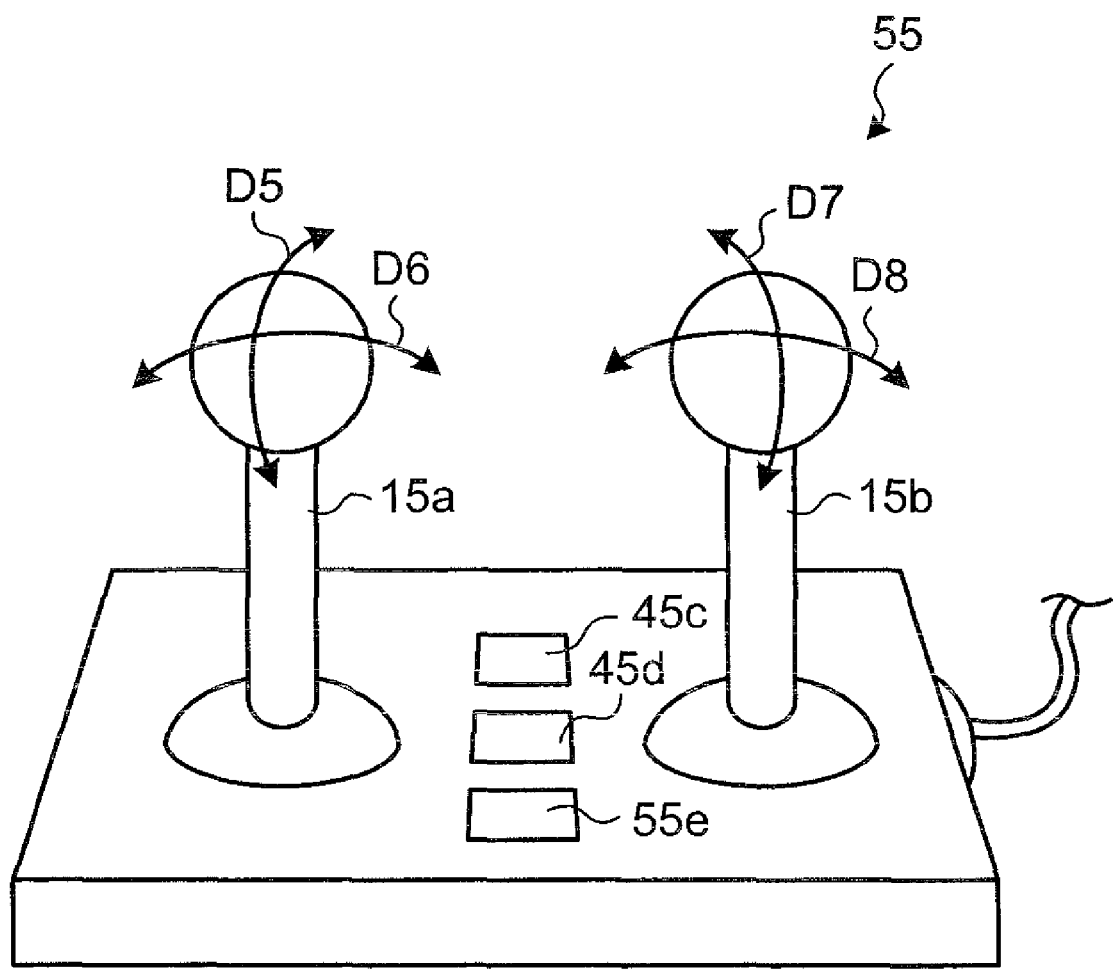
FIG. 25 is a schematic diagram showing one configuration example of the operation input unit of the fourth embodiment of the present invention.

The operation input unit 55 has an input function of the selection information to select the operation target image to be displayed on the image display device 53 in addition to the operation information to operate the magnetic guidance of the above-described capsule medical device 2 and the instruction information to the image display device 53. FIG. 25 is a schematic diagram showing one configuration example of the operation input unit in the fourth embodiment of the present invention. As shown in FIG. 25, the operation input unit 55 is provided with an input switch 55*e* in addition to the above-described joysticks 15*a* and 15*b* and the input switches 45*c* and 45*d*. The input switch 55*e* is the switch to input the selection information to select the operation target information from the in-vivo images P1 and P2 displayed by the image display device 53. The operation input unit 55 inputs the selection information of the operation target image to the controller 59 of the control device 56 in response to the push operation of the input switch 55*e*, and sequentially inputs the selection information to select the operation target image by switching between the in-vivo images P1 and P2 each time the push operation of the input switch 55*e* is performed. Specifically, the operation input unit 55 inputs the selection information to select the in-vivo image P1 as the operation target image to the controller 59 in response to the push operation of the input switch 55*e*, and inputs the selection information to select the in-vivo image P2 in the imaging direction different from that of the in-vivo image P1 as the operation target image to the controller 59 in response to the push operation of the input switch 55*e* thereafter. Meanwhile, the operation input unit 55 has the function similar to that of the operation input unit 45 in the above-described third embodiment, except for the information input function by the input switch 55*e*.

The control device 56 is provided with the controller 59 as described above to control the magnetic guidance device 3 to change the magnetic guidance direction of the capsule medical device 2 in response to the selection information of the operation target image input by the operation input unit 55 and controls the image display device 53 to switch the operation target image. Meanwhile, the control device 56 has the function similar to that of the control device 46 in the above-described third embodiment, except for the control function of the magnetic guidance device 3 and the image display device 53 in response to the selection information.

The controller 59 controls the magnetic guidance device 3 to change the magnetic guidance direction of the capsule medical device 2, which is the magnetic guidance target, in response to the switching of the operation target image in the above-described image display device 53. Specifically, the controller 59 obtains the selection information of the operation target image input by the operation input unit 55. The controller 59 controls the magnetic guidance device 3 to change at least one of the magnetic field direction of the guidance magnetic field and the moving direction of the bed 4 in the above-described absolute coordinate system to magnetically guide the capsule medical device 2 in response to the switches of the imaging direction of the operation target image selected by the selection information. Meanwhile, the imaging direction of the operation target image selected by such selection information is the operation target direction of the above-described capsule medical device 2, and is one of the imaging directions B1 and B2 of the imaging units 21 and 22, respectively, for example. The controller 59 controls the magnetic guidance of the capsule medical device 2 while maintaining the correspondence relation between the moving direction of the operation target image in the image display device 53 and the tilt direction of the joysticks 15*a* and 15*b* constant by changing the magnetic guidance direction of the capsule medical device 2 according to the input of the selection information in this manner.

Also, the controller 59 transmits the selection information of the operation target image input by the above-described operation input unit 55 to the controller 54 of the image display device 53. Thereby, the controller 59 controls the switching of the operation target image by the above-described image display device 53.

Meanwhile, the controller 59 has the function similar to that of the controller 49 of the control device 46 in the above-described third embodiment, except for the changing function of the magnetic guidance direction of the capsule medical device 2 and a function of switching controlling the operation target image according to the input of such selection information.

Figure 26:
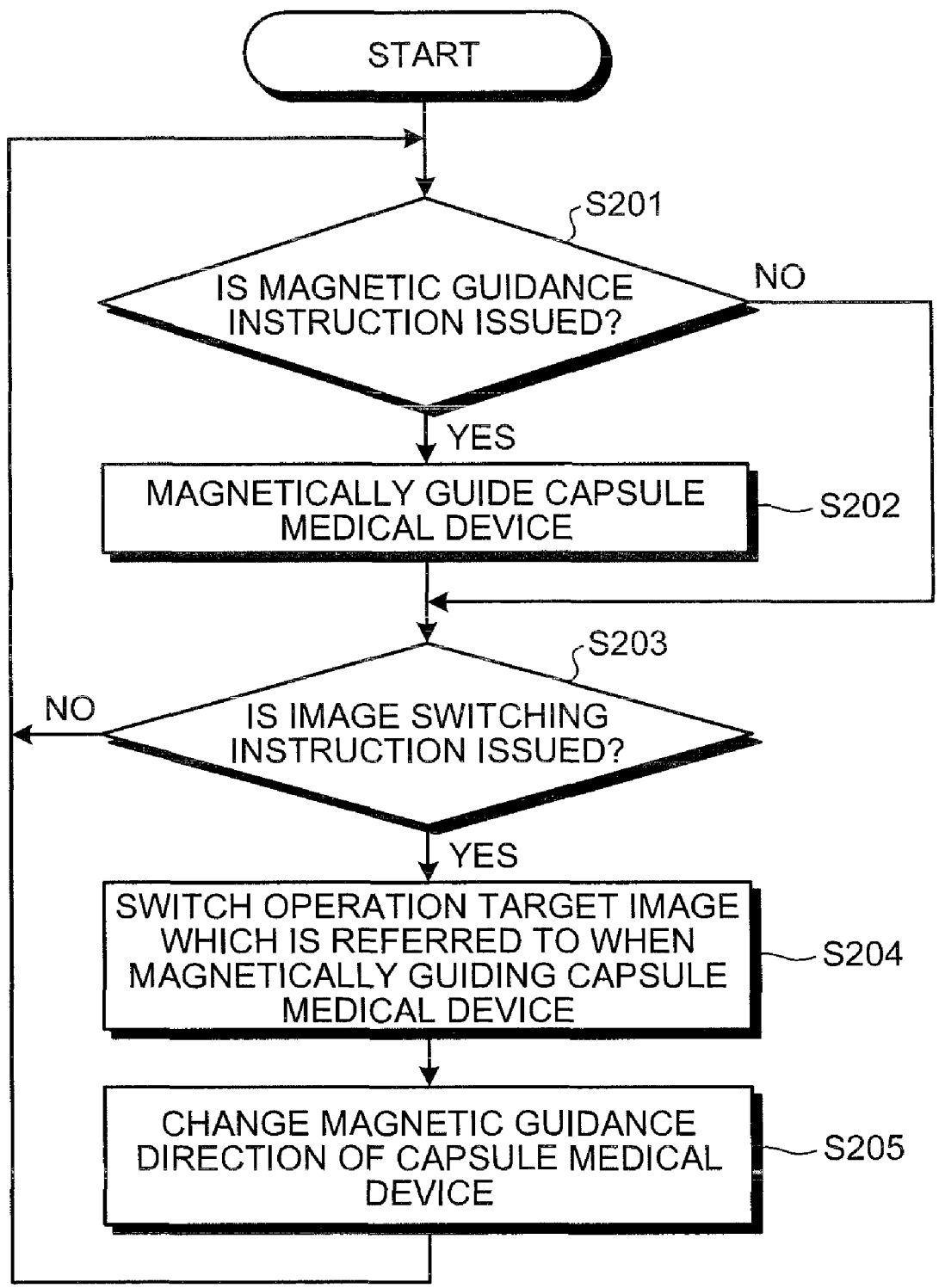
FIG. 26 is a flowchart showing one example of the procedure of a control device of the system for guiding capsule medical device according to the third embodiment of the present invention.

Next, the magnetic guidance control of the capsule medical device 2 by the control device 56 according to the third embodiment of the present invention is described. FIG. 26 is a flowchart showing one example of a procedure of the control device of the system for guiding capsule medical device according to the third embodiment of the present invention. FIG. 27 is a schematic diagram showing a state in which the image display device according to the third embodiment switches the operation target image.

The control device 56 controls the magnetic guidance of the capsule medical device 2 based on the above-described operation information, and when the selection information of the operation target image is input by the operation input unit 55, the control device 56 changes the magnetic guidance direction of the capsule medical device 2 in response to the selection information, and allows the image display device 53 to switch the operation target image.

Specifically, as shown in FIG. 26, the controller 59 of the control device 56 first judges whether the magnetic guidance instruction of the capsule medical device 2, which is the magnetic guidance target, is present (step S201). At the step S201, when the operation information is input by the operation input unit 55, the controller 59 judges that there is the magnetic guidance instruction of the capsule medical device 2 based on the operation information. On the other hand, when the operation information is not input by the operation input unit 55, the controller 59 judges that there is no magnetic guidance instruction of the capsule medical device 2.

When the controller 59 judges that there is the magnetic guidance instruction of the capsule medical device 2 at the step S201 (step S201, Yes), the controller 59 controls the magnetic guidance device 3 to magnetically guide the capsule medical device 2, which is the magnetic guidance target (step S202). At the step S202, the controller 59 controls the magnetic guidance device 3 to perform the magnetic guidance of the capsule medical device 2 according to the magnetic guidance direction and the magnetic guidance speed specified by the operation information obtained from the operation input unit 55. In this case, the controller 59 controls the magnetic field generator 5 to generate the guidance magnetic field necessary for the magnetic guidance of the capsule medical device 2 according to the magnetic guidance direction and the magnetic guidance speed based on the operation information. In addition, the controller 59 controls the drive unit 4a to perform parallel motion of the table portion of the bed 4 according to the magnetic guidance direction and the magnetic guidance speed based on the operation information. Also, the controller 59 controls the display unit 17 to display the elevation angle information, the direction angle information, and the location information of the capsule medical device 2 in a magnetic guidance state at the step S202 (refer to FIG. 11).

Meanwhile, at this moment, the image display device 53 displays the in-vivo images P1 and P2 of the subject 100 imaged by the imaging units 21 and 22, respectively, of the capsule medical device 2, and clearly shows the operation target image, which is one of the in-vivo images P1 and P2, as described above. Also, the image display device 53 displays the elevation angle information and the direction angle information of the capsule medical device 2 in the magnetic guidance state by relating them to the operation target image, which is one of the in-vivo images P1 and P2. Further, the image display device 53 displays the information indicating that the operation information is input by relating the same to the operation target image, in response to the input of the above-described operation information.

Next, the controller 59 judges presence of an image switching instruction of the operation target image at the time of the magnetic guidance of the capsule medical device 2 (step S203). At the step S203, when the selection information of the operation target image is input by the operation input unit 55, the controller 59 judges that there is the image switching instruction to the operation target image selected by the selection information. On the other hand, when the election information of the operation target image is not input by the operation input unit 55, the controller 59 judges that there is no image switching instruction of the operation target image.

When the controller 59 judges that there is the image switching instruction of the operation target image at the step S203 (step S203, Yes), the controller 59 transmits the selection information of the operation target image to the controller 54 of the image display device 53 to control the image display device 53 to switch the operation target image, which is referred to at the time of the magnetic guidance of the capsule medical device 2 (step S204). Also, the controller 59 controls the display unit 17 to change a marking location on the capsule pattern image E1 shown in above-described FIG. 11 to a location according to the imaging direction of the operation target image selected by the selection information, at the step S204. Thereby, the controller 59 allows the display unit 17 to display the operation target direction of the capsule medical device 2 corresponding to the selection information.

On the other hand, the image display device 53 obtains the selection information of the operation target image from the controller 59 at the step S204 to switch the operation target image to the in-vivo image selected by the obtained selection information, and switches the information display such as the elevation angle information and the direction angle information of the capsule medical device 2.

Specifically, when the in-vivo image P2 is selected by the selection information, the image display device 53 switches the operation target image from the in-vivo image P1, which is the operation target image at present, to the in-vivo image P2. In this case, the image display device 53 displays the frame image 32a displayed around the main-image display area 12b, around the main-image display area 12c, as shown in FIG. 27, thereby clearly showing the in-vivo image P2 in the main-image display area 12c as the operation target image. Also, the image display device 53 displays the marks 42a and 42b of the elevation angle information displayed in the in-vivo image P1, in the in-vivo image P2, which is the operation target image after the switching, thereby displaying the elevation angle information of the capsule medical device 2 by relating them to the in-vivo image P2. Further, the image display device 53 displays the direction information 42c displayed in the information display area 12e on the main-image display area 12b side, in the information display area 12f on the main-image display area 12c side, thereby displaying the direction angle information of the capsule medical device 2 by relating the same to the in-vivo image P2. In this case, the image display device 53 changes the operation target direction (that is to say, a direction of an arrow in the direction information 42c) of the capsule medical device 2 indicated by the direction information 42c in response to such switching of the operation target image. Also, the image display device 53 appropriately displays the marks 42d and 42e in the vicinity of the main-image display area 12c in response to the input of the operation information by the operation input unit 55, or changes the display color of the mark 42a or 42b in the in-vivo image P2. Thereby, the image display device 53 displays the information indicating that the operation information of the capsule medical device 2 is input by relating the same to the in-vivo image P2.

On the other hand, when the in-vivo image P1 is selected by the above-described selection information the image display device 53 switches the operation target image from the in-vivo image P2, which is the operation target image at present, to the in-vivo image P1. In this case, the image display device 53 displays the frame image 32a displayed around the main-image display area 12c, around the main-image display area 12b, as shown in FIG. 27, thereby clearly showing the in-vivo image P1 in the main-image display area 12b as the operation target image. Also, the image display device 53 displays the marks 42a and 42b of the elevation angle information displayed in the in-vivo image P2, in the in-vivo image P1, which is the operation target image after the switching, thereby displaying the elevation angle information of the capsule medical device 2 by relating the same to the in-vivo image P1. Further, the image display device 53 displays the direction information 42c displayed in the information display area 12f on the main-image display area 12c side, in the information display area 12e on the main-image display area 12b side, thereby displaying the direction angle information of the capsule medical device 2 by relating the same to the in-vivo image P1. In this case, the image display device 53 changes the operation target direction of the capsule medical device 2 indicated by the direction information 42c (that is to say, the direction of the arrow in the direction information 42c) in response to the switching of such an operation target image. Also, the image display device 53 appropriately displays the marks 42d and 42e in the vicinity of the main-image display area 12b in response to the input of the operation information by the operation input unit 55, or changes the display color of the mark 42a or 42b in the in-vivo image P1. Thereby, the image display device 53 displays the information indicating that the operation information of the capsule medical device 2 is input by relating the same to the in-vivo image P1.

After carrying out the above-described step S204, the controller 59 controls the magnetic guidance device 3 to change the magnetic guidance direction of the capsule medical device 2, which is the magnetic guidance target, in response to the selection information input by the operation input unit 55 at the above-described step S203 (step S205). At the step S205, the controller 59 controls the magnetic guidance device 3 to change at least one of the magnetic field direction of the guidance magnetic field and the moving direction of the bed 4 in the above-described absolute coordinate system to magnetically guide the capsule medical device 2 in response to the switching of the imaging direction of the operation target image selected by the input selection information. Thereby, the controller 59 controls the magnetic guidance of the capsule medical device 2 while maintaining the correspondence relation between the moving direction of the operation target image in the image display device 53 and the tilt direction of the operation input unit 55 constant.

Specifically, when the imaging directions B1 and B2 of the imaging units 21 and 22, respectively, of the capsule medical device 2, which is the magnetic guidance target, are opposite to each other as shown in FIG. 3, and the upper side of the imaging surface of the imaging unit 21 and the upper side of the imaging surface of the imaging unit 22 are on the same side, the controller 59 changes the magnetic guidance direction, which is parallel to the operation target direction (that is to say, the imaging direction of the operation target image) of the capsule medical device 2, to an opposite direction before and after the switching of the above-described operation target image. Also, the controller 59 changes the magnetic guidance direction, which is parallel to the right and left direction of the imaging units 21 and 22, to the opposite direction before and after the switching of the above-described operation target image, and makes the magnetic guidance direction, which is parallel to the upward and downward directions D2 and D3 of the imaging units 21 and 22, respectively, the same direction (that is to say, the controller 59 does not change the magnetic guidance direction). Further, the controller 59 changes the magnetic guidance direction in the swaying motion of the capsule medical device 2, that is to say, the swaying motion direction of the capsule medical device 2 by the magnetic guidance to the opposite direction before and after the switching of the above-described operation target image to make the magnetic guidance direction in the turning motion of the capsule medical device 2, that is to say, the turning motion direction of the capsule medical device 2 by the magnetic guidance, the same direction. On the other hand, when the imaging directions B1 and B2 of the imaging units 21 and 22, respectively, of the capsule medical device 2, which is the magnetic guidance target, are opposite to each other as shown in FIG. 3, and the upper side of the imaging surface of the imaging unit 21 and the upper side of the imaging surface of the imaging unit 22 are opposite to each other, the controller 59 changes the magnetic guidance direction, which is parallel to the operation target direction of the capsule medical device 2, to the opposite direction before and after the switching of the above-described operation target image. Also, the controller 59 makes the magnetic guidance direction, which is parallel to the right and left direction of the imaging units 21 and 22, the same direction before and after the switching of the above-described operation target direction, and changes the magnetic guidance direction, which is parallel to the upward and downward directions D2 and D3 of the imaging units 21 and 22, respectively, to the opposite direction. Further, the controller 59 makes the magnetic guidance direction in the swaying motion of the capsule medical device 2 the same direction and changes the magnetic guidance direction in the turning motion of the capsule medical device 2 to the opposite directions before and after the switching of the above-described operation target image.

After carrying out the above-described step S205, the controller 59 returns to the step S201 and repeats the procedure after the step S201. On the other hand, when the controller 59 judges that there is no magnetic guidance instruction of the capsule medical device 2 at the step S201 (step S201, No), the controller 59 proceeds to the step S203 to repeat the procedure after the step S203. Also, when the controller 59 judges that there is no image switching instruction of the operation target image at the step S203 (step S203, No), the controller 59 returns to the step S201 to repeat the procedure after the step S201.

As described above, in the system for guiding capsule medical device according to the fourth embodiment of the present invention, it is configured that the operation target image at the time of the magnetic guidance of the capsule medical device is switched between the in-vivo images imaged by the imaging units in the capsule medical device, the in-vivo image to be clearly shown as the operation target image is changed in response to such switching of the operation target image and the display of the elevation angle information and the direction angle information of the capsule medical device are switched, and further, the magnetic guidance direction of the capsule medical device is changed according to the imaging direction of the operation target image after the switching, and other configurations are made the same as those in the third embodiment. Therefore, the system for guiding capsule medical device capable of enjoying the effect as in the case of the above-described third embodiment, and of magnetically guiding the capsule medical device while maintaining the correspondence relation between the moving direction of the operation target image and the tilt direction of the operation input unit constant before and after the switching of the operation target image referred to at the time of the magnetic guidance of the capsule medical device constant, thereby easily operating the magnetic guidance of the capsule medical device in the subject while referring to the desired in-vivo image among a plurality of the in-vivo images in the display screen can be realized.

Also, even when the operation target image is switched between a plurality of in-vivo images, the elevation angle information, the direction angle information, and the information indicating that the operation information is input, of the capsule medical device are switched and displayed in response to such switching of the operation target image, so that the imaging direction and the magnetic guidance direction of the capsule medical device in the subject can be easily visually recognized while referring to the operation target image after the switching. As a result, the magnetic guidance of the capsule medical device in the subject can be easily operated while observing the in-vivo image necessary for the examination in organ of the subject.

Next, a fifth embodiment of the present invention is described. Although the capsule medical device 2 is magnetically guided in the horizontal axis direction, that is to say, in the x-axis direction or in the y-axis direction of the absolute coordinate system regardless of the position of the capsule medical device 2 in the liquid 101, when magnetically guiding the capsule medical device 2 in the subject 100 in the horizontal direction in the above-described first to fourth embodiments, the capsule medical device 2 may be magnetically guided in the direction of the long axis 27 of the capsule medical device 2 and in a direction perpendicular to the long axis 27 (that is to say, a radial direction of the capsule medical device 2) in the fifth embodiment.

Figure 28:
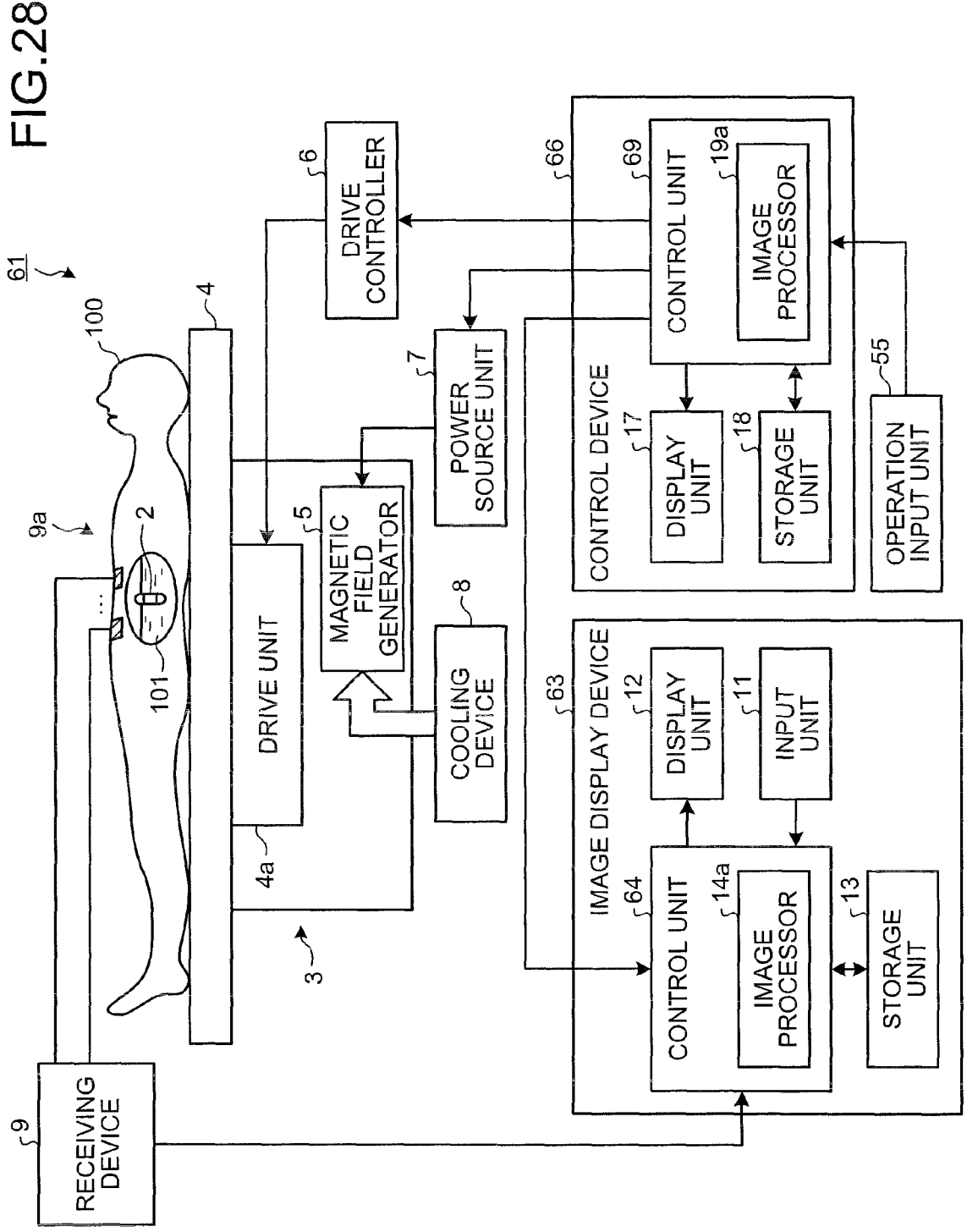
FIG. 28 is a block diagram schematically showing one configuration example of the system for guiding capsule medical device according to a fifth embodiment of the present invention.

FIG. 28 is a block diagram schematically showing one configuration example of the system for guiding capsule medical device according to the fifth embodiment of the present invention. As shown in FIG. 28, a system for guiding capsule medical device 61 according to the fifth embodiment is provided with an image display device 63 in place of the image display device 53 of the system for guiding capsule medical device 51 according to the above-described fourth embodiment, and a control device 66 in place of the control device 56. In the fifth embodiment, the image display device 63 is provided with a controller 64 in place of the controller 54 of the image display device 53 according to the above-described fourth embodiment. Also, the control device 66 is provided with a controller 69 in place of the controller 59 of the control device 56 according to the above-described fourth embodiment. Other configurations are the same as those of the fourth embodiment, and the same reference numerals are given to the same components.

The image display device 63 is provided with the controller 64 as described above to display the information indicating that the operation information corresponding to the magnetic guidance in the direction of the long axis 27 or in the radial direction of the capsule medical device 2 is input by relating the same to the operation target image. Meanwhile, the image display device 63 has the function similar to that of the image display device 53 in the above-described fourth embodiment, except for the function of displaying the information indicating that such operation information is input.

The controller 64 allows the display unit 12 to display the information indicating that the operation information corresponding to the magnetic guidance in the direction of the long axis 27 or in the radial direction of the capsule medical device 2 is input. Specifically, the controller 64 receives notification that the operation information to operate the magnetic guidance in the direction of the long axis 27 or in the radial direction of the capsule medical device 2 is input by the operation input unit 55 from the controller 69 of the control device 66. The controller 64 controls the display unit 12 to display the information indicating that the operation information corresponding to the magnetic guidance in the direction of the long axis 27 or in the radial direction of the capsule medical device 2 is input by relating the same to the operation target image out of the above-described in-vivo images P1 and P2 based on the notification of the input. Meanwhile, the controller 64 has the function similar to that of the controller 54 of the image display device 53 in the above-described fourth embodiment, except for the display control function of the information indicating that such operation information is input.

On the other hand, the control device 66 is provided with the controller 69 as described above to allow the magnetic guidance device 3 to perform the magnetic guidance in the direction of the long axis 27 or in the radial direction of the capsule medical device 2. Meanwhile, the control device 66 has the function similar to that of the control device 56 in the above-described fourth embodiment, except for the function of controlling the magnetic guidance in the direction of the long axis 27 or in the radial direction of the capsule medical device 2.

The controller 69 controls the magnetic guidance device 3 to magnetically guide the capsule medical device 2 in the direction of the long axis 27 or in the radial direction of the capsule medical device 2 based on the operation information input by the above-described operation input unit 55. In this case, the controller 69 controls the magnetic field strength and the magnetic field direction of the guidance magnetic field by the magnetic field generator 5 and the moving direction and the moving amount of the bed 4 by the drive unit 4a, and allows the magnetic guidance device 3 to perform the magnetic guidance in the direction of the long axis 27 or in the radial direction of the capsule medical device 2 by combination of each control with respect to the magnetic field generator 5 and the drive unit 4a. Here, in the fifth embodiment, the magnetic guidance direction specified by the operation information input by the operation input unit 55 is around the vertical axis, around the horizontal axis, and the direction of the long axis 27 and the radial direction of the capsule medical device 2. Also, the direction of the long axis 27 of the capsule medical device 2 includes the imaging direction of the imaging unit 21 or 22 (that is to say, the imaging direction of the operation target image) for example, and the radial direction of the capsule medical device 2 includes the upward and downward direction and right and left direction of the imaging surface of the imaging unit 21 or 22, for example.

Meanwhile, the controller 69 controls the magnetic guidance device 3 as is the case with the controller 59 of the control device 56 in the above-described fourth embodiment for the magnetic guidance of the capsule medical device 2 around the vertical axis and the magnetic guidance of the capsule medical device 2 around horizontal axis. Also, the controller 69 has the function similar to that of the controller 59 of the control device 56 in the above-described fourth embodiment, except for the function of controlling the magnetic guidance of the capsule medical device 2.

Figure 29:
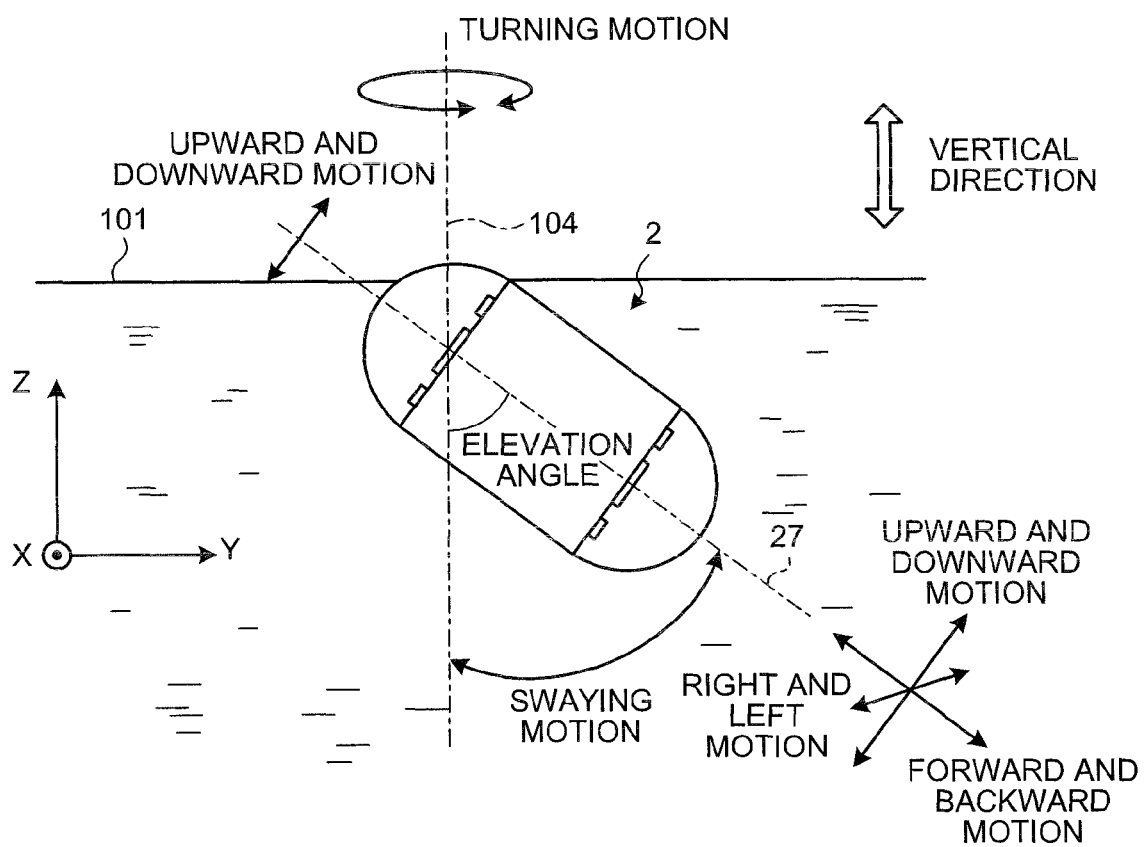
FIG. 29 is a schematic diagram illustrating the magnetic guidance of the system for guiding capsule medical device of the fifth embodiment of the present invention.

Next, the magnetic guidance of the capsule medical device 2 controlled by the control device 66 in the fifth embodiment of the present invention is described. FIG. 29 is a schematic diagram illustrating the magnetic guidance of the capsule medical device of the fifth embodiment of the present invention.

In the fifth embodiment, the operation input unit 55 determines the magnetic guidance direction of the capsule medical device 2 in the direction of the long axis 27, that is to say, the imaging direction of the operation target image out of the imaging directions B1 and B2 of the imaging units 21 and 22, respectively, in response to the tilt operation of the joystick 15*a* in the upward and downward direction D5 shown in FIG. 25, and determines the motion speed of the capsule medical device 2 in the direction of the long axis 27 in response to the tilt operation amount in the upward and downward direction D5. In this case, the operation input unit 55 inputs the operation information to specify the direction of the long axis 27 as the magnetic guidance direction of the capsule medical device 2 and to specify the motion speed of the capsule medical device 2 in the direction of the long axis 27 to the controller 69 of the control device 66.

Also, the operation input unit 55 determines the magnetic guidance direction of the capsule medical device 2 in the radial direction of the capsule medical device 2, that is to say, the right and left direction of the imaging surface of the imaging unit 21 or 22 in response to the tilt operation of the joystick 15*a* in the right and left direction D6 shown in FIG. 25, and determines the motion speed of the capsule medical device 2 in the right and left direction of the imaging surface in response to the tilt operation amount in the right and left direction D6. In this case, the operation input unit 55 inputs the operation information to specify the right and left direction of the imaging surface as the magnetic guidance direction of the capsule medical device 2 and to specify the motion speed of the capsule medical device 2 in the right and left direction of the imaging surface to the controller 69 of the control device 66.

On the other hand, the operation input unit 55 determines the magnetic guidance direction of the capsule medical device 2 in the radial direction of the capsule medical device 2, that is to say, the upward and downward direction of the imaging surface of the imaging unit 21 or 22 in response to a simultaneous tilt operation of two joysticks 15*a* and 15*b* in the upward and downward directions D5 and D7, respectively, and determines the motion speed of the capsule medical device 2 in the upward and downward direction of the imaging surface in response to the tilt operation amount in the upward and downward directions D5 and D7. In this case, the operation input unit 55 inputs the operation information to specify the upward and downward direction of the imaging surface as the magnetic guidance direction of the capsule medical device 2, and to specify the motion speed of the capsule medical device 2 in the upward and downward direction of the imaging surface to the controller 69 of the control device 66.

Meanwhile, the operation information corresponding to the magnetic guidance of the capsule medical device 2 around the vertical axis and the operation information corresponding to the magnetic guidance of the capsule medical device 2 in the horizontal axis are input to the controller 69 of the control device 66 by the operation input unit 55 as in the case of the above-described fourth embodiment.

The controller 69 of the control device 66 controls the magnetic guidance device 3 to perform the magnetic guidance of the capsule medical device 2 according to the magnetic guidance direction and the magnetic guidance speed specified by the operation information from the operation input unit 55. Specifically, the controller 69 controls the magnetic field strength and the magnetic field direction of the guidance magnetic field by the magnetic field generator 5 and the moving direction and the moving amount of the bed 4 by the drive unit 4*a* so as to perform the magnetic guidance of the capsule medical device 2 at the magnetic guidance speed specified by the operation information in the imaging direction B1 of the imaging unit 21 or the imaging direction B2 of the imaging unit 22, which are parallel to the long axis 27 of the capsule medical device 2. Alternatively, the controller 69 controls the magnetic field strength and the magnetic field direction of the guidance magnetic field by the magnetic field generator 5 and the moving direction and the moving amount of the bed 4 by the drive unit 4*a* so as to perform the magnetic guidance of the capsule medical device 2 at the magnetic guidance speed specified by the operation information in the radial direction of the capsule medical device 2, that is to say, in the upward and downward direction or the right and left direction of the imaging surface of the imaging unit 21 or 22.

The capsule medical device 2 performs various motions according to the magnetic guidance by the magnetic guidance device 3 in the liquid 101 in the subject 100. Specifically, as shown in FIG. 29, the capsule medical device 2 in the liquid 101 performs forward and backward motion to move forward or backward in the direction of the long axis 27 (that is to say, the imaging direction of the operation target image) in response to the tilt operation of the above-described joystick 15*a* in the upward and downward direction D5. Also, the capsule medical device 2 in the liquid 101 performs the right and left motion to move in the radial direction of the capsule medical device 2, in detail, in the right and left directions of the imaging surface (that is to say, one of the image surfaces of the imaging units 21 and 22) of the operation target image in response to the tilt operation of the above-described joystick 15*a* in the right and left direction D6. Also, the capsule medical device 2 in the liquid 101 performs the upward and downward motion to move in the radial direction of the capsule medical device 2, in detail, in the upward and downward direction of the imaging surface of the operation target image, in response to the simultaneous tilt operation of the above-described joysticks 15*a* and 15*b*.

Figure 30:
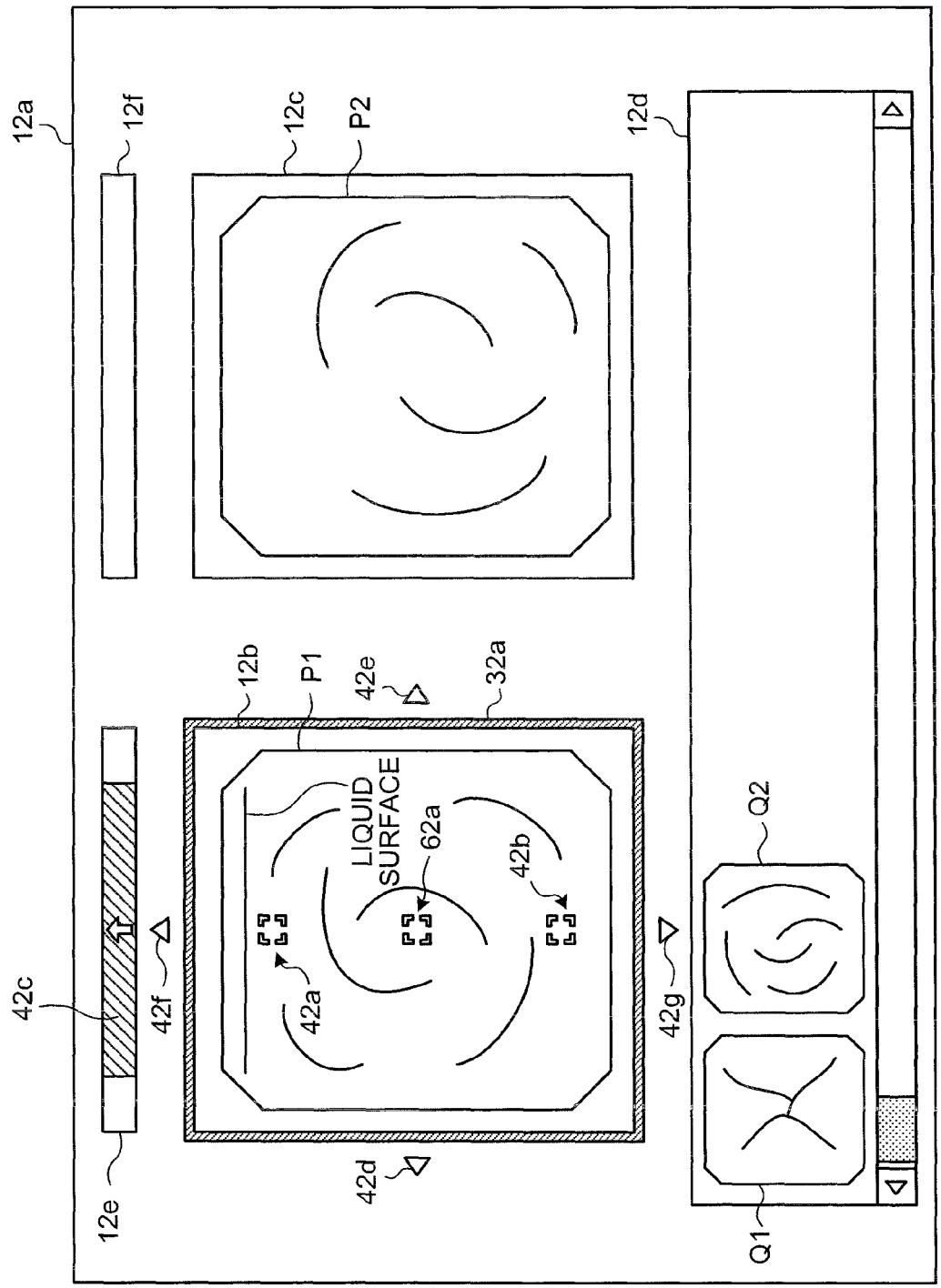
FIG. 30 is a schematic diagram showing one example of the display mode of the image display device according to the fifth embodiment of the present invention.

Next, a display process of the information indicating that the operation information is input, by the image display device 63 of the fifth embodiment of the present invention is described. FIG. 30 is a schematic diagram showing one example of the display mode of the image display device according to the fifth embodiment.

The image display device 63 displays the information indicating that the operation information of the capsule medical device 2 is input by the operation input unit 55 by relating the same to the operation target image out of the above-described in-vivo images P1 and P2. In this case, the controller 64 of the image display device 63 receives the notification indicating that the operation information of the capsule medical device 2 is input by the operation input unit 55 from the controller 69 of the control device 66, as described above, to control the display unit 12 to display the information indicating that the operation information is input based on the notification.

The display unit 12 displays the information indicating that the operation information corresponding to the magnetic guidance in the direction of the long axis 27 or in the radial direction of the capsule medical device 2 is input by relating the same to the in-vivo image P1, which is the operation target image out of the in-vivo images P1 and P2, as shown in FIG. 30, for example, based on the control of the controller 64. In this case, the display unit 12 displays any of the marks 42*d* to 42*f* in the vicinity of the main-image display area 12*b*, or changes the display color of the mark 62*a* displayed in the in-vivo image P1, which is the operation target image.

Here, the mark 42*d* is the information indicating that the operation information of the magnetic guidance to allow the capsule medical device 2 to perform the motion to the left of the right and left motion of the capsule medical device 2 shown in FIG. 29 relative to the operation target direction (the imaging direction B1, for example) of the capsule medical device 2 is input. Also, the mark 42*e* is the information indicating that the operation information of the magnetic guidance to allow the capsule medical device 2 to perform the motion to the right of the right and left motion of the capsule medical device 2 shown in FIG. 29 relative to the operation target direction of the capsule medical device 2 is input. On the other hand, the mark 42*f* is the information indicating that the operation information of the magnetic guidance to allow the capsule medical device 2 to perform the motion in an upper direction of the upward and downward motion of the capsule medical device 2 shown in FIG. 29 relative to the operation target direction of the capsule medical device is input. Also, the mark 42*g* is the information indicating that the operation information of the magnetic guidance to allow the capsule medical device 2 to perform the motion in a lower direction of the upward and downward motion of the capsule medical device shown in FIG. 29 relative to the operation target direction of the capsule medical device 2 is input. On the other hand, the mark 62*a* is the information indicating that the operation information of the magnetic guidance to allow the capsule medical device 2 to perform the forward and backward motion of the capsule medical device 2 shown in FIG. 29 is input.

When the joystick 15*a* of the operation input unit 55 is operated so as to tilt to the left out of the right and left direction D6, the display unit 12 displays the mark 42*d* in the vicinity of the left side of the main-image display area 12*b* and on the central line of the in-vivo image P1 as shown in FIG. 30. Also, when the joystick 15*a* of the operation input unit 55 is operated so as to tilt to the right out of the right and left direction D6, the display unit 12 displays the mark 42*e* in the vicinity of the right side of the main-image display area 12*b* and on the central line of the in-vivo image P1. On the other hand, when the joysticks 15*a* and 15*b* of the operation input unit 55 are simultaneously operated so as to tilt to the back side, the display unit 12 displays the mark 42*f* in the vicinity of the upper side of the main-image display area 12*b* as shown in FIG. 30. Also, when the joysticks 15*a* and 15*b* of the operation input unit 55 are simultaneously operated to tilt to the front side, the display unit 12 displays the mark 42*g* in the vicinity of the lower side of the main-image display area 12*b* as shown in FIG. 30.

On the other hand, the display unit 12 displays the mark 62*a* in the in-vivo image P1, which is the operation target image, and on the central location between the marks 42*a* and 42*b* of the above-described elevation angle information, as shown in FIG. 30. The display unit 12 displays the marks 42*a*, 42*b*, and 62*a* in the in-vivo image P1 by arranging them in one line lengthwise. The display unit 12 moves the mark 62*a* together with the marks 42*a* and 42*b* while maintaining the space between the same and the marks 42*a* and 42*b* constant based on the control of the controller 64.

Here, when the joystick 15*a* of the operation input unit 55 is operated to tilt in the upward and downward direction D5, the display unit 12 changes the display color of the mark 62*a* in the in-vivo image P1 from the default color (such as yellow) to another color (such as blue). Thereby, the display unit 12 displays the information indicating that the operation information corresponding to the tilt operation of the joystick 15*a*, that is to say, the operation information of the magnetic guidance to allow the capsule medical device 2 to perform the forward and backward motion of the capsule medical device 2 as shown in FIG. 29 is input.

Meanwhile, the display unit 12 may always display the marks 42*d* to 42*g* in the vicinity of the main-image display area 12*b* with the predetermined color (such as white) regardless of the presence of the input of the operation information by the operation input unit 55, and when such operation information is input, the display unit 12 may display by changing the color of the mark corresponding to the operation information out of the marks 42*d* to 42*g* to another color (such as yellow).

Also, in above-described FIG. 30, as one example, although the in-vivo image P1 by the imaging unit 21 is the operation target image, and the marks 42*a* and 42*b* of the elevation angle information, the direction information 42*c*, and the marks 42*d* to 42*f* and 62*a* are displayed by being related to the in-vivo image P1, the present invention is not limited to this. That is to say, the in-vivo image P2 by the imaging unit 22 may be the operation target image, and in this case, the display unit 12 may display the above-described marks 42*a* and 42*b* of the elevation angle information, the direction information 42*c*, and the marks 42*d* to 42*g* and 62*a* by relating them to the in-vivo image P2, which is the operation target image. Meanwhile, each display process of the marks 42*a* and 42*b* of the elevation angle information, the direction information 42*c*, and the frame image 32*a* by the display unit 12 is similar to that in the case of the above-described fourth embodiment.

As described above, in the system for guiding capsule medical device according to the fifth embodiment of the present invention, the capsule medical device is magnetically guided in the long axis direction or in the radial direction of the capsule medical device, and the information indicating that the operation information of the magnetic guidance is input is displayed by being related to the operation target image, and other configurations are made the same as those in the case of the fourth embodiment. Therefore, the system for guiding capsule medical device capable of enjoying the effect similar to that of the above-described fourth embodiment, and of easily magnetically guiding the capsule medical device in the subject based on the imaging direction of the operation target image, which is referred to when operating the magnetic guidance of the capsule medical device can be realized.

Next, a sixth embodiment of the preset invention is described. The system for guiding capsule medical device according to the sixth embodiment allows a temporal swaying motion of the capsule medical device 2 by an applied magnetic field before magnetically guiding the capsule medical device 2 in a state floating on a liquid surface downward from the liquid surface, thereby eliminating the effect of surface tension of the liquid surface on the capsule medical device 2.

Figure 31:
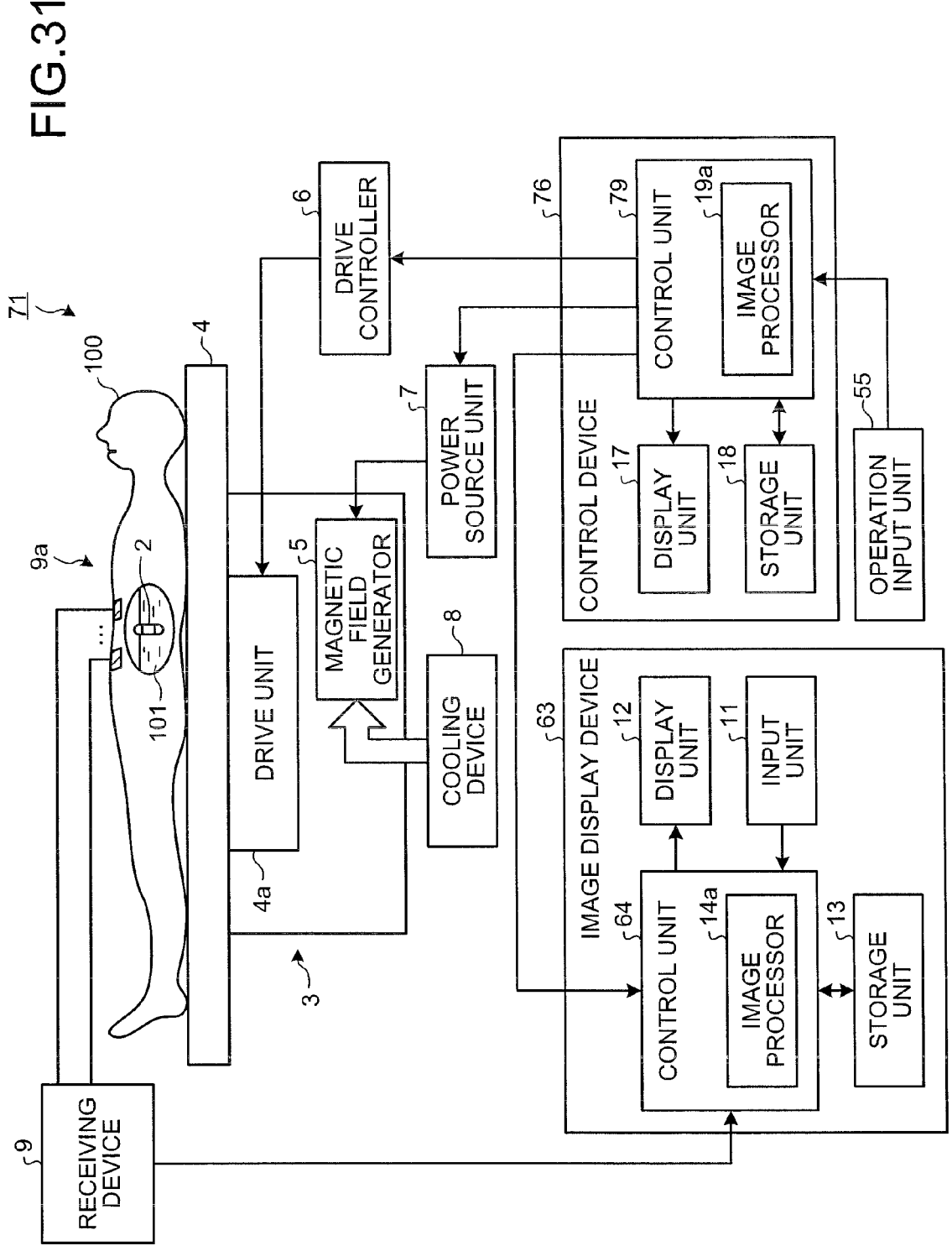
FIG. 31 is a block diagram schematically showing one configuration example of the system for guiding capsule medical device according to a sixth embodiment of the present invention.

FIG. 31 is a block diagram schematically showing one configuration example of the system for guiding capsule medical device according to the sixth embodiment of the present invention. As shown in FIG. 31, a system for guiding capsule medical device 71 according to the sixth embodiment is provided with a control device 76 in place of the control device 66 of the system for guiding capsule medical device 61 according to the above-described fifth embodiment. In the sixth embodiment, the control device 76 is provided with a controller 79 in place of the controller 69 of the control device 66 according to the above-described fifth embodiment. Other configurations are the same as those of the fifth embodiment, and the same reference numerals are given to the same components.

The control device 76 is provided with the controller 79 as described above to control the magnetic guidance device 3 to eliminate the surface tension of the liquid surface acting on the capsule medical device 2 in the state floating on the liquid surface before magnetically guiding the capsule medical device 2 in the subject 100 downward from the liquid surface of the liquid 101. The control device 76 controls the magnetic guidance device 3 to magnetically guide the capsule medical device 2 in the state released from the effect of surface tension of the liquid surface in this manner under the liquid surface. Meanwhile, the control device 76 has the function similar to that of the control device 66 in the above-described fifth embodiment except an elimination control function of the surface tension of the liquid acting on the capsule medical device 2.

When the magnetic guidance of the capsule medical device 2 downward from the liquid surface of the liquid 101 is specified by the operation information from the operation input unit 55, the controller 79 controls the magnetic guidance device 3 to eliminate the effect of surface tension of the liquid surface on the capsule medical device 2 based on the operation information, and controls the magnetic guidance device 3 to magnetically guide the capsule medical device 2 in the state released from the effect of surface tension of the liquid surface downward from the liquid surface. In this case, the controller 79 controls the magnetic field generator 5 to apply an elimination magnetic field to eliminate the effect of surface tension of the liquid surface on the capsule medical device 2 to the capsule medical device 2, and controls the elimination of the surface tension of the liquid surface on the capsule medical device 2 through the control of the magnetic field generator 5. Meanwhile, the controller 79 has the function similar to that of the controller 69 of the control device 66 in the above-described fifth embodiment, except for the elimination control function of the surface tension of the liquid surface on the capsule medical device 2.

Figure 32:
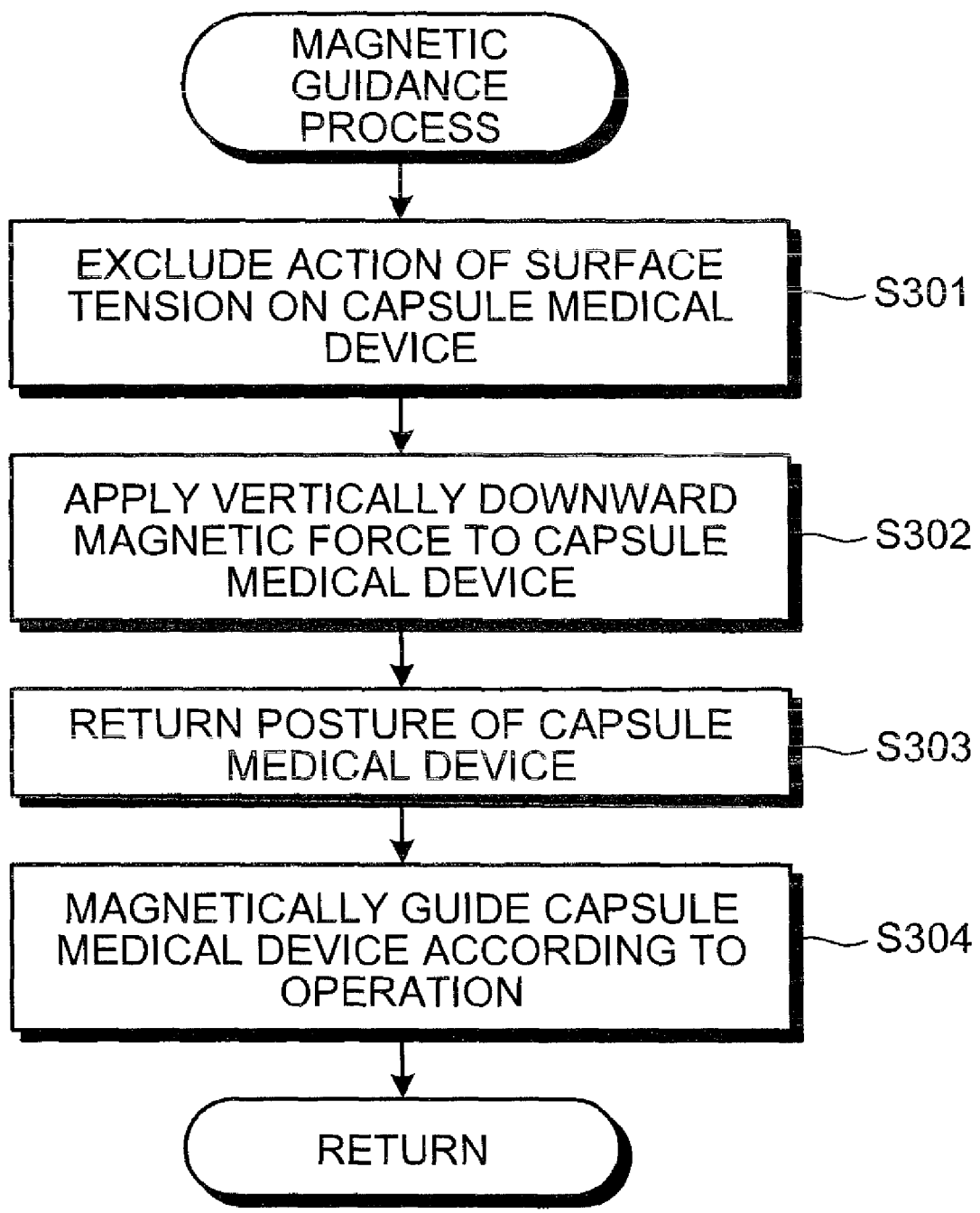
FIG. 32 is a flowchart showing one example of the procedure of the control device when magnetically guiding the capsule medical device in a state floating on a liquid surface under the liquid surface.
Figure 33:
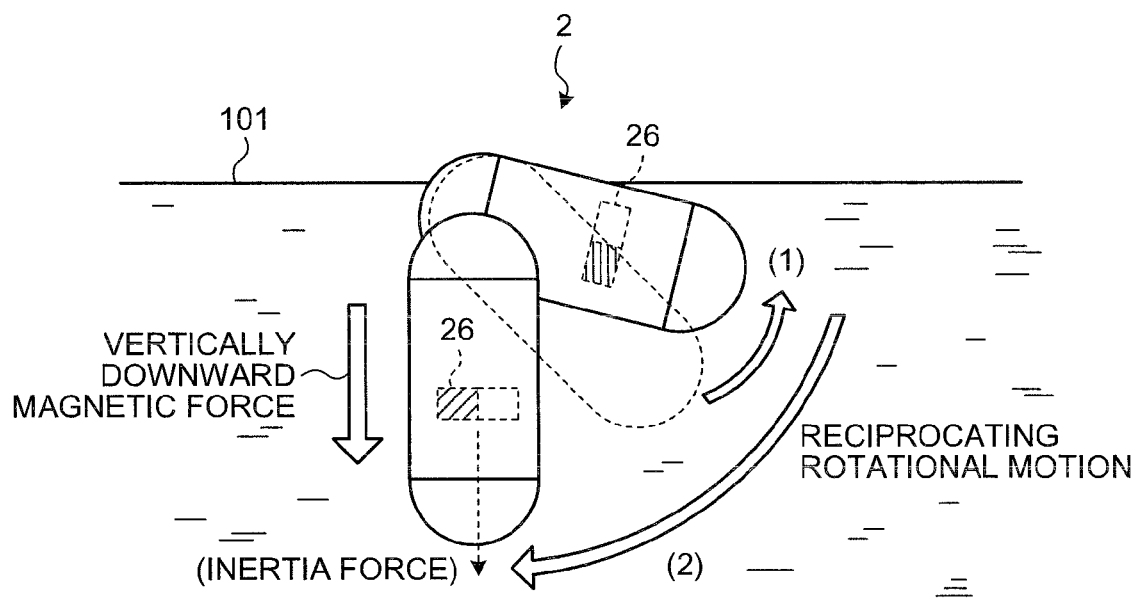
FIG. 33 is a schematic diagram showing a state in which an effect of surface tension of the liquid surface on the capsule medical device is eliminated.
Figure 34:
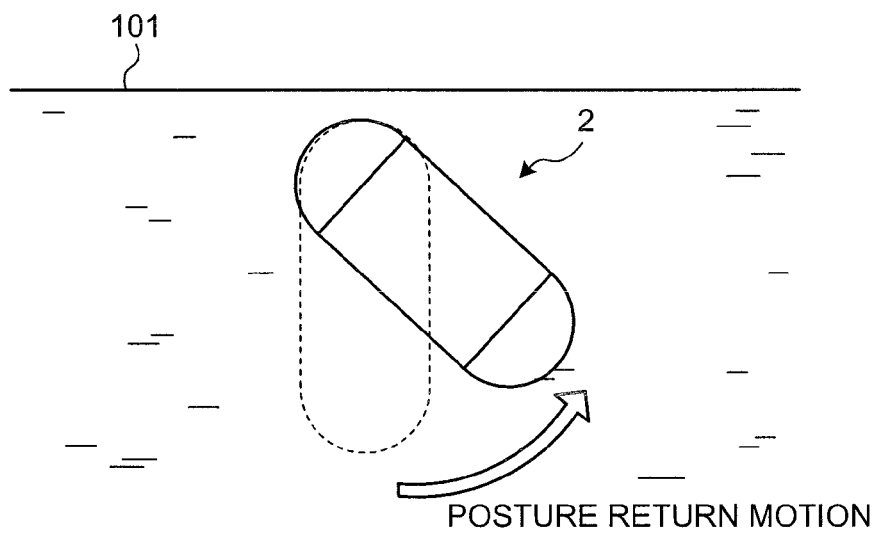
FIG. 34 is a schematic diagram showing a state a position of the capsule medical device in the liquid is returned.

Next, the magnetic guidance control of the capsule medical device 2 by the control device 76 according to the sixth embodiment of the present invention is described. FIG. 32 is a flowchart showing one example of the procedure of the control device when magnetically guiding the capsule medical device in the state floating on the liquid surface downward from the liquid surface. FIG. 33 is a schematic diagram showing a state in which the effect of surface tension of the liquid surface on the capsule medical device is eliminated. FIG. 34 is a schematic diagram showing a state of returning the position of the capsule medical device in the liquid.

The control device 76 controls the magnetic guidance device 3 to magnetically guiding the capsule medical device 2 under the liquid surface after eliminating the effect of surface tension of the liquid surface on the capsule medical device 2 in the state floating on the liquid surface of the liquid 101 at the step S202 shown in above-described FIG. 26.

That is to say, as shown in FIG. 32, the controller 79 of the control device 76 controls the magnetic guidance device 3 to eliminate the effect of surface tension of the liquid surface on the capsule medical device 2 in the state floating on the liquid surface before magnetically guiding the capsule medical device 2 in the subject 100 under the liquid surface of the liquid 101 (step S301).

At the step S301, the controller 79 controls the magnetic field generator 5 to generate the elimination magnetic field to eliminate the effect of surface tension of the liquid surface on the capsule medical device 2. Here, the elimination magnetic field is a rotating magnetic field reciprocally rotating around the horizontal axis at a predetermined rotation frequency (0.5 to 3 Hz, for example) and is applied to the capsule medical device 2 aside from the above-described guidance magnetic field control by the controller 79. The magnetic field generator 5 applies the elimination magnetic field to the capsule medical device 2 based no the control by the controller 79, thereby eliminating the effect of surface tension of the liquid surface on the capsule medical device 2.

By the effect of such an elimination magnetic field, the capsule medical device 2 in the floating state sinks under the liquid surface of the liquid 101 while temporally changing the position thereof. Specifically, the capsule medical device 2 in the state floating on the liquid surface of the liquid 101 incorporates the permanent magnet 26 as described above, and performs the reciprocating rotational motion around the horizontal axis in numeric order shown in FIG. 33 following the elimination magnetic field by the magnetic field generator 5. In this case, the capsule medical device 2 in the floating state performs the reciprocating rotational motion at the rotation frequency of 0.5 to 3 Hz, for example, thereby changing the position thereof at high speed and generating vertically downward inertial force. The capsule medical device 2 in the floating state temporally sinks under the liquid surface by such a vertically downward inertial force, and consequently is released from the effect of surface tension of the liquid surface.

After carrying out the procedure at the above-described step S301, the controller 79 controls the magnetic field generator 5 to apply vertically downward magnetic force to the capsule medical device 2 in the state released from the effect of surface tension of the liquid surface (step S302). At the step S302, the magnetic field generator 5 applies the vertically downward magnetic field to the capsule medical device 2 in the state released from the surface tension, that is to say, the capsule medical device 2 in a state temporally sinking under the liquid surface of the liquid 101 by the effect of the above-described elimination magnetic field, based on the control of the controller 79. Thereby, the magnetic field generator 5 applies vertically downward magnetic attraction force to the capsule medical device 2 under the liquid surface, and maintains the capsule medical device 2 at the location in the vicinity of the liquid surface under the liquid surface by the effect of the magnetic attraction force as shown in FIG. 33. Meanwhile, it is desirable that the vertically downward magnetic field by the magnetic field generator 5 is the magnetic field having the magnetic force enough to cancel out difference between gravity force and floating force acting on the capsule medical device 2.

Thereafter, the controller 79 controls the magnetic field generator 5 to return the position of the capsule medical device 2 of which position is changed at the step S301 to the state before eliminating the surface tension effect (step S303). At the step S303, the magnetic field generator 5 applies the magnetic field to return the position to the capsule medical device 2 under the liquid surface based on the control of the controller 79. Specifically, the magnetic field generator 5 applies the magnetic field in the same magnetic field direction as that of the guidance magnetic field applied to the capsule medical device 2 just before applying the magnetic field for eliminate the surface tension effect to the capsule medical device in the floating state at the above-described step S301 to the capsule medical device 2 under the liquid surface as the magnetic field to return the position. Thereby, the magnetic field generator 5 returns the position of the capsule medical device 2 under the liquid surface to the position before eliminating the surface tension effect (position indicated by a broken line in FIG. 33).

The capsule medical device 2 under the liquid surface returns the position before eliminating the surface tension effect by the effect of the magnetic field to return the position. Specifically, as shown in FIG. 34, the capsule medical device 2 under the liquid surface performs the position returning motion such as the swaying motion following such a magnetic field to return the position, thereby recreating the position just before the above-described elimination magnetic field is applied (position before eliminating the surface tension effect).

After carrying out the procedure of the above-described step S303, the controller 79 controls the magnetic guidance device 3 to perform the magnetic guidance of the capsule medical device 2 according to the operation of the above-described operation input unit 55 (step S304), and returns to the step S202 shown in above-described FIG. 26, thereafter. At the step S304, the controller 79 controls the magnetic guidance device 3 to perform the magnetic guidance of the capsule medical device 2 in the magnetic guidance direction and at the magnetic guidance speed specified by the operation information from the above-described operation input unit 55. In this case, the capsule medical device 2 under the liquid surface performs at least one of the swaying motion, the turning motion, the forward and backward motion in the imaging direction of the operation target image, and the right and left motion and the upward and downward motion based on the imaging direction of the image target image, as in the case of the above-described fifth embodiment.

Here, the conventional system for guiding capsule medical device applies the guidance magnetic field having the magnetization direction downward under the liquid surface to the permanent magnet 26 in the capsule medical device 2 in the floating state, when magnetically guiding the capsule medical device 2 in the state floating on the liquid surface under the liquid surface. In this case, the conventional system for guiding capsule medical device is required to generate the guidance magnetic field having the magnetic field strength stronger than that at the time of the magnetic guidance of the capsule medical device 2 under the liquid surface, in order to resist the surface tension of the liquid surface acting on the capsule medical device 2 in the floating state. That is to say, the conventional system for guiding capsule medical device sinks the capsule medical device 2 in the floating state under the liquid surface and simultaneously magnetically guides the capsule medical device 2 in the lower side of the liquid surface by the effect of the guidance magnetic field having such a high magnetic field strength. Therefore, it is difficult to control the capsule medical device 2 in the vicinity and under the liquid surface with the conventional system for guiding capsule medical device, and the capsule medical device 2 might be magnetically guided at the location or in the direction in the liquid 101, which are not intended.

On the other hand, the system for guiding capsule medical device 71 according to the sixth embodiment of the present invention eliminates in advance the effect of the surface tension of the liquid surface on the capsule medical device 2 by applying the elimination magnetic field to the capsule medical device 2 in the floating state as described above, when magnetically guiding the capsule medical device 2 in the state floating on the liquid surface of the liquid 101 under the liquid surface. Next, the system for guiding capsule medical device 71 stops the capsule medical device 2 in the state released from the effect of the surface tension in the vicinity and under the liquid surface by the magnetic force, and returns the position of the capsule medical device 2 under the liquid surface to the original state. Thereafter, the system for guiding capsule medical device 71 carries out the magnetic guidance of the capsule medical device 2 by applying the above-described guidance magnetic field to the capsule medical device 2 in such a state. The system for guiding capsule medical device 71 can carry out the magnetic guidance of the capsule medical device 2 after eliminating the effect of surface tension of the liquid surface from the capsule medical device 2, and consequently, the system for guiding capsule medical device 71 may easily control the capsule medical device 2 in the vicinity and under the liquid surface, and can easily magnetically guide the capsule medical device 2 in the desired location and direction in the liquid 101.

As described above, in the system for guiding capsule medical device according to the sixth embodiment of the present invention, it is configured to apply the elimination magnetic field to eliminate the effect of surface tension on the liquid surface to the capsule medical device in the state floating on the liquid surface to release the capsule medical device from the effect of surface tension on the liquid surface, and to apply the guidance magnetic field to the capsule medical device in the state released from the surface tension to magnetically guide the capsule medical device thereafter, and other configurations are made the same as those of the fifth embodiment. Therefore, the system for guiding capsule medical device capable of enjoying the effect similar to that of the above-described fifth embodiment, and of smoothly magnetically guiding the capsule medical device in the state floating on the liquid surface under the liquid surface without applying the guidance magnetic field having unnecessarily high magnetic field strength to the capsule medical device can be realized.

Next, a seventh embodiment of the present invention is described. Although the magnetic guidance of the capsule medical device 2 is controlled by combining the magnetic field generation control of the magnetic field generator 5 for magnetically capturing the capsule medical device 2 in the subject 100 and the motion control of the table portion of the bed 4 for supporting the subject 100 in the above-described first to sixth embodiments, the capsule medical device is magnetically guided by the guidance magnetic field generated by combining the magnetic fields in the x-axis, y-axis, and z-axis directions of the absolute coordinate system in the seventh embodiment.

Figure 35:
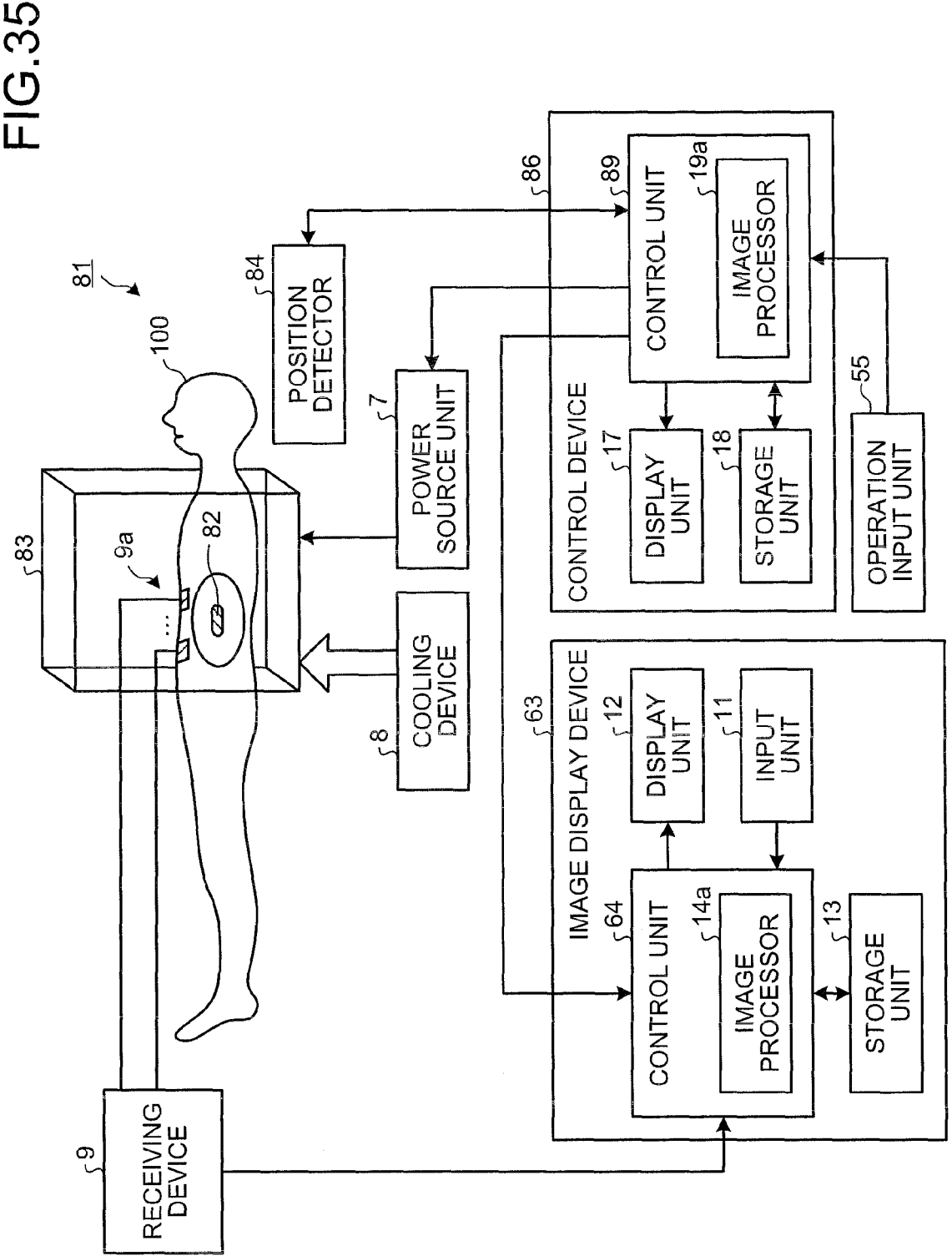
FIG. 35 is a block diagram schematically showing one configuration example of the system for guiding capsule medical device according to a seventh embodiment of the present invention.

FIG. 35 is a block diagram schematically showing one configuration example of the system for guiding capsule medical device according to the seventh embodiment of the present invention. As shown in FIG. 35, a system for guiding capsule medical device 81 according to the seventh embodiment is provided with a capsule medical device 82 in place of the capsule medical device 2 of the system for guiding capsule medical device 71 according to the above-described sixth embodiment, a magnetic guidance device 83 in place of the magnetic guidance device 3, and a control device 86 in place of the control device 76. Also, the capsule medical device 81 is provided with a location detector 84 for detecting a location of the capsule medical device 82 in the subject 100. In this seventh embodiment, the control device 86 is provided with a controller 89 in place of the controller 79 of the control device 76 according to the above-described sixth embodiment. Other configurations are the same as those of the sixth embodiment, and the same reference numerals are given to the same components.

Figure 36:
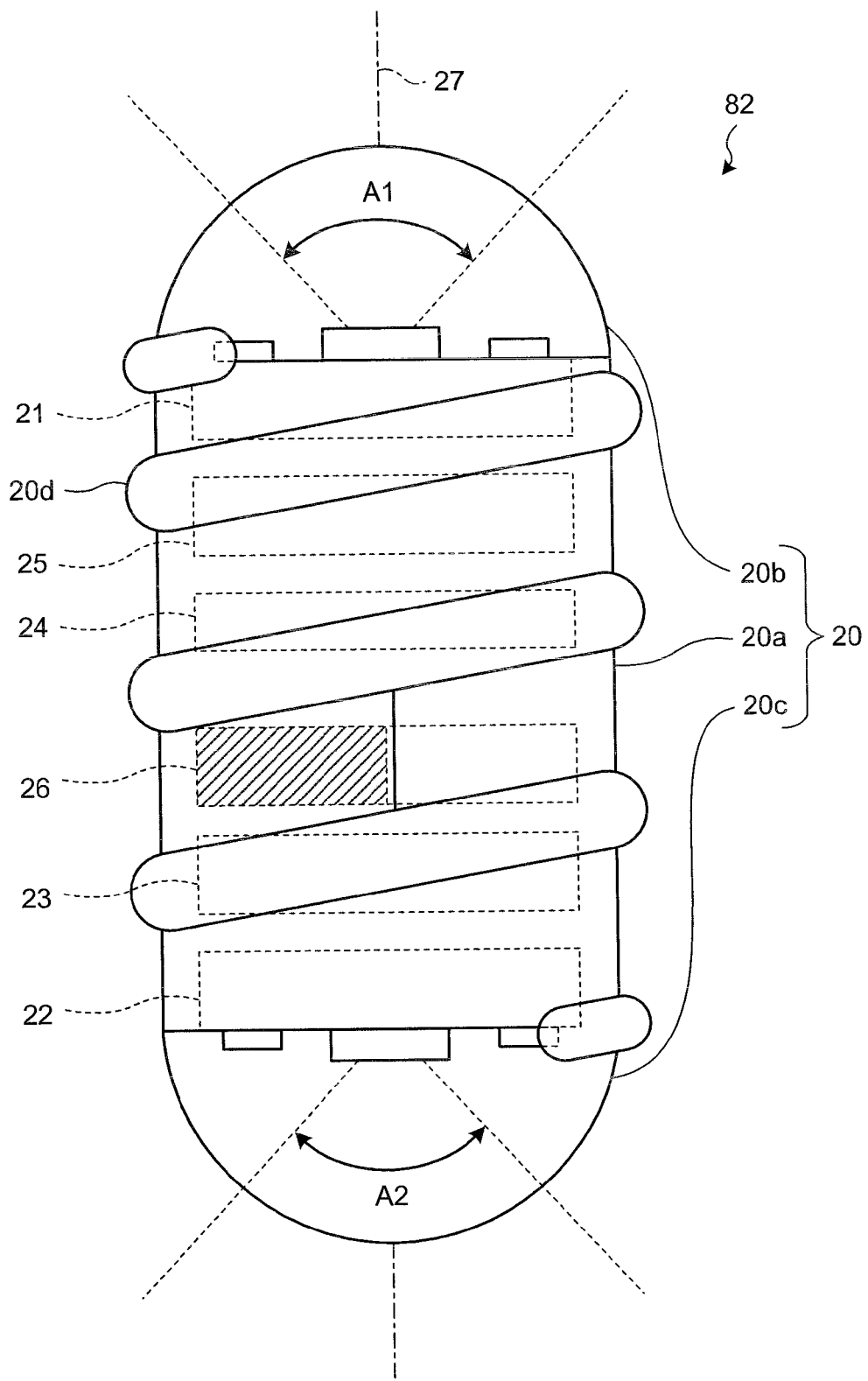
FIG. 36 is a schematic diagram showing one configuration diagram of the capsule medical device according to the seventh embodiment of the present invention.

The capsule medical device 82 is the capsule-type medical device incorporating the function of imaging the in-vivo image of the subject 100 and the radio communication function, and can be magnetically guided by the magnetic guidance device 83. FIG. 36 is a schematic diagram showing one configuration example of the capsule medical device according to the seventh embodiment of the present invention. As shown in FIG. 36, the capsule medical device 82 according to the seventh embodiment is provided with a spiral structure 20d having a spiral shape on an outer wall of the capsule casing 20. Also, the permanent magnet 26 is incorporated in the capsule medical device 82 in a mode in which the central axis thereof is arranged on the long axis 27 of the capsule casing 20. Meanwhile, the central axis of the permanent magnet 26 is one of axes of rotation at the time of rotation following the guidance magnetic field by the magnetic guidance device 83. Other configurations of the capsule medical device 82 are the same as those of the capsule medical device 2 in the above-described first to sixth embodiments, and the same reference numerals are given to the same components.

The spiral structure 20d is the structure for generating driving force in the direction of the long axis 27 of the capsule medical device 82. Specifically, the spiral structure 20d is fixed to the outer wall of the capsule casing 20 in a mode to form the spiral shape around the long axis 27 of the capsule casing 20 as shown in FIG. 36. The spiral structure 20d is in a state protruding from the outer wall of the capsule casing 20 along the spiral shape, and the spiral structure 20d contacts the digestive tract such as intestines in the subject 100, and rotates around the long axis 27 to contact the wall of the digestive tract by screwing. As a result, the spiral structure 20d generates the driving force in the direction of the long axis 27 of the capsule medical device 82. The capsule medical device 82 moves forward and backward in the direction of the long axis 27 by the driving force generated by the spiral structure 20d.

The magnetic guidance device 83 is for magnetically guiding the capsule medical device 82 in the subject 100. Specifically, the magnetic guidance device 83 is realized by using combination of a plurality of magnetic field generation coils such as Helmholtz coils. The magnetic guidance device 83 generates the magnetic field having the magnetic field strength based on the current amount from the power unit 7 in the axial directions (x-axis direction, y-axis direction, and z-axis direction) of the above-described absolute coordinate system, and combines the magnetic fields in the axial directions to generate the guidance magnetic field. Meanwhile, the guidance magnetic field by the magnetic guidance device 83 is a three-dimensional homogenous magnetic field, rotating magnetic field, or gradient magnetic field in the absolute coordinate system. The magnetic guidance device 83 applies the guidance magnetic field to the capsule medical device 82 in the subject 100, which is a three-dimensional space of the absolute coordinate system, thereby, the magnetic guidance device 83 magnetically guides the capsule medical device 82 in the subject 100, and as a result, the three-dimensional location and position of the capsule medical device 82 in the subject 100 are controlled.

The location detector 84 detects the location of the capsule medical device 82 in the subject 100. Specifically, the location detector 84 is realized by using a magnetic detection coil or the like. The location detector 84 detects the magnetic field generated by the permanent magnet 26 in the capsule medical device 82 based on the control of the control device 86. The location detector 84 detects a three-dimensional location of the capsule medical device 82 in the absolute coordinate system, that is to say, the location of the capsule medical device 82 in the subject 100 based on the detection result (such as the magnetic field strength) of the magnetic field. The location detector 84 transmits the location detection result of the capsule medical device 82 to the controller 89 of the control device 86.

Meanwhile, the location detector 84 is not limited to that performing the location detection process based on such a magnetic field detection result, and the location detector 84 may be provided with a plurality of receiving antennas for receiving the radio signal from the capsule medical device 82 to detect the location of the capsule medical device 82 in the subject 100 based on received electric-field strength of the receiving antennas.

The control device 86 is provided with a controller 89 as described above to control the above-described magnetic guidance device 83 and location detector 84. Meanwhile, the control device 86 has the function similar to that of the control device 76 in the above-described sixth embodiment, except for the control functions of the magnetic guidance device 83 and location detector 84.

The controller 89 controls the current amount of the power unit 7 to each magnetic field generation coil of the magnetic guidance device 83 based on the operation information input by the operation input unit 55, and controls the guidance magnetic field generation operation of the magnetic guidance device 83 through the control of the power unit 7. In this case, the controller 89 obtains the location detection result of the capsule medical device 82 in the subject 100 from the location detector 84 by controlling the above-described location detector 84. The controller 89 controls the magnetic guidance device 83 to apply the guidance magnetic field according to the operation information from the operation input unit 55 to a coordinate location of the absolute coordinate system indicated in the obtained location detection result, that is to say, the current location of the capsule medical device 82 in the subject 100. Also, the controller 89 controls the display unit 17 to display the location information of the capsule medical device 82 in the subject 100 based on the location detection result of the capsule medical device 82 obtained from the location detector 84. Meanwhile, the controller 89 has the function similar to that of the controller 79 of the control device 76 in the above-described sixth embodiment, except for the control functions of the magnetic guidance device 83 and location detector 84.

Figure 37:
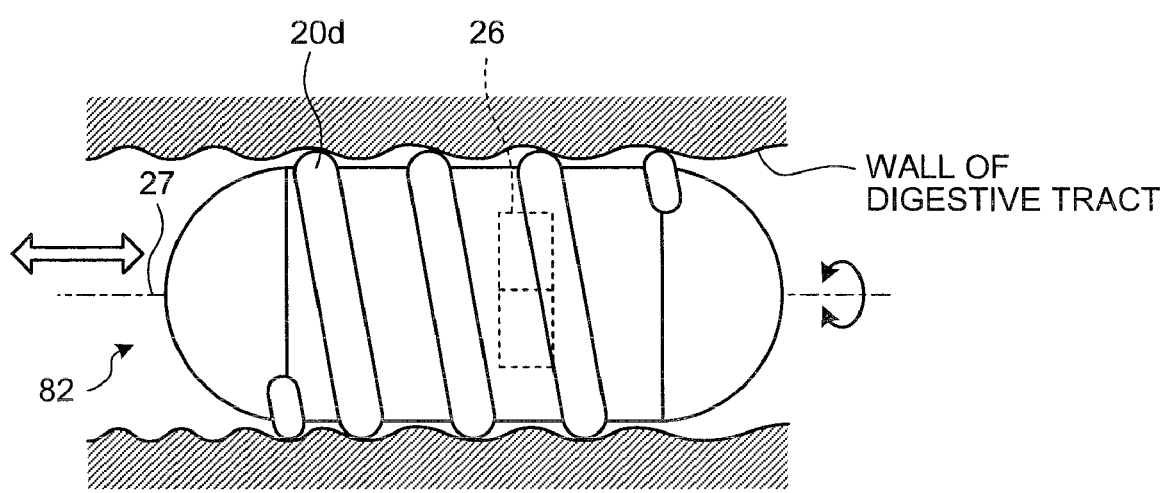
FIG. 37 is a schematic diagram showing a state in which the capsule medical device according to the seventh embodiment of the present invention is magnetically guided in a long axis direction.

Next, the magnetic guidance of the capsule medical device 82 according to the seventh embodiment in the direction of the long axis 27 is described. FIG. 37 is a schematic diagram showing a state in which the capsule medical device according to the seventh embodiment of the present invention is magnetically guided in the long axis direction.

When the capsule medical device 82 reaches in the digestive tract such as the intestines of the subject 100, this is in the state in which the wall of the digestive tract and the spiral structure 20d contact each other by screwing as shown in FIG. 37. Here, the magnetic guidance device 83 generates the guidance magnetic field rotating around the long axis 27 of the capsule medical device 82, and applies the guidance magnetic field around the long axis 27 to the permanent magnet 26 in the capsule medical device 82 based on the control of the controller 89. In this case, the permanent magnet 26 rotates around the long axis 27 with the spiral structure 20d following such a guidance magnetic field. The spiral structure 20d rotates around the long axis 27 while contacting the wall of the digestive tract by screwing, thereby generating the driving force in the direction of the long axis 27. The capsule medical device 82 moves forward and backward in the direction of the long axis 27 by the effect of the spiral structure 20d. The magnetic guidance device 83 magnetically guides the capsule medical device 82 in the direction of the long axis 27 while allowing the capsule medical device 82 to move forward and backward by the effect of the guidance magnetic field in this manner.

As described above, in the system for guiding capsule medical device according to the seventh embodiment of the present invention, it is configured that the capsule medical device provided with the spiral structure around the long axis of the capsule casing is introduced into the organ of the subject, and the guidance magnetic field generated by combining the magnetic fields in the axial directions of the absolute coordinate system is applied to the capsule medical device in the subject to magnetically guide the capsule medical device, and other configurations are made the same as those of the sixth embodiment. Therefore, the system for guiding capsule medical device capable of enjoying the effect similar to that of the above-described sixth embodiment, and of easily magnetically guiding the capsule medical device along the digestive tract by rotating the spiral structure in the state of contacting the wall of the digestive tract along the long axis of the capsule casing.

Next, an eighth embodiment of the present invention is described. Although the magnetic guidance of the capsule medical device 2 is controlled by combining magnetic field generation control of the magnetic field generator 5 for magnetically capturing the capsule medical device 2 in the subject 100 and motion control of the table portion of the bed 4 for supporting the subject 100 in the above-described first to sixth embodiments, the capsule medical device is magnetically guided by the gradient magnetic field generated as the guidance magnetic field in the eighth embodiment.

Figure 38:
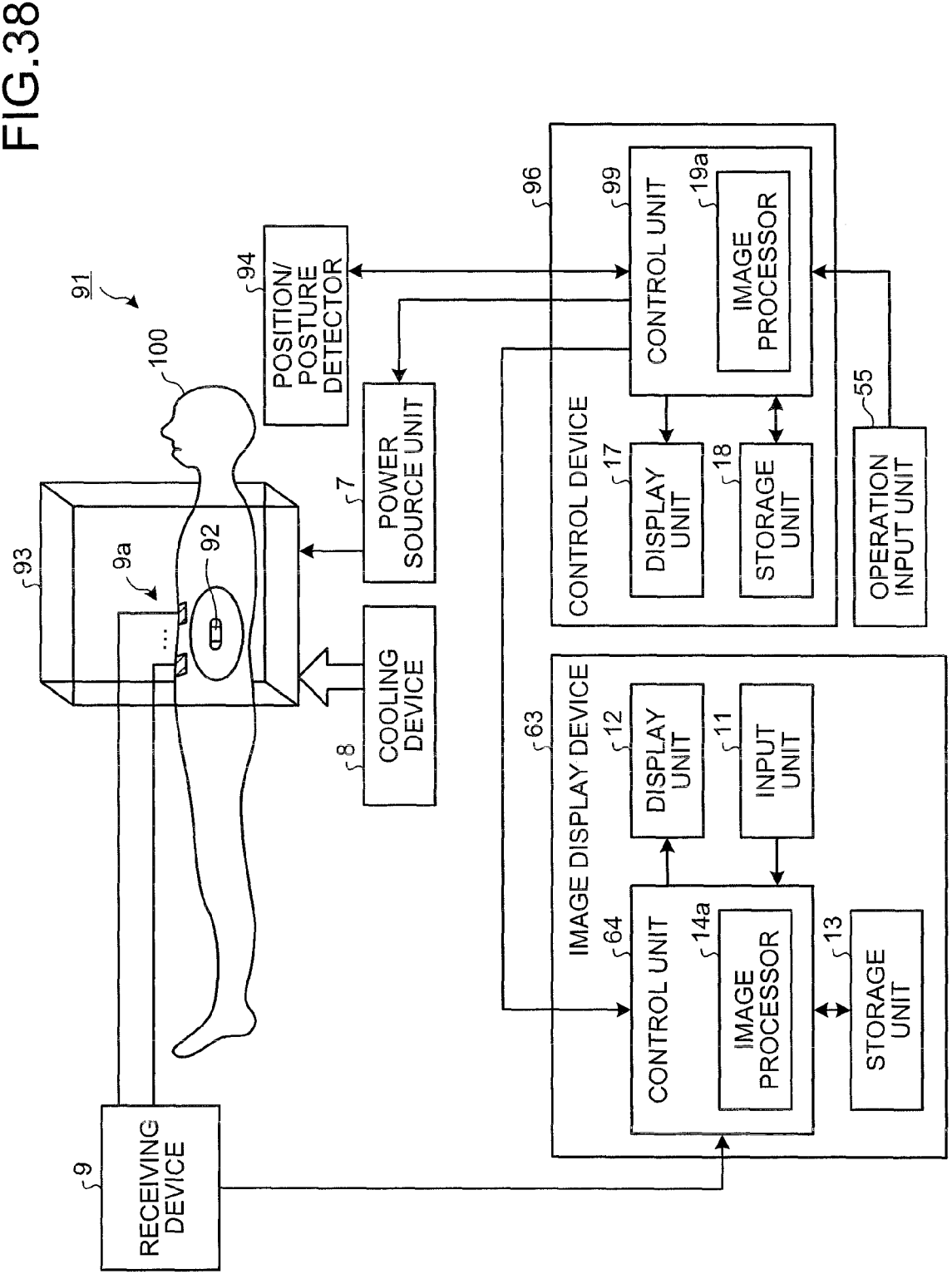
FIG. 38 is a block diagram schematically showing one configuration example of the system for guiding capsule medical device according to an eighth embodiment of the present invention.

FIG. 38 is a block diagram schematically showing one configuration example of the system for guiding capsule medical device according to the eighth embodiment of the present invention. As shown in FIG. 38, a system for guiding capsule medical device 91 according to the eighth embodiment is provided with a capsule medical device 92 in place of the capsule medical device 2 of the system for guiding capsule medical device 71 according to the above-described sixth embodiment, a magnetic guidance device 93 in place of the magnetic guidance device 3, and a control device 96 in place of the control device 76. Also, the system for guiding capsule medical device 91 is provided with a location position detector 94 for detecting the location and the position of the capsule medical device 92 in the subject 100. In the eighth embodiment, the control device 96 is provided with a controller 99 in place of the controller 79 of the control device 76 according to the above-described sixth embodiment. Other configurations are the same as those of the sixth embodiment, and the same reference numerals are given to the same components.

Figure 39:
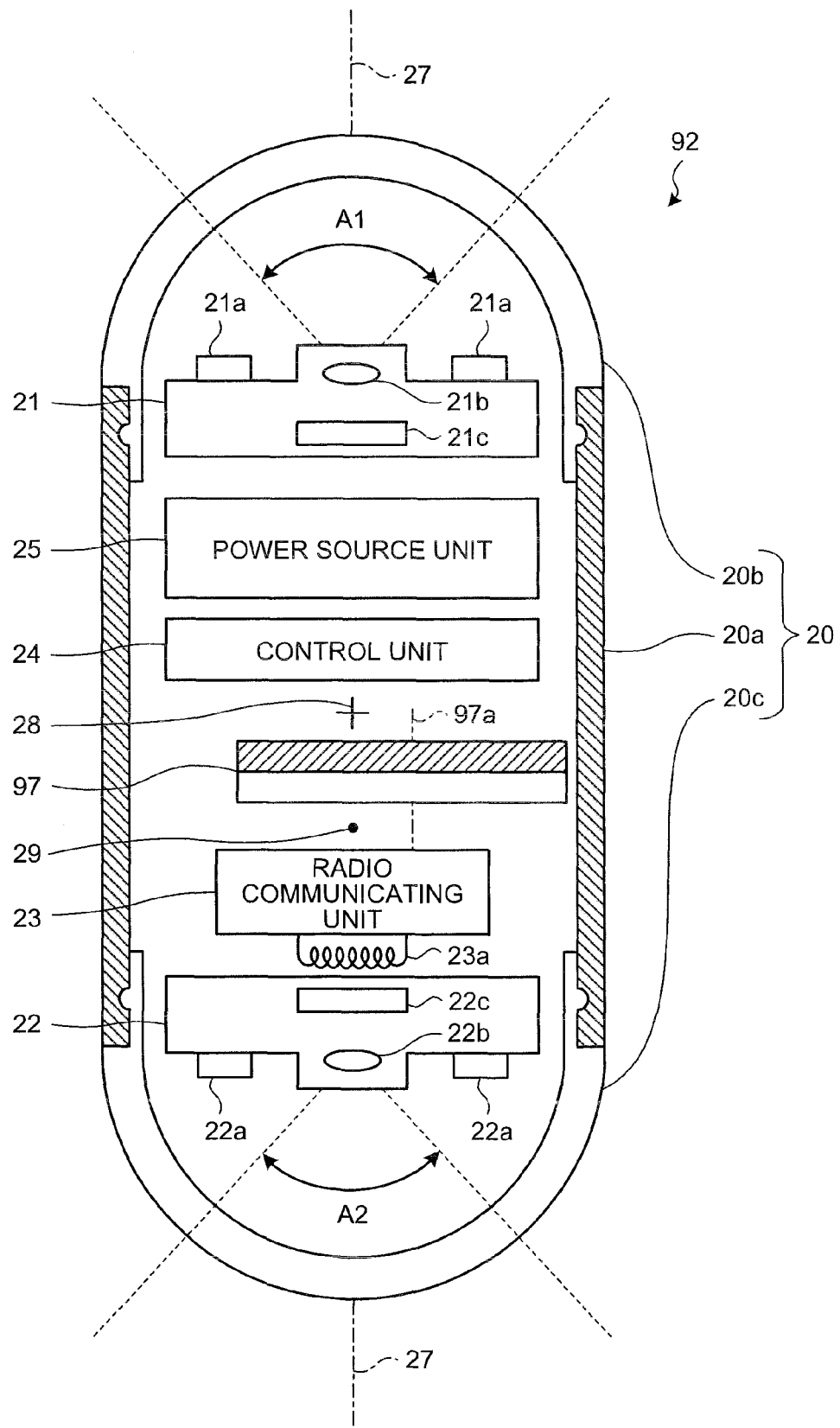
FIG. 39 is a schematic diagram showing one configuration example of the capsule medical device according to the eighth embodiment of the present invention.

The capsule medical device 92 is the capsule-type medical device incorporating the function of imaging the in-vivo image of the subject 100 and the radio communication function, and can be magnetically guided by the magnetic guidance device 93. FIG. 39 is a schematic diagram showing one configuration example of the capsule medical device according to the eighth embodiment of the present invention. As shown in FIG. 39, the capsule medical device 92 according to the eighth embodiment is provided with a permanent magnet 97 magnetized in the direction of the long axis 27 of the capsule casing 20 in place of the permanent magnet 26 magnetized in the radial direction as described above. Meanwhile, other configurations in the capsule medical device 92 are the same as the capsule medical device 2 in the above-described first to sixth embodiments, and the same reference numerals are given to the same components.

The permanent magnet 97 is for enabling the magnetic guidance of the capsule medical device 92 by the magnetic guidance device 93. The permanent magnet 97 is arranged in the capsule casing 20 in a state relatively fixed with respect to the imaging units 21 and 22. In this case, the permanent magnet 97 is magnetized in the direction of the long axis 27 of the capsule casing 20 as shown in FIG. 39. That is to say, the magnetization direction of the permanent magnet 97 is parallel to the imaging directions of the above-described imaging units 21 and 22. Also, a central axis 97*a* of the permanent magnet 97 is parallel to the long axis 27 of the capsule casing 20 and deviated from the center of gravity 29 of the capsule medical device 2. That is to say, the center of gravity 29 of the capsule medical device 92 is not located on the central axis 97*a* of the permanent magnet 97.

The guidance magnetic field is applied from the outside of the capsule medical device 92 to the permanent magnet 27 thus arranged by the magnetic guidance device 93. The permanent magnet 97 moves following such a guidance magnetic field, and consequently realizes the magnetic guidance of the capsule medical device 92 by the magnetic guidance device 93. In this case, the capsule medical device 92 moves to change at least one of the location, the position, and the direction in the subject 100 by the effect of the permanent magnet 97. Alternatively, the capsule medical device 92 maintains the state of being stopped at the desired location in the subject 100 by the effect of the permanent magnet 97.

The magnetic guidance device 93 is for magnetically guiding the capsule medical device 92 in the subject 100. Specifically, the magnetic guidance device 93 is realized by combining a plurality of magnetic field generation coils. The magnetic guidance device 93 generates the gradient magnetic field in which magnetic flux density changes in a desired direction in the above-described absolute coordinate system based on the power supplied from the power unit 7, and applies the gradient magnetic field to the capsule medical device 92 in the subject 100 as the guidance magnetic field. Thereby, the magnetic guidance device 93 magnetically guides the capsule medical device 92 in the subject 100, which is the three-dimensional space of the absolute coordinate system. More specifically, the magnetic guidance device 93 controls the position of the capsule medical device 92 in the subject 100 (that is to say, the three-dimensional direction of the long axis 27 of the capsule medical device 92) by the magnetic field direction of the applied gradient magnetic field. Also, the magnetic guidance device 93 controls the location of the capsule medical device 92 in the subject 100 by magnetic attraction force of the applied gradient magnetic field.

The location position detector 94 detects the location and the position of the capsule medical device 92 in the subject 100. Specifically, the location position detector 94 is realized by using the magnetic field detection coil or the like. The location position detector 94 detects the magnetic field strength and the magnetic field direction of the magnetic field generated from the permanent magnet 27 in the capsule medical device 92 based on the control of the control device 96. The location position detector 94 detects the three-dimensional location of the capsule medical device 92 in the absolute coordinate system, that is to say, the location of the capsule medical device 92 in the subject 100, based on the detected magnetic field strength. Also, the location position detector 94 detects the direction of the long axis 27 and the radial direction of the capsule medical device 92 in the absolute coordinate system based on the detected magnetic field direction to detect the position of the capsule medical device 92 defined by the direction of the long axis 27 and the radial direction. The location position detector 94 transmits the detection results of the location and the position of the capsule medical device 92 to the controller 99 of the control device 96.

Meanwhile, the location position detector 94 is not limited to that performing the location detection process based on such a magnetic field detection result, and the location position detector 94 may be provided with a plurality of receiving antennas receiving the radio signal from the capsule medical device 92 to detect the location of the capsule medical device 92 in the subject 100 based on the received electric-field strength of the receiving antennas.

The control device 96 is provided with the controller 99 as described above to control the above-described magnetic guidance device 93 and location position detector 94. Meanwhile, the control device 96 has the function similar to that of the control device 76 in the above-described sixth embodiment, except for the control functions of the magnetic guidance device 9 and location position detector 94.

The controller 99 controls the current amount of the power unit 7 to the magnetic field generation coil of the magnetic guidance device based on the operation information input by the operation input unit 55, and controls the guidance magnetic field generation operation of the magnetic guidance device 93 through the control of the power unit 7. In this case, the controller 99 determines the gradient direction and the magnetic field direction of the guidance magnetic field in the absolute coordinate system based on the magnetic guidance direction specified by the operation information from the operation input unit 55. Also, the controller 99 determines gradient change of the guidance magnetic field in the absolute coordinate system (that is to say, the magnetic attraction force by the guidance magnetic field) based on the magnetic guidance speed specified by the operation information. The controller 99 controls the magnetic guidance device 93 to apply the guidance magnetic field having the gradient direction, the magnetic field direction and the gradient change thus determined to the capsule medical device 92 in the subject 100. The controller 99 controls the position of the capsule medical device 92 in the subject 100 through the control of the magnetic field direction of such a guidance magnetic field, and controls the location of the capsule medical device 92 in the subject 100 through the control of the gradient direction and the gradient change of such a guidance magnetic field.

Also, the controller 99 controls the above-described location position detector 94 to obtain the detection results of the location and the position of the capsule medical device 92 in the subject 100 from the location position detector 94. The controller 99 controls the display unit 17 to display the location information of the capsule medical device 92 in the subject 100 based on the location detection result of the capsule medical device 92 obtained from the location position detector 94. Also, the controller 99 calculates the elevation angle and the direction angle of the capsule medical device 92 in the subject 100 based on the position detection result of the capsule medical device 92 obtained from the location position detector 94. The controller 99 controls the display unit 17 to display the elevation angle information and the direction angle information of the capsule medical device 92 thus calculated. Meanwhile, other function of the controller 99 is the same as that of the controller 79 of the control device 76 in the above-described sixth embodiment.

Meanwhile, in the eighth embodiment, the controller 64 of the image display device 63 obtains the position detection result of the capsule medical device 92 by the location position detector 94 from the controller 99 of the above-described control device 96. The controller 64 allows the display unit 12 to display the in-vivo image by conforming the direction of intersection line of the above-described in-vivo image and the up and own direction of the display screen based on the obtained position detection result. In this case, the image processor 14a calculates the upward and downward directions D2 and D3 of the imaging surfaces of the solid-state imaging devices 21c and 22c, respectively, of the capsule medical device 92, based on the position detection result of the capsule medical device 92 obtained from the controller 99 of the control device 92. The image processor 14a rotates the in-vivo image as necessary based on the relative relation between the radial direction of the capsule casing 10, which is known, and the upward and downward directions D2 and D3 of the imaging surfaces of the solid-state imaging devices 21c and 22c, respectively, thereby conforming the direction of intersection line in the in-vivo images P1 and P2 by the solid-state imaging devices 21 and 22c, respectively, and the upward and downward direction of the display screen of the display unit 12.

As described above, in the system for guiding capsule medical device according to the eighth embodiment of the present invention, it is configured that the capsule medical device provided with the permanent magnet magnetized in the direction of long axis of the capsule casing is introduced into the organ of the subject, and the gradient magnetic field inclined in a desired direction of the absolute coordinate system is applied to the capsule medical device in the subject to magnetically guide the capsule medical device, and other configurations are made the same as those of the sixth embodiment. Therefore, the system for guiding capsule medical device capable of enjoying the effect similar to that of the above-described sixth embodiment, and of magnetically guiding the capsule medical device by the magnetic attraction force in the gradient direction of the gradient magnetic field, and consequently, capable of magnetically guiding the capsule medical device in the desired direction in the subject with the simple configuration can be realized.

Figure 40:
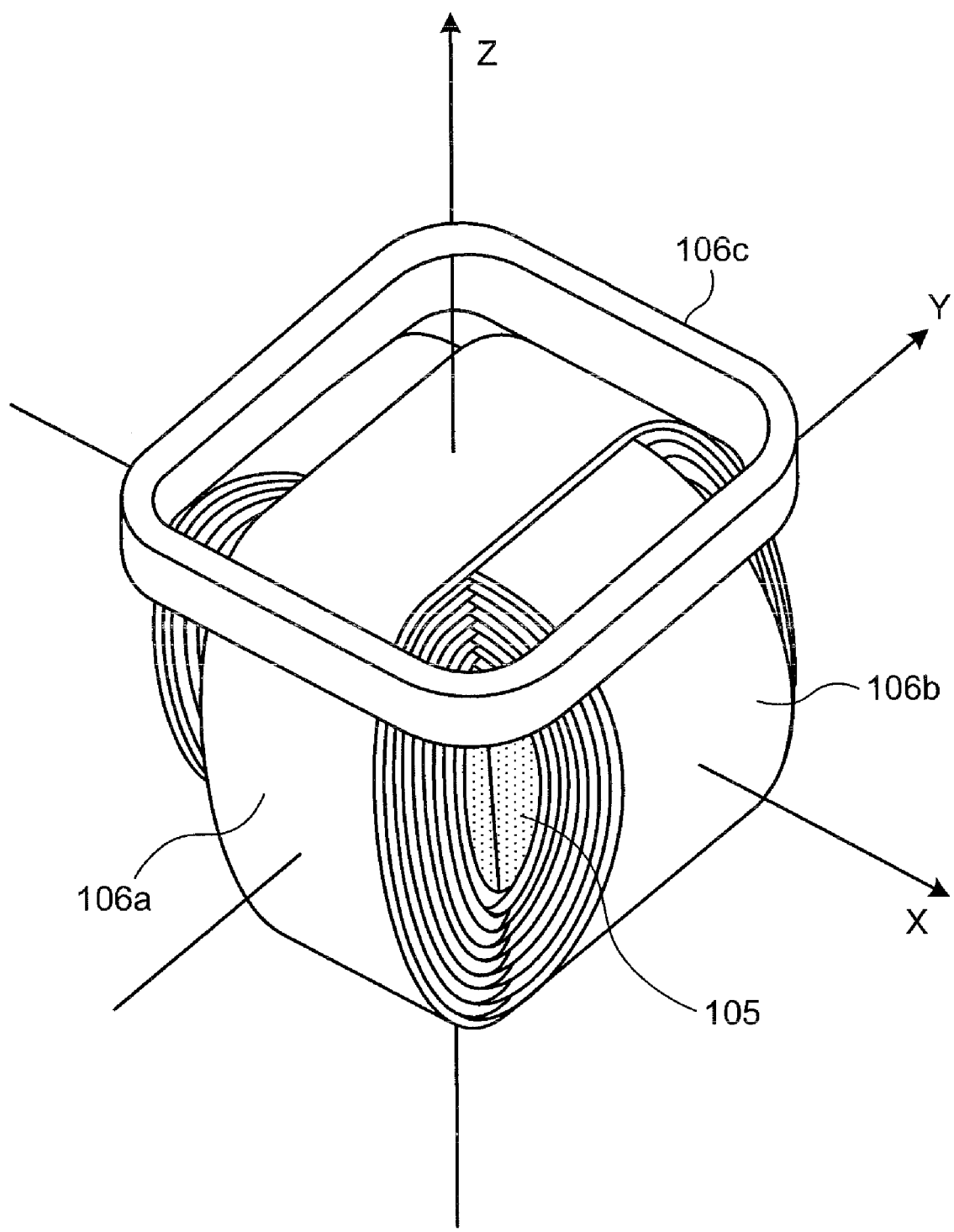
FIG. 40 is a schematic diagram showing one modification of a magnetic field generator of the system for guiding capsule medical device according to the present invention.

Meanwhile, although the guidance magnetic field is generated by the magnetic field generator 5 provided with the above-described z-axis coil 5a, a pair of x-axis coils 5b and 5c, and a pair of y-axis coils 5d and 5e on the table 5f in the above-described first to sixth embodiments, the present invention is not limited to this, and the guidance magnetic field may be generated by the magnetic field generator realized by three-dimensionally combining the three axial direction coils generating the magnetic fields in the axial directions of the absolute coordinate system. FIG. 40 is a schematic diagram showing one modification of the magnetic field generator of the system for guiding capsule medical device according to the present invention. As shown in FIG. 40, the magnetic field generator in the present invention is realized by three-dimensionally combining an x-axis coil 106a for generating the magnetic field in the x-axis direction of the absolute coordinate system, a y-axis coil 106b for generating the magnetic field in the y-axis direction of the absolute coordinate system, and a z-axis coil 106c for generating the magnetic field in the z-axis direction of the absolute coordinate system. The x-axis coil 106a and the y-axis coil 106b roll up a metal core 105 such as iron in a mode orthogonal to each other. The z-axis coil 106c is arranged on an upper portion of the x-axis coil 106a and y-axis coil 106b.

Figure 41:
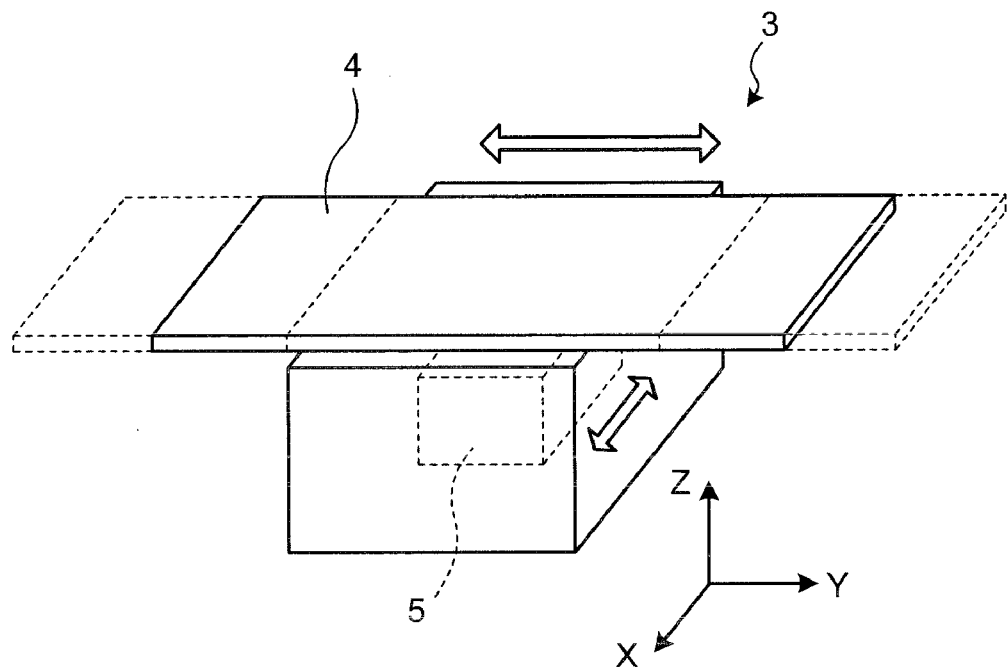
FIG. 41 is a schematic diagram showing one example of each moving state of a table portion of a bed and the magnetic field generator.

Also, a relative location of the table portion of the bed 4 with respect to the magnetic field generator 5, that is to say, the relative location of the subject 100 with respect to the magnetic field generator 5 is changed by horizontally moving the table portion of the bed 4 supporting the subject 100 in at least one of the x-axis direction and the y-axis direction of the absolute coordinate system in the above-described first to sixth embodiments, the present invention is not limited to this. FIG. 41 is a schematic diagram showing one example of the motion states of the table portion of the bed and the magnetic field generator. As shown in FIG. 41, the magnetic guidance device 3 may horizontally move the table portion of the bed 4 in the y-axis direction of the absolute coordinate system, and may horizontally move the magnetic field generator 5 in the x-axis direction of the absolute coordinate system. Alternatively, the magnetic guidance device 3 may horizontally move the table portion of the bed 4 in the x-axis direction of the absolute coordinate system, and may horizontally move the magnetic field generator 5 in the y-axis direction of the absolute coordinate system. In any case, the magnetic guidance device 3 may appropriately combine the horizontal motion of the table portion of the bed 4 and the horizontal motion of the magnetic field generator 5, thereby changing the relative location of the subject 100 with respect to the magnetic field generator 5.

Figure 42:
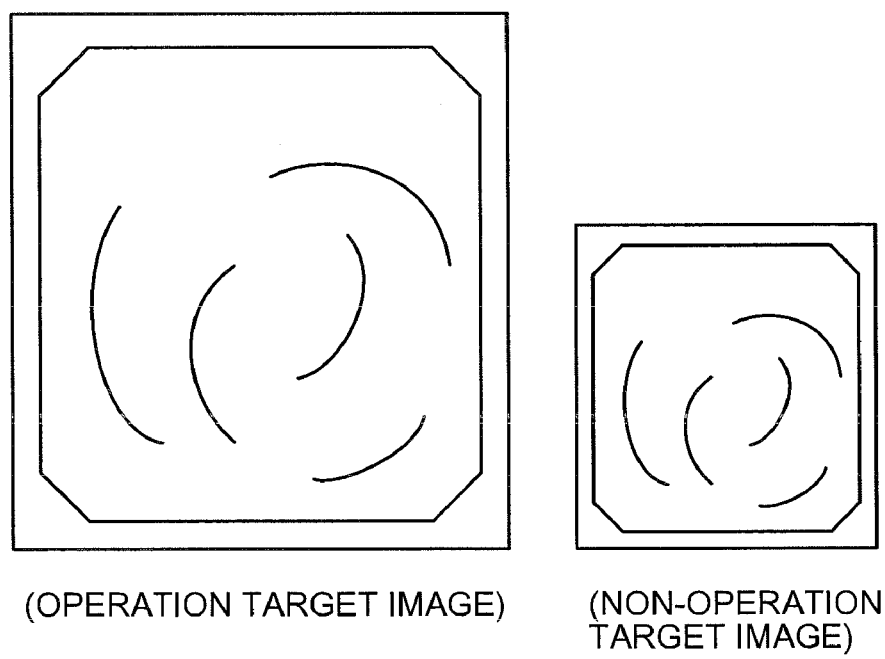
FIG. 42 is a schematic diagram showing a modification of a state clearly showing the operation target image in the image display device according to the present invention.

Further, although the operation target image is clearly shown by displaying the frame image 32a around the main-image display area displaying the operation target image in the above-described second, fourth to eighth embodiments, the present invention is not limited to this. FIG. 42 is a schematic diagram showing a modification of the state clearly showing the operation target image in the image display device according to the present invention. The image display device according to the present invention may enlarge a display size of the operation target image relative to a non-operation target image out of a plurality of the in-vivo images, as shown in FIG. 42, for example, thereby clearly showing the operation target image. Alternatively, the image display device according to the present invention may add the predetermined mark to the operation target image out of a plurality of the in-vivo images, thereby clearly showing the operation target image.

Figure 43:
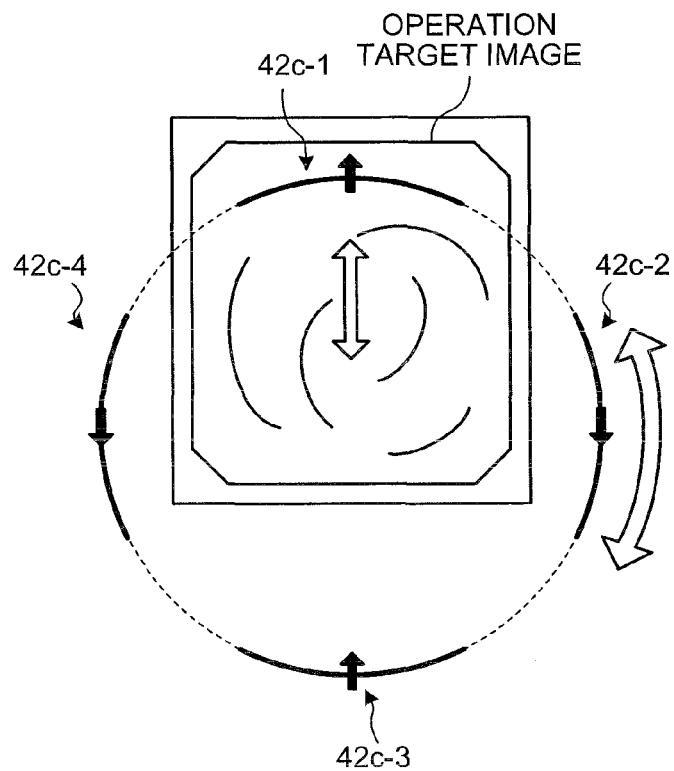
FIG. 43 is a schematic diagram showing a modification of a display state of the direction angle information of the capsule medical device.

Also, although the direction angle information of the capsule medical device is displayed by displaying the bar-type direction information 42c in the vicinity of the outer side of the operation target image in the above-described third to eighth embodiments, the present invention is not limited to this. FIG. 43 is a schematic diagram showing a modification of the display state of the direction angle information of the capsule medical device in the operation target image, as shown in FIG. 43, for example. The image display device according to the present invention may appropriately display pieces of circular arc-shaped direction information 42c-1 to 42c-4 each including an arrow different for each direction of the capsule medical device. In this case, the image display device according to the present invention sequentially display the pieces of direction information 42c-1, 42c-2, 42c-3, and 42c-4 in this order or in reverse in the operation target image, in response to change in direction angle (that is to say, the turning motion) of the capsule medical device. Meanwhile, the display location of the arrows in the pieces of direction information 42c-1 to 42c-4 in such an operation target image may be set in consideration of the distortion of the optical system of the capsule medical device. Also, the image display device according to the present invention may move the direction information displayed in the operation target image out of the pieces of the direction information 42c-1 to 42c-4 to the upward and downward direction of the operation target image in response to change in the elevation angle (that is to say, the swaying motion) of the capsule medical device. In this case, the image display device according to the present invention is not required to display the above-described marks 42a and 42b of the elevation angle information.

Further, the direction of the capsule medical device is indicated by the arrow included in each of the pieces of direction information 42c-1 to 42c-4 in the above-described third to eighth embodiments, the present invention is not limited to this. Specifically, when the direction of the subject is defined with respect to the display screen, character information indicating a region of the subject such as the head side, the foot side, the stomach side, and the back side is included in the pieces of direction information 42c-1 to 42c-4 in place of such an arrow. The image display device according to the present invention may display the direction angle Information of the capsule medical device by displaying the character information of any of the pieces of the direction information 42c-1 to 42c-4. In this case, the image display device according to the present information can directly display the relative direction of the capsule medical device with respect to the subject. Meanwhile, when the body posture of the subject is changed, the image display device according to the present invention may change the character information to be displayed out of each character information of pieces of the direction information 42c-1 to 42c-4 in response to the change in the body posture of such a subject.

Figure 44:
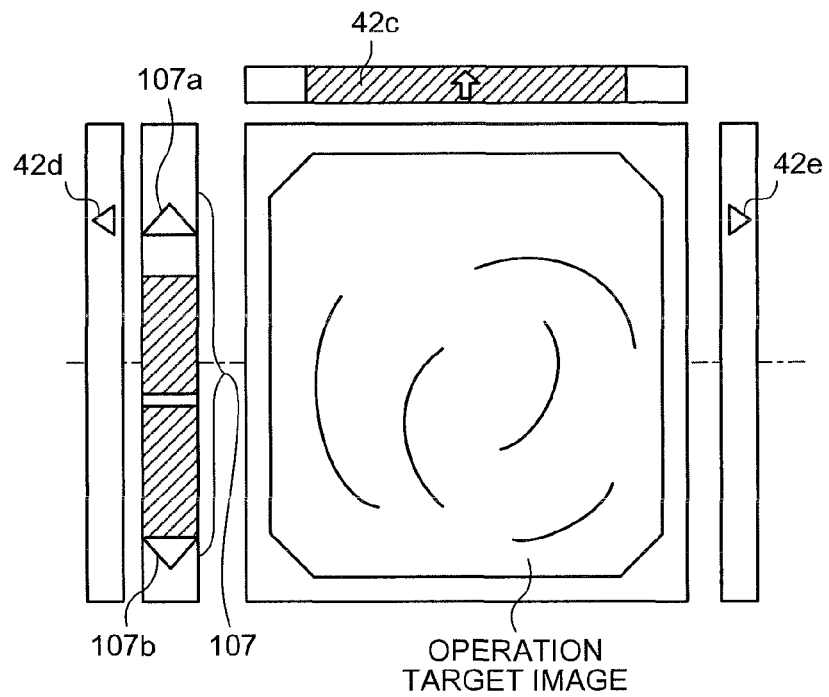
FIG. 44 is a schematic diagram showing a modification of the display state of the elevation angle information.

Also, although the marks 42a and 42b of the elevation angle information are displayed in the operation target image in the above-described third to eighth embodiments, the present invention is not limited to this. FIG. 44 is a schematic diagram showing a modification of the display state of the elevation angle information. The image display device according to the present invention displays a bar image 107 indicating the elevation angle information of the capsule medical device in the vicinity of the side portion of the operation target image as shown in FIG. 44, for example. The bar image 107 is bar-type image information including a mark 107a on an upper end and a mark 107b on a lower end, and is displayed in a state in which a central portion of the bar is clearly indicated. The image display device according to the present invention longitudinally moves the bar image 107 in the bar-type information display area in response to the change in the elevation angle of the capsule medical device. The image display device according to the present invention displays the elevation angle information of the capsule medical device by the display location of the bar image 107. Specifically, the bar image 107 moves to a lower portion of the operation target image in association with increase in the elevation angle of the capsule medical device 2. The mark 107a on the upper end side of the bar image 107 moves onto the central line of the operation target image when the elevation angle of the capsule medical device is 90 degrees. On the other hand, the bar image 107 moves to an upper portion of the operation target image in association with decrease in the elevation angle of the capsule medical device. The mark 107b on the lower end side of the bar image 107 moves onto the central line of the operation target image when the elevation angle of the capsule medical device is 0 degree.

Further, the image display device according to the present invention may display the above-described marks 42d and 42e in the bar-type information display area formed in the vicinity of the side portion of the operation target image, and may longitudinally move the marks 42d and 42e in response to change in the elevation angle of the capsule medical device, as shown in FIG. 44, for example. In this case, the image display device according to the present invention may always display the marks 42d and 42e in such an information display area with a predetermined color (white, for example) regardless of the presence of the input of the above-described operation information, and when such operation information is input, the image display device may display the mark corresponding to the operation information out of the marks 42d and 42e with another color (yellow, for example). Meanwhile, the marks 42d and 42e in such an information display area are displayed so as to be arranged widthwise with the mark 107a of the elevation angle information interposed therebetween, for example, and are longitudinally moved as the mark 107a of the elevation angle information.

Figure 45A:
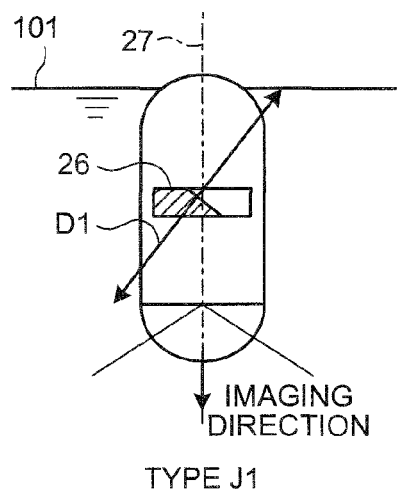
FIGS. 45A to 45D are schematic diagrams each showing a modification of the capsule medical device floatable on the liquid surface according to the present invention.
Figure 45B:
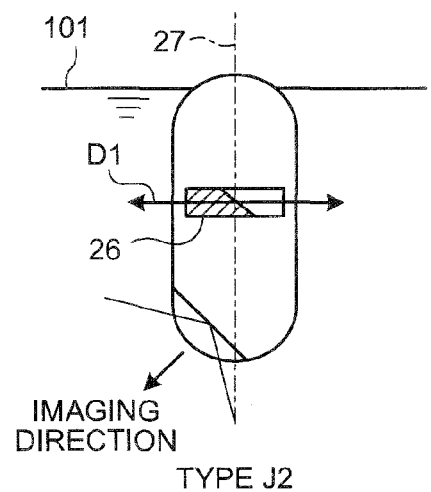
Figure 45C:
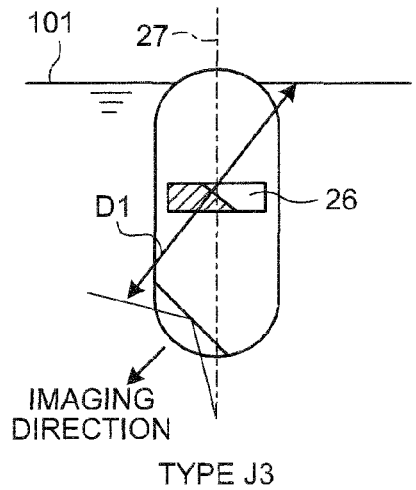
Figure 45D:
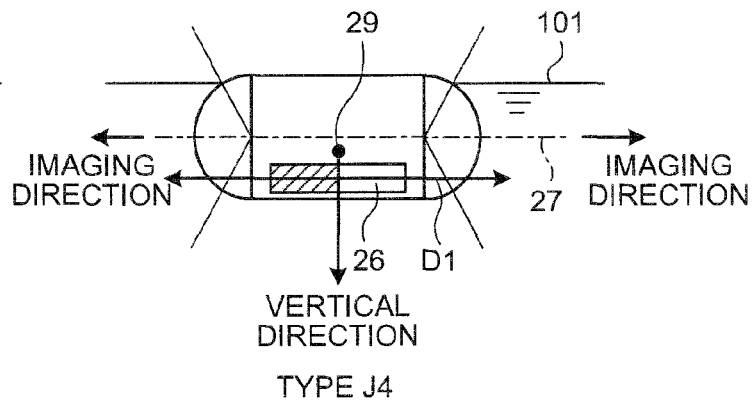

Although the imaging direction of the capsule medical device is parallel to the long axis of the capsule casing and the magnetization direction of the capsule medical device is parallel to or perpendicular to the long axis of the capsule casing in the above-described first to eighth embodiments, the present invention is not limited to this. FIGS. 45A to 45D are schematic diagrams each showing a modification of the capsule medical device floatable on the liquid surface according to the present invention. In the capsule medical device according to the present invention, the center of gravity may be set so as to maintain the above-described specific state in the liquid 101 and the capsule medical device may have the magnetization direction in a direction different from the vertical direction in the specific state. Specifically, as shown in FIG. 45A, the capsule medical device floatable on the liquid surface according to the present invention may be the capsule medical device of type J1 in which the imaging direction is parallel to the long axis 27 and the magnetization direction D1 of the permanent magnet 26 inclines with respect to the long axis 27, or may be the capsule medical device of type J2 in which the imaging direction inclines with respect to the long axis 27 and the magnetization direction D1 of the permanent magnet 26 is perpendicular to the long axis 27, as shown in FIG. 45B. Alternatively, the capsule medical device floatable on the liquid surface according to the present invention may be the capsule medical device of type J3 in which the imaging direction and the magnetization direction D1 of the permanent magnet 26 incline with respect to the long axis 27 as shown in FIG. 45C, or may be the capsule medical device of type J4 in which the imaging direction and the magnetization direction D1 of the permanent magnet 26 is parallel to the long axis 27 as shown in FIG. 45D. Meanwhile, the center of gravity 29 is set on the location deviated from the geometric center of the capsule casing in the radial direction. That is to say, the capsule medical device of type J4 floats on the liquid surface of the liquid 101 in a state in which the long axis 27 is perpendicular to the vertical direction.

Figure 46A:
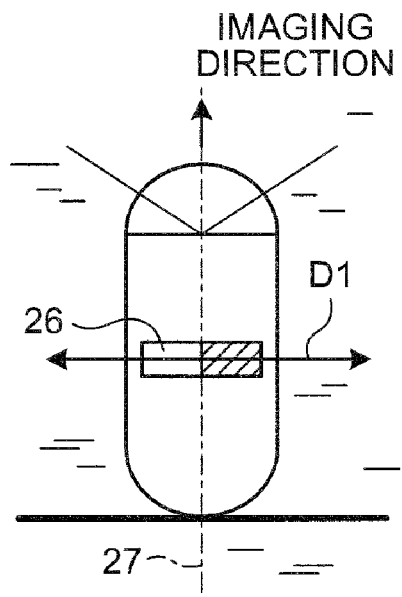
FIGS. 46A to 46D are schematic diagrams each showing a specific example of the capsule medical device sinkable under the liquid surface according to the present invention.
Figure 46B:
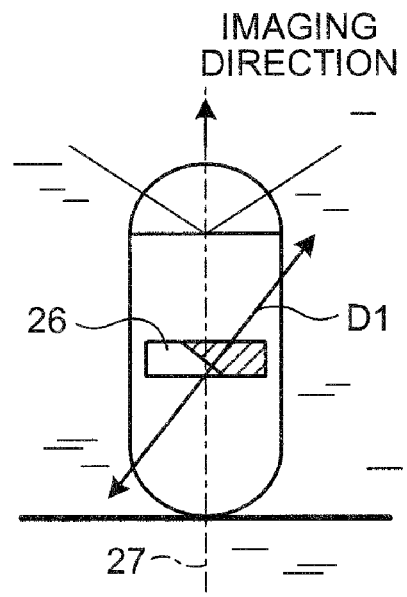
Figure 46C:
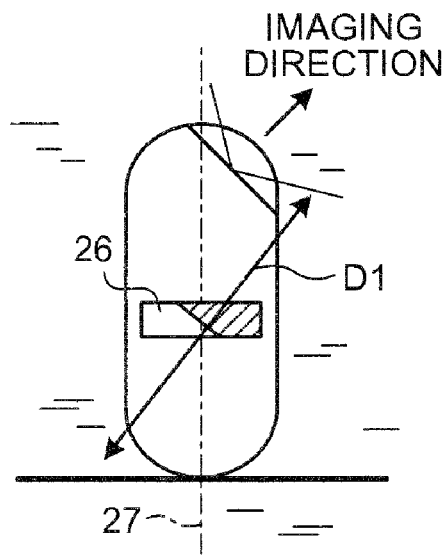
Figure 46D:
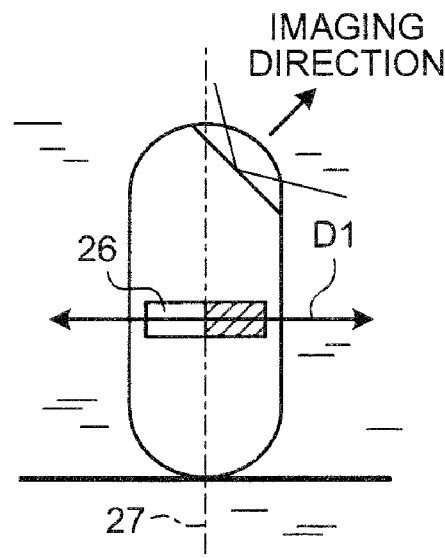

On the other hand, although the capsule medical device floatable on the liquid 101 in the subject 100 is illustrated in the above-described first to eighth embodiments, the present invention is not limited to this. FIGS. 46A to 46D are schematic diagrams each showing a specific example of the capsule medical device sinkable under the liquid surface according to the present invention. In the capsule medical device according to the present invention, the center of gravity may be set so as to maintain the above-described specific state in the liquid 101, and the capsule medical device may have the magnetization direction in the direction different from the vertical direction. Specifically, as shown in FIG. 46A, the capsule medical device sinkable under the liquid surface according to the present invention may be the capsule medical device of type J5 in which the imaging direction is parallel to the long axis 27 and the magnetization direction D1 of the permanent magnet 26 is perpendicular to the long axis 27, or may be the capsule medical device of type J6 in which the imaging direction is parallel to the long axis 27 and the magnetization direction D1 of the permanent magnet 26 inclines with respect to the long axis 27 as shown in FIG. 46B. Alternatively, the capsule medical device sinkable under the liquid surface according to the present invention may be the capsule medical device of type J7 in which the imaging direction and the magnetization direction D1 of the permanent magnet 26 incline with respect to the long axis 27 as shown in FIG. 46C, or the capsule medical device of type J8 in which the imaging direction inclines with respect to the long axis 27 and the magnetization direction D1 of the permanent magnet 26 is perpendicular to the long axis 27 as shown in FIG. 46D.

Also, although the twin-lens capsule medical device incorporating the two imaging units 21 and 22 of which imaging directions are different to each other is illustrated in the above-described first to eighth embodiments, the present invention is not limited to this, and the capsule medical device according to the present invention may be a monocular capsule medical device incorporating a unique imaging unit or may be a polynocular capsule medical device incorporating three or more imaging units.

Further, although the elevation angle information, the direction angle information, and the information indicating that the operation information is input of the capsule medical device are displayed by being related to the operation target image out of the in-vivo images P1 and P2 by the imaging units 21 and 22, respectively in the above-described third to eighth embodiments, the present invention is not limited to this, and it is possible to display the elevation angle information, the direction angle information, and the information indicating that the operation information is input of the capsule medical device, by relating them to each of a plurality of in-vivo images in the display screen while clearly showing the operation target image by the display of the above-described frame image 32a or the like. In this case, the direction angle information of the capsule medical device is displayed so as to indicate the direction of the capsule medical device different for each imaging direction of the in-vivo images. Also, the information indicating that the operation information is input is displayed by different display colors of the mark for each imaging direction of the in-vivo images. Specifically, the marks 42a, 42b and 62a displayed in the operation target image are displayed with the display color such as blue in response to the input of the operation information, and the marks 42a, 42b and 62a displayed in the non-operation target image are displayed with the color different from the mark display color (such as red) in the operation target image in response to the input of the operation information.

Also, although the desired in-vivo image data selected from a plurality of in-vivo images displayed on the display unit is saved in the storage unit in the above-described first to eighth embodiments, the present invention may further relate the body posture information of the subject set by the above-described body posture setting unit 17f to the in-vivo image data to save in the storage unit. Thereby, the user can easily judge of which side (such as the right side, the left side, the head side, the leg side, the stomach side, and the back side) in the subject the in-vivo image read from the storage unit is, and consequently, the user can easily comprehend the region of the subject now under observation.

Further, although the operation target image is switched between a plurality of in-vivo images by the input operation of the operation input unit in the above-described fourth to eighth embodiments, the present invention is not limited to this, and the above-described joysticks 15a and 15b may be provided for each in-vivo image simultaneously displayed on the image display device. For example, the operation input unit according to the present invention may be provided with a set of the joysticks 15a and 15b for operating the magnetic guidance of the capsule medical device while referring to the in-vivo image P1 in the display screen and a set of the joysticks 15a and 15b for operating the magnetic guidance of the capsule medical device while referring to the in-vivo image P2. In this case, each set of the joysticks 15a ad 15b may be arranged on a single operation input unit main body, or may be arranged on separate operation input unit main bodies.

Also, although the arrow information indicating the magnetic guidance direction such as the turning direction and the motion direction of the capsule medical device is displayed on the display unit of the control device in the above-described first to eighth embodiments, the present invention is not limited to this, and may display the arrow information indicating such a magnetic guidance direction on the display unit of the image display device displaying the in-vivo image. In this case, the display unit of the image display device may display the arrow information in such a magnetic guidance direction only when the operation information is input, or may always display the arrow information in such a magnetic guidance direction regardless of the presence of the input of the operation information and change the display color of the arrow information in such a magnetic guidance direction when the operation information is input. Also, the display unit of the image display device may display the arrow information in the magnetic guidance direction so as to be overlapped with the in-vivo image of the subject, and in this case, it is possible to blink the arrow information of the magnetic guidance direction so as not to prevent the observation of the in-vivo image. Further, the display location of the arrow information in such an in-vivo image may be determined in consideration of the distortion of the optical system of the capsule medical device.

Further, although the elevation angle and the direction angle (that is to say, the position) of the capsule medical device are calculated based on the magnetic field direction of the guidance magnetic field or the like applied to the capsule medical device, which is the magnetic guidance target in the above-described first to eighth embodiments, the present invention is not limited to this, and the position detector for detecting the position of the capsule medical device in the absolute coordinate system may be further provided, and the elevation angle and the direction angle of the capsule medical device may be calculated based on the detection result of the position detector, and the information of the calculated elevation angle direction angle may be displayed.

Also, although the location of the capsule medical device in the subject is calculated based on the relative location relation between the bed supporting the subject and the magnetic field generator in the above-described first to sixth embodiments, the present invention is not limited to this, and the location detector for detecting the location of the capsule medical device in the subject may be further displayed and the location information of the capsule medical device in the subject may be displayed based on the location detection result of the capsule medical device by the location detector.

Further, although the capsule medical device is magnetically guided by using the magnetic field generator for generating the magnetic field, which magnetically captures the capsule medical device in the subject in the vicinity of the central axis in the above-described first to sixth embodiments, the present invention is not limited to this, and the capsule medical device in the subject may be magnetically guided by using the magnetic field generator capable of generating the homogeneous magnetic field for controlling the position of the capsule medical device and the gradient magnetic field for controlling the location of the capsule medical device.

Also, although the body posture of the subject is set by using the body posture setting unit and the operation input unit in the above-described first to eighth embodiments, the present invention is not limited to this, and the above-described control device may detect the body posture of the subject based on the output of a gravity sensor attached to the subject. In this case, the control device displays the mark in a setting field of the body posture setting menu conforming to the body detection result of the subject, and displays the subject pattern image so as to indicate the body posture conforming to the body posture detection result. Meanwhile, the antenna 9a of the above-described receiving device 9 may be provided with such a gravity sensor. In this case, the output signal of such a gravity sensor may be input to the image display device and the control device through the receiving device 9.

Further, although the magnetic guidance of the capsule medical device is operated by the operation of the joysticks 15a and 15b in the above-described first to eighth embodiments, the present invention is not limited to this, and a plurality of cross-shaped input buttons may be provided on the operation input unit in place of the joysticks 15a and 15b to operate the magnetic guidance of the capsule medical device by the operation of such cross-shape input buttons.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A system for guiding capsule medical device, comprising:
    a capsule medical device that includes therein first and second imaging units that image images in imaging directions different from each other and a permanent magnet;
    a magnetic guidance device that applies a magnetic field to the permanent magnet to magnetically guide the capsule medical device in a subject;
    an operation input unit that receives operation information to operate magnetic guidance of the capsule medical device;
    a control device that controls the magnetic guidance device to magnetically guide the capsule medical device in response to the operation information input through the operation input unit; and
    an image display device that displays a first in-vivo image of the subject imaged by the first imaging unit and a second in-vivo image of the subject imaged by the second imaging unit, and indicates which of the first and second in-vivo images is an operation target image at the time of the magnetic guidance of the capsule medical device, wherein
        the image display device indicates the operation target image by adding a frame image to the operation target image out of the first and second in-vivo images, or
        the image display device indicates the operation target image by enlarging a display size of the operation target image relative to a non-operation target image out of the first and second in-vivo images.

2. The system for guiding capsule medical device according to claim 1, wherein
    the control device calculates an angle between the imaging direction of one of the first and second imaging units and a vertical axis based on information of the magnetic field applied to the permanent magnet when the magnetic guidance device magnetically guides the capsule medical device, physical information of the capsule medical device, and density information of a liquid, and
    the image display device displays angle information indicating the angle calculated by the control device by relating the angle information to the operation target image.

3. The system for guiding capsule medical device according to claim 1, wherein
    the control device calculates a horizontal component direction of the imaging direction of the imaging unit that corresponds to the operation target image out of the first and second imaging units based on information of the magnetic field applied to the permanent magnet when the magnetic guidance device magnetically guides the capsule medical device, and the image display device displays direction information indicating the horizontal component direction calculated by the control device by relating the direction information to the operation target image.

4. The system for guiding capsule medical device according to claim 1, wherein the control device calculates a horizontal component direction of the imaging direction of the imaging unit that corresponds to the operation target image out of the first and second imaging units based on information of the magnetic field applied to the permanent magnet when the magnetic guidance device magnetically guides the capsule medical device, and the image display device displays information indicating a relation between the imaging direction of the imaging unit and a region of the subject based on the horizontal component direction calculated by the control device.

5. The system for guiding capsule medical device according to claim 1, wherein the control device notifies the image display device that the operation information is input, and the image display device displays information indicating that the operation information is input.

6. The system for guiding capsule medical device according to claim 1, wherein the operation information specifies at least a magnetic guidance direction of the capsule medical device.

7. The system for guiding capsule medical device according to claim 6, wherein the magnetic guidance direction of the capsule medical device includes a rotational direction around a vertical axis, a rotational direction around a horizontal axis, a vertical direction, a horizontal direction, the imaging direction of the first or second imaging unit, an upward and downward direction of an imaging surface of the first or second imaging unit, and a right and left direction of the imaging surface of the first or second imaging unit.

8. A system for guiding capsule medical device, comprising:

a capsule medical device that includes therein first and second imaging units that image images in imaging directions different from each other and a permanent magnet;

a magnetic guidance device that applies a magnetic field to the permanent magnet to magnetically guide the capsule medical device in a subject;

an operation input unit that receives operation information to operate magnetic guidance of the capsule medical device;

a control device that controls the magnetic guidance device to magnetically guide the capsule medical device in response to the operation information input through the operation input unit; and an image display device that displays a first in-vivo image of the subject imaged by the first imaging unit and a second in-vivo image of the subject imaged by the second imaging unit, and indicates which of the first and second in-vivo images is an operation target image at the time of the magnetic guidance of the capsule medical device, wherein the operation input unit receives a selection information for selecting the operation target image out of the first and second in-vivo images, the control device controls the magnetic guidance device to change a magnetic guidance direction of the capsule medical device in response to the selection information, and the image display device indicates, as the operation target image, the in-vivo image out of the first and second in-vivo images selected based on the selection information.

* * * * *